United States Patent
Hassig et al.

(10) Patent No.: US 11,642,345 B2
(45) Date of Patent: May 9, 2023

(54) REPLICATION STRESS PATHWAY AGENT COMPOSITIONS AND METHODS FOR TREATING CANCER

(71) Applicant: Boundless Bio, Inc., San Diego, CA (US)

(72) Inventors: Christian Hassig, San Diego, CA (US); Ryan Hansen, San Diego, CA (US); Snezana Milutinovic, San Diego, CA (US); Jason Christiansen, Carlsbad, CA (US); Zachary Hornby, San Diego, CA (US); Sudhir Chowdhry, San Diego, CA (US); Anthony Celeste, San Diego, CA (US); Kristen Turner, San Diego, CA (US); Deepti Wilkinson, San Diego, CA (US)

(73) Assignee: BOUNDLESS BIO, INC., San Diego, CA (US)

( * ) Notice: Subject to any disclaimer, the term of this patent is extended or adjusted under 35 U.S.C. 154(b) by 0 days.

(21) Appl. No.: 18/048,573

(22) Filed: Oct. 21, 2022

(65) Prior Publication Data

US 2023/0078903 A1    Mar. 16, 2023

Related U.S. Application Data

(63) Continuation of application No. 17/568,434, filed on Jan. 4, 2022, now Pat. No. 11,547,711, which is a continuation of application No. PCT/US2021/045556, filed on Aug. 11, 2021.

(60) Provisional application No. 63/168,120, filed on Mar. 30, 2021, provisional application No. 63/064,555, filed on Aug. 12, 2020.

(51) Int. Cl.
  *A61K 31/517*  (2006.01)
  *A61P 35/00*   (2006.01)
  *A61K 45/06*   (2006.01)

(52) U.S. Cl.
  CPC ............ *A61K 31/517* (2013.01); *A61K 45/06* (2013.01); *A61P 35/00* (2018.01)

(58) Field of Classification Search
  CPC ........ A61K 31/517; A61K 45/06; A61P 35/00
  See application file for complete search history.

(56) References Cited

U.S. PATENT DOCUMENTS

| 2018/0355416 A1 | 12/2018 | Mischel et al. |
| 2020/0397796 A1 | 12/2020 | Hassig et al. |
| 2022/0143022 A1 | 5/2022 | Hassig et al. |

FOREIGN PATENT DOCUMENTS

| JP | S567007 A | 1/1981 | |
| WO | WO-2018136837 A1 * | 7/2018 | ............ A61P 35/00 |
| WO | WO-2019099736 A1 | 5/2019 | |
| WO | WO-2019165458 A1 | 8/2019 | |
| WO | WO-2020123530 A1 * | 6/2020 | ......... A61K 31/7105 |
| WO | WO-2020227255 A1 | 11/2020 | |
| WO | WO-2022035970 A1 | 2/2022 | |

OTHER PUBLICATIONS

Bartholomeusz et al. Gemcitabine Overcomes Erlotinib Resistance in EGFR-Overexpressing Cancer Cells through Downregulation of Akt. J Cancer 2:435-42 (2011).
Cohen et al. Extrachromosomal circles of satellite repeats and 5S ribosomal DNA in human cells. Mobile DNA 1:11 (2010).
Luo et al. Comparative profiling between primary colorectal carcinomas and metastases identifies heterogeneity on drug resistance. Oncotarget 7:63937-63949 (2016).
Ma et al. A Phase Ib Study of the FGFR/VEGFR Inhibitor Dovitinib With Gemcitabine and Capecitabine in Advanced Solid Tumor and Pancreatic Cancer Patients. Am J Clin Oncol 42(2):184-189 (2019).
PCT/US2021/045556 International Search Report and Written Opinion dated Nov. 22, 2021.
U.S. Appl. No. 17/568,434 Office Action dated Apr. 11, 2022.
U.S. Appl. No. 17/568,434 Office Action dated Aug. 22, 2022.
Walton et al. The clinical development candidate CCT245737 is an orally active CHK1 inhibitor with preclinical activity in RAS mutant NSCLC and Eμ-MYC driven B-cell lymphoma. Oncotarget 7:2329-2342 (2015).
Yokoi et al. Simultaneous inhibition of EGFR, VEGFR, and platelet-derived growth factor receptor signaling combined with gemcitabine produces therapy of human pancreatic carcinoma and prolongs survival in an orthotopic nude mouse model. Cancer Res 65(22):10371-80 (2005).
Yu et al. Gemcitabine eliminates double minute chromosomes from human ovarian cancer cells. PLoS One 8(8):e71988 (2013).

* cited by examiner

*Primary Examiner* — Theodore R. Howell
*Assistant Examiner* — George W Kosturko
(74) *Attorney, Agent, or Firm* — Wilson Sonsini Goodrich & Rosati

(57) ABSTRACT

Provided herein are methods of treating cancer in a subject, wherein the cancer is extrachromosomal DNA-positive (ecDNA-positive) or therapeutically resistant, the method comprising administering to the subject a therapeutically effective amount of a replication stress (RS) pathway agent alone or in combination with a targeted therapeutic.

7 Claims, 46 Drawing Sheets

MTX: methotrexate
ERL: erlotinib
GDC: GDC0575

REPLICATION STRESS PATHWAY AGENT COMPOSITIONS AND METHODS FOR TREATING CANCER

CROSS REFERENCE

This patent application is a continuation of U.S. application Ser. No. 17/568,434, filed Jan. 4, 2022, which is a continuation of international patent application number PCT/US2021/045556, filed Aug. 11, 2021, which claims the benefit of U.S. Provisional Application No. 63/064,555, filed Aug. 12, 2020, and U.S. Provisional Application No. 63/168,120, filed Mar. 30, 2021, all of which are incorporated by reference herein in their entirety.

BACKGROUND

Cancers often prove resistant to the therapeutics that are used to treat them, frustrating efforts to extend progression free survival in cancer patients. In some cases, treatment resistant cancers are observed to be positive for extrachromosomal DNA (ecDNA), which sometimes contains amplified oncogenes, contributing to therapeutic resistance.

SUMMARY

In an aspect, there are provided methods for treating a tumor or tumor cells in a subject. In some embodiments, the method comprises administering a replication stress pathway agent (RSPA) in an amount sufficient to induce replication stress in the tumor or tumor cells; and administering a cancer-targeted therapeutic agent, wherein the tumor or tumor cells have an ecDNA signature, and wherein growth or size of the tumor or growth or number of tumor cells is reduced. In some embodiments, the ecDNA signature is selected from the group consisting of a gene amplification; a p53 loss of function mutation; absence of microsatellite instability (MSI-H); a low level of PD-L1 expression; a low level of tumor inflammation signature (TIS); a low level of tumor mutational burden (TMB); an increased frequency of allele substitutions, insertions, or deletions (indels); and any combination thereof. In some embodiments, the gene amplification comprises an amplification of an oncogene, a drug-resistance gene, a therapeutic target gene, or a checkpoint inhibitor gene. In some embodiments, the cancer-targeted therapeutic agent is directed to an activity of a protein product of a target gene, and wherein the treatment with the cancer-targeted therapeutic agent and the RSPA reduces amplification or expression of the target gene in the tumor or tumor cells. In some embodiments, the cancer-targeted therapeutic agent is administered prior to the RSPA. In some embodiments, the tumor or tumor cells develop the ecDNA signature after administration of the cancer-targeted therapeutic agent. In some embodiments, the cancer-targeted therapeutic agent is administered concurrently with the RSPA. In some embodiments, the tumor or tumor cells develop the ecDNA signature prior to treatment. In some embodiments, the method prevents an increase of ecDNA in the tumor or tumor cells. In some embodiments, the cancer-targeted therapeutic agent targets a protein product of an oncogene. In some embodiments, the oncogene comprises a point mutation, an insertion, a deletion, a fusion, or a combination thereof. In some embodiments, the cancer-targeted therapeutic agent targets a gene selected from the group consisting of ABCB1, AKT, ALK, AR, BCL-2, BCR-ABL, BRAF, CDK4, CDK6, c-MET, EGFR. ER, ERBB3, ERRB2, AK, FGFR1, FGFR2, FGFR3, FGFR4, FLT3, GR, HRAS, IGF1R, KIT, KRAS, MCL-1, MDM2, MDM4, MTOR, MYC, MYCL, MYCN, NRAS, NRG1, NTRK1, NTRK2, NTRK3, PDGFR, PIK3Cδ, PIK3CA/B, RET, and ROS1. In some embodiments, the tumor or tumor cells comprise an amplification of a first gene or portion thereof. In some embodiments, the first gene is an oncogene or a drug resistance gene. In some embodiments, the amplification is present on ecDNA. In some embodiments, the first gene is selected from the group consisting of ABCB1, AKT, ALK, AR, BCL-2, BCR-ABL, BRAF, CDK4, CDK6, c-MET, EGFR. ER, ERBB3, ERRB2, AK, FGFR1, FGFR2, FGFR3, FGFR4, FLT3, GR, HRAS, IGF1R, KIT, KRAS, MCL-1, MDM2, MDM4, MTOR, MYC, MYCL, MYCN, NRAS, NRG1, NTRK1, NTRK2, NTRK3, PDGFR, PIK3Cδ, PIK3CA/B, RET, and ROS1. In some embodiments, the cancer-targeted therapeutic agent is directed against the first gene. In some embodiments, the subject has not been previously treated with the cancer-targeted therapeutic agent. In some embodiments, the tumor or tumor cells have not been previously treated with the cancer-targeted therapeutic agent. In some embodiments, the method prevents an increase of ecDNA in the tumor or tumor cells. In some embodiments, the tumor or tumor cells are resistant or non-responsive to a previous therapeutic agent prior to treatment with the cancer-targeted therapeutic agent and the RSPA. In some embodiments, the tumor or tumor cells have been previously treated with the previous therapeutic agent. In some embodiments, the subject has been previously treated with the previous therapeutic agent. In some embodiments, the cancer-targeted therapeutic agent is directed to an activity of a protein product of a target gene, and wherein the treatment with the cancer-targeted therapeutic agent and the RSPA reduces amplification or expression of the target gene in the tumor or tumor cells. In some embodiments, the target gene is an oncogene, a drug-resistance gene, a therapeutic target gene, or a checkpoint inhibitor gene. In some embodiments, the target gene is selected from the group consisting of ABCB1, AKT, ALK, AR, BCL-2, BCR-ABL, BRAF, CDK4, CDK6, c-MET, EGFR, ER, ERBB3, ERRB2, AK, FGFR1, FGFR2, FGFR3, FGFR4, FLT3, GR, HRAS, IGF1R, KIT, KRAS, MCL-1, MDM2, MDM4, MTOR, MYC, MYCL, MYCN, NRAS, NRG1, NTRK1, NTRK2, NTRK3, PDGFR, PIK3Cδ, PIK3CA/B, RET, and ROS1. In some embodiments, the ecDNA signature is known prior to beginning treatment of the tumor or tumor cells. In some embodiments, the ecDNA signature is known after beginning treatment of the tumor or tumor cells. In some embodiments, the method improves an objective response rate and/or extends a duration of treatment response as compared to treatment with the cancer-targeted therapeutic agent in the absence of the RSPA. In some embodiments, the method increases a period of progression free survival as compared to treatment with the cancer-targeted therapeutic agent in the absence of the RSPA.

In another aspect, there are provided methods of treating an ecDNA-associated tumor or tumor cells comprising administering a RSPA and a cancer-targeted therapeutic agent to a subject identified as having a tumor or tumor cells having ecDNA, wherein growth or size of the tumor or growth or number of the tumor cells is decreased as a result of treatment. In some embodiments, the tumor or tumor cells of the subject are identified as having an ecDNA signature. In some embodiments, the ecDNA signature is selected from the group consisting of a gene amplification; a p53 loss of function mutation; absence of microsatellite instability (MSI-H); a low level of PD-L1 expression; a low level of tumor inflammation signature (TIS); a low level of tumor mutational burden (TMB); an increased frequency of allele substitutions, insertions, or deletions (indels); and any combination thereof. In some embodiments, the gene amplification comprises amplification of an oncogene, a drug-resistance gene, a therapeutic target gene, or a checkpoint inhibitor gene. In some embodiments, the tumor or tumor cells are identified as having ecDNA by imaging ecDNA in cells, detecting ecDNA using an oncogene binding agent, or by DNA sequencing. In some embodiments, ecDNA is identified in circulating tumor DNA.

In various aspects of methods herein, in some embodiments, the tumor or tumor cells are comprised by a solid tumor. In some embodiments, presence of ecDNA in the solid tumor is reduced or abolished as a result of treatment. In some embodiments, a level of ecDNA is reduced in the solid tumor after treatment as compared to the level of ecDNA prior to treatment. In some embodiments, a level of oncogene amplification and/or a level of copy number variation (CNV) in the solid tumor is reduced after treatment as compared to the level of oncogene amplification and/or CNV in the solid tumor prior to treatment. In some embodiments, the tumor or tumor cells include circulating tumor cells. In some embodiments, presence of ecDNA in the circulating tumor cells is reduced or abolished as a result of treatment. In some embodiments, a level of ecDNA is reduced in the circulating tumor cells after treatment as compared to the level of ecDNA prior to treatment. In some embodiments, a level of oncogene amplification and/or a level of copy number variation (CNV) in the circulating tumor cells is reduced after treatment as compared to the level of oncogene amplification and/or CNV in the circulating tumor cells prior to treatment. In some embodiments, the presence or level of ecDNA is identified in circulating tumor DNA. In some embodiments, the RSPA is selected from the group consisting of a RNR inhibitor, an ATR inhibitor, a CHK1 inhibitor, a WEE1 inhibitor, and a PARG inhibitor. In some embodiments, the RNR inhibitor is selected from the group consisting of gemcitabine, hydroxyurea, triapine, 5-chloro-2-(n-((1S,2R)-2-(6-fluoro-2,3-dimethylphenyl)-1-(5-oxo-4,5-dihydro-1,3,4-oxadiazol-2-yl)propyl)sulfamoyl)benzamide, clofarabine, fluarabine, motexafin gadolinium, cladribine, tezacitabine, and COH29 (N-[4-(3,4-dihydroxyphenyl)-5-phenyl-1,3-thiazol-2-yl]-3,4-dihydroxybenzamide). In some embodiments, the CHK1 inhibitor is selected from the group consisting of GDC-0575, prexasertib, LY-2880070, SRA737, XCCS-605B, rabusertib (LY-2603618), SCH-900776, RG-7602, AZD-7762, PF-477736, and BEBT-260. In some embodiments, the WEE1 inhibitor is selected from the group consisting of AZD1775 (MK1775), ZN-c3, Debio 0123, IMP7068, SDR-7995, SDR-7778, NUV-569, PD0166285, PD0407824, SC-0191, DC-859/A, bosutinib, and Bos-I. In some embodiments, the ATR inhibitor is selected from the group consisting of RP-3500, M-6620, berzosertib (M-6620, VX-970; VE-822), AZZ-6738, AZ-20, M-4344 (VX-803), BAY-1895344, M-1774, IMP-9064, nLs-BG-129, SC-0245, BKT-300, ART-0380, ATRN-119, ATRN-212, NU-6027. In some embodiments, the cancer targeted therapeutic agent is selected from the group consisting of abemaciclib, ado-trastuzumab emtansine, afatinib, alectinib, ALRN-6924, AMG232, AMG-510, apatinib, ARS-3248, AXL1717, bevacizumab, bortezomib, brigatinib, cabozantinib, capmatinib, ceritinib, cetuximab, CGM097, crizotinib, crizotinib, dabrafenib, dacomitinib, dasatinib, doxorubicin, DS-3032b, encorafenib, entrectinib, erdafitinib, erlotinib, everolimus, fam-trastuzumab deruxtecan, figitumumab, gefitinib, gossypol, HDM201, idasanutlin, imatinib, infigratinib, iniparib, lapatinib, larotrectinib, LEE011, lenvatinib, LGX818, lorlatinib, MEK162, MK-8242 (SCH-900242), MRTX849, navitoclax, necitumumab, nilotinib, obatoclax, olaparib, OSI-906, osimertinib, palbociclib, panitumumab, PD-0332991, perisofine, pertuzumab, PL225B, repotrectinib, ribociclib, RO5045337, salinomycin, salirasib, SAR405838 (MI-77301), sorafenib, sotorasib, sunitinib, tamoxifen, temsirolimus, tipifanib, tivanitab, tofacitinib, trametinib, trastuzumab, tucatinib, UPR1376, VAL-083, vemurafenib, vemurafenib, vintafolide, and zoptarelin. In some embodiments, the RSPA is an RNR inhibitor and the RSPA is administered at a sub-therapeutic dose relative to its recommended use as a single agent. In some embodiments, the RNR inhibitor is gemcitabine. In some embodiments, the RNR inhibitor is not gemcitabine or hydroxyurea. In some embodiments, the RSPA is not gemcitabine. In some embodiments, the RSPA is not gemcitabine when the cancer-targeted therapeutic agent is an EGFR inhibitor.

In an aspect, there are provided methods for treating cancer in a subject in need thereof. In some cases, the method comprises: administering to the subject a therapeutically effective amount of a replication stress (RS) pathway inhibitor, (also referred to herein as a replication stress pathway agent or RSPA), wherein the cancer has been determined to be extrachromosomal DNA-positive (ecDNA-positive). In some cases, the RS pathway inhibitor comprises a RNR inhibitor, an ATR inhibitor, a CHK1 inhibitor, an E2F inhibitor, an WEE1 inhibitor, a PARG inhibitor, or a RRM2 inhibitor. In some cases, the RNR inhibitor comprises Gemcitabine, hydroxyurea, triapine, or 5-chloro-2-(n-((1S,2R)-2-(6-fluoro-2,3-dimethylphenyl)-1-(5-oxo-4,5-dihydro-1,3,4-oxadiazol-2-yl)propyl)sulfamoyl) benzamide. In some cases, the CHK1 inhibitor comprises GDC-0575, prexasertib, or SRA737. In some cases, the ecDNA-positive cancer comprises an amplified oncogene on the ecDNA. In some cases, the oncogene comprises one or more of BRAF, CCND1, CDK4, CDK6, c-Myc, EGFR, ERB2, FGFR, HRAS, IGF1R, KRAS, MDM2, MDM4, MET, MYCL, MYCN, and NRAS. In some cases, the method further comprises administering to the subject a therapeutically effective amount of a targeted therapeutic that inhibits the protein product of the amplified oncogene. In some cases, the targeted therapeutic comprises abemaciclib, ado-trastuzumab emtansine, afatinib, alectinib, ALRN-6924, AMG232, AMG-510, apatinib, ARS-3248, AXL1717, AZD-3759, bevacizumab, bortezomib, brigatinib, cabozantinib, capmatinib, ceritinib, cetuximab, CGM097, crizotinib, dabrafenib, dacomitinib, dasatinib, DS-3032b, encorafenib, entrectinib, erdafitinib, erlotinib, everolimus, fam-trastuzumab deruxtecan, figitumumab, gefitinib, gossypol, HDM201, idasanutlin, imatinib, infigratinib, iniparib, lapatinib, larotrectinib, LEE011, lenvatinib, LGX818, lorlatinib, MEK162, MK-8242 SCH 900242, MRTX849, navitoclax, necitumumab, nilotinib, obatoclax, olaparib, OSI-906, osimertinib, palbociclib, panitumumab, PD-0332991, perisofine, pertuzumab, PL225B, repotrectinib, ribociclib, RO5045337, salinomycin, salirasib, SAR405838 MI-77301, sorafenib, sotorasib, sunitinib, tamoxifen, temsirolimus, tipifarnib, tivanitab, tofacitinib, trametinib, trastuzumab, tucatinib, UPR1376, VAL-083, vemurafenib, vemurafenib, vintafolide, or zoptarelin doxorubicin. In some cases, the RS pathway inhibitor and the targeted therapeutic are administered together. In some cases, the RS pathway inhibitor and the targeted therapeutic are administered separately.

In an aspect, there are provided, methods for treating a therapeutically resistant cancer in a subject. In some cases, the method comprises administering to the subject a therapeutically effective amount of (a) a replication stress (RS) pathway inhibitor, and (b) a targeted therapeutic. In some cases, the RS pathway inhibitor comprises a RNR inhibitor, an ATR inhibitor, a CHK1 inhibitor, a WEE1 inhibitor, an E2F inhibitor, or a RRM2 inhibitor. In some cases, the RNR inhibitor comprises Gemcitabine, hydroxyurea, triapine, or 5-chloro-2-(n-((1S,2R)-2-(6-fluoro-2,3-dimethylphenyl)-1-(5-oxo-4,5-dihydro-1,3,4-oxadiazol-2-yl)propyl)sulfamoyl) benzamide. In some cases, the CHK1 inhibitor comprises GDC-0575, prexasertib, or SRA737. In some cases, the therapeutically resistant cancer is ecDNA-positive. In some cases, the ecDNA-positive cancer comprises an amplified oncogene on the ecDNA. In some cases, the amplified oncogene comprises one or more of BRAF, CCND1, CDK4, CDK6, c-Myc, EGFR, ERB2, FGFR, HRAS, IGF1R, KRAS, MDM2, MDM4, MET, MYCL, MYCN, and NRAS. In some cases, the method further comprises administering to the subject a therapeutically effective amount of a targeted therapeutic that inhibits the protein product of the amplified oncogene. In some cases, the targeted therapeutic comprises abemaciclib, ado-trastuzumab emtansine, afatinib, alectinib, ALRN-6924, AMG232, AMG-510, apatinib, ARS-3248, AXL1717, AZD-3759, bevacizumab, bortezomib, brigatinib, cabozantinib, capmatinib, ceritinib, cetuximab, CGM097, crizotinib, dabrafenib, dacomitinib, dasatinib, DS-3032b, encorafenib, entrectinib, erdafitinib, erlotinib, everolimus, fam-trastuzumab deruxtecan, figitumumab, gefitinib, gossypol, HDM201, idasanutlin, imatinib, infigratinib, iniparib, lapatinib, larotrectinib, LEE011, lenvatinib, LGX818, lorlatinib, MEK162, MK-8242 SCH 900242, MRTX849, navitoclax, necitumumab, nilotinib, obatoclax, olaparib, OSI-906, osimertinib, palbociclib, panitumumab, PD-0332991, perisofine, pertuzumab, PL225B, repotrectinib, ribociclib, RO5045337, salinomycin, salirasib, SAR405838 MI-77301, sorafenib, sotorasib, sunitinib, tamoxifen, temsirolimus, tipifarnib, tivanitab, tofacitinib, trametinib, trastuzumab, tucatinib, UPR1376, VAL-083, vemurafenib, vemurafenib, vintafolide, or zoptarelin doxorubicin. In some cases, the RS pathway inhibitor and the targeted therapeutic are administered together. In some cases, the RS pathway inhibitor and the targeted therapeutic are administered separately.

In an aspect, there are provided compositions comprising a replication stress (RS) pathway inhibitor and a targeted therapeutic. In some cases, the RS pathway inhibitor comprises a RNR inhibitor, an ATR inhibitor, a CHK1 inhibitor, a WEE1 inhibitor, an E2F inhibitor, or a RRM2 inhibitor. In some cases, the RNR inhibitor comprises Gemcitabine, hydroxyurea, triapine, or 5-chloro-2-(n-((1S,2R)-2-(6-fluoro-2,3-dimethylphenyl)-1-(5-oxo-4,5-dihydro-1,3,4-oxadiazol-2-yl)propyl)sulfamoyl)benzamide. In some cases, the CHK1 inhibitor comprises GDC-0575, prexasertib, or SRA737. In some cases, the targeted therapeutic targets a protein product of an oncogene. In some cases, the oncogene comprises BRAF, CCND1, CDK4, CDK6, c-Myc EGFR. ERB2, FGFR, HRAS, IGF1R, KRAS, MDM2, MDM4, MYCL, MYCN, MET, or NRAS. In some cases, the targeted therapeutic comprises abemaciclib, ado-trastuzumab emtansine, afatinib, alectinib, ALRN-6924, AMG232, AMG-510, apatinib, ARS-3248, AXL1717, AZD-3759, bevacizumab, bortezomib, brigatinib, cabozantinib, capmatinib, ceritinib, cetuximab, CGM097, crizotinib, dabrafenib, dacomitinib, dasatinib, DS-3032b, encorafenib, entrectinib, erdafitinib, erlotinib, everolimus, fam-trastuzumab deruxtecan, figitumumab, gefitinib, gossypol, HDM201, idasanutlin, imatinib, infigratinib, iniparib, lapatinib, larotrectinib, LEE011, lenvatinib, LGX818, lorlatinib, MEK162, MK-8242 SCH 900242, MRTX849, navitoclax, necitumumab, nilotinib, obatoclax, olaparib, OSI-906, osimertinib, palbociclib, panitumumab, PD-0332991, perisofine, pertuzumab, PL225B, repotrectinib, ribociclib, RO5045337, salinomycin, salirasib, SAR405838 MI-77301, sorafenib, sotorasib, sunitinib, tamoxifen, temsirolimus, tipifarnib, tivanitab, tofacitinib, trametinib, trastuzumab, tucatinib, UPR1376, VAL-083, vemurafenib, vemurafenib, vintafolide, or zoptarelin doxorubicin. In some cases, the RS pathway inhibitor is a CHK1 inhibitor and the targeted therapeutic is an EGFR inhibitor. In some cases, the composition comprises one or more pharmaceutically acceptable excipients.

In an aspect, there are provided methods for treating cancer in a subject. In some cases, the method comprises administering to the subject a therapeutically effective amount of a first targeted therapeutic until the cancer in the subject develops resistance to the first targeted therapeutic, followed by administering to the subject a therapeutically effective amount of a replication stress (RS) pathway inhibitor, thereby treating the cancer. In some cases, the first targeted therapeutic comprises abemaciclib, ado-trastuzumab emtansine, afatinib, alectinib, ALRN-6924, AMG232, AMG-510, apatinib, ARS-3248, AXL1717, AZD-3759, bevacizumab, bortezomib, brigatinib, cabozantinib, capmatinib, ceritinib, cetuximab, CGM097, crizotinib, dabrafenib, dacomitinib, dasatinib, DS-3032b, encorafenib, entrectinib, erdafitinib, erlotinib, everolimus, fam-trastuzumab deruxtecan, figitumumab, gefitinib, gossypol, HDM201, idasanutlin, imatinib, infigratinib, iniparib, lapatinib, larotrectinib, LEE011, lenvatinib, LGX818, lorlatinib, MEK162, MK-8242 SCH 900242, MRTX849, navitoclax, necitumumab, nilotinib, obatoclax, olaparib, OSI-906, osimertinib, palbociclib, panitumumab, PD-0332991, perisofine, pertuzumab, PL225B, repotrectinib, ribociclib, RO5045337, salinomycin, salirasib, SAR405838 MI-77301, sorafenib, sotorasib, sunitinib, tamoxifen, temsirolimus, tipifarnib, tivanitab, tofacitinib, trametinib, trastuzumab, tucatinib, UPR1376, VAL-083, vemurafenib, vemurafenib, vintafolide, or zoptarelin doxorubicin. In some cases, the RS pathway inhibitor comprises a RNR inhibitor, an ATR inhibitor, a CHK1 inhibitor, a WEE1 inhibitor, an E2F inhibitor, a RRM1 inhibitor, or a RRM2 inhibitor. In some cases, the RNR inhibitor comprises Gemcitabine, hydroxyurea, triapine, or 5-chloro-2-(n-((1S,2R)-2-(6-fluoro-2,3-dimethylphenyl)-1-(5-oxo-4,5-dihydro-1,3,4-oxadiazol-2-yl)propyl)sulfamoyl)benzamide. In some cases, the CHK1 inhibitor comprises GDC-0575, prexasertib, or SRA737. In some cases, the cancer is determined to be ecDNA-positive prior to administration of the RS pathway inhibitor. In some cases, the ecDNA comprises an amplified oncogene. In some cases, the amplified oncogene comprises one or more of BRAF, CCND1, CDK4, CDK6, c-Myc. EGFR, ERB2. FGFR, HRAS, IGF1R, KRAS, MDM2, MDM4, MET, MYCL, MYCN, and NRAS. In some cases, the method further comprises administering to the subject a second targeted therapeutic that inhibits the protein product of the amplified oncogene. In some cases, the second targeted therapeutic comprises abemaciclib, ado-trastuzumab emtansine, afatinib, alectinib, ALRN-6924, AMG232, AMG-510, apatinib, ARS-3248, AXL1717, AZD-3759, bevacizumab, bortezomib, brigatinib, cabozantinib, capmatinib, ceritinib, cetuximab, CGM097, crizotinib, dabrafenib, dacomitinib, dasatinib, DS-3032b, encorafenib, entrectinib, erdafitinib, erlotinib, everolimus, fam-trastuzumab deruxtecan, figitumumab, gefitinib, gossypol. HDM201, idasanutlin, imatinib, infigratinib, iniparib, lapatinib, larotrectinib, LEE011, lenvatinib, LGX818, lorlatinib, MEK162, MK-8242 SCH 900242, MRTX849, navitoclax, necitumumab, nilotinib, obatoclax, olaparib. OSI-906, osimertinib, palbociclib, panitumumab, PD-0332991, perisofine, pertuzumab, PL225B, repotrectinib, ribociclib, RO5045337, salinomycin, salirasib, SAR405838 MI-77301, sorafenib, sotorasib, sunitinib, tamoxifen, temsirolimus, tipifarnib, tivanitab, tofacitinib, trametinib, trastuzumab, tucatinib, UPR1376, VAL-083, vemurafenib, vemurafenib, vintafolide, orzoptarelin doxorubicin. In some cases, the first targeted therapeutic is administered in combination with the RS inhibitor, the second targeted therapeutic, or both.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

An understanding of the features and advantages of the present invention will be obtained by reference to the following detailed description that sets forth illustrative embodiments, in which the principles of the invention are utilized, and the accompanying drawings of which:

FIG. 40A shows RNR inhibition alters cell-proliferation/transformation. FIG. 40B shows FISH images quantifying changes in ecDNA carrying amplified oncogene counts. FIG. 40C shows inhibition of RNR results in blocked nucleotide synthesis and enhanced replication stress.

FIG. 41A shows increased sensitivity of ecDNA+ cells compared with ecDNA-cells to CHK1 inhibition. FIG. 41B shows ssDNA-damage induced replication stress with CHK1 pathway inhibition.

FIG. 42A shows DNA fiber analysis of ecDNA+ and ecDNA− cells treated with RNR inhibitor. FIG. 42B shows replication fork speed in ecDNA+ and ecDNA− cells treated with RNR inhibitor.

FIG. 43B shows DNA fiber analysis of ecDNA+ and ecDNA− cells treated with CHK1 inhibitor. FIG. 42B shows replication fork speed in ecDNA+ and ecDNA− cells treated with CHK1 inhibitor.

DETAILED DESCRIPTION

Numerous oncogene-directed therapies have demonstrated clinical efficacy against mutated or activated fusion oncogene targets, however these same therapies do not always yield good objective response rate (ORR) or progression-free survival (PFS) against tumors, especially when the same oncogene is amplified. Despite considerable effort, the oncology field has failed to address this significant unmet need cancer population characterized by amplified oncogenes. Data suggests a substantial proportion of these amplifications are focal amplifications that in some cases occur on extrachromosomal DNA (ecDNA), and this ecDNA phenomenon may account for lack of treatment success.

Figure 1:
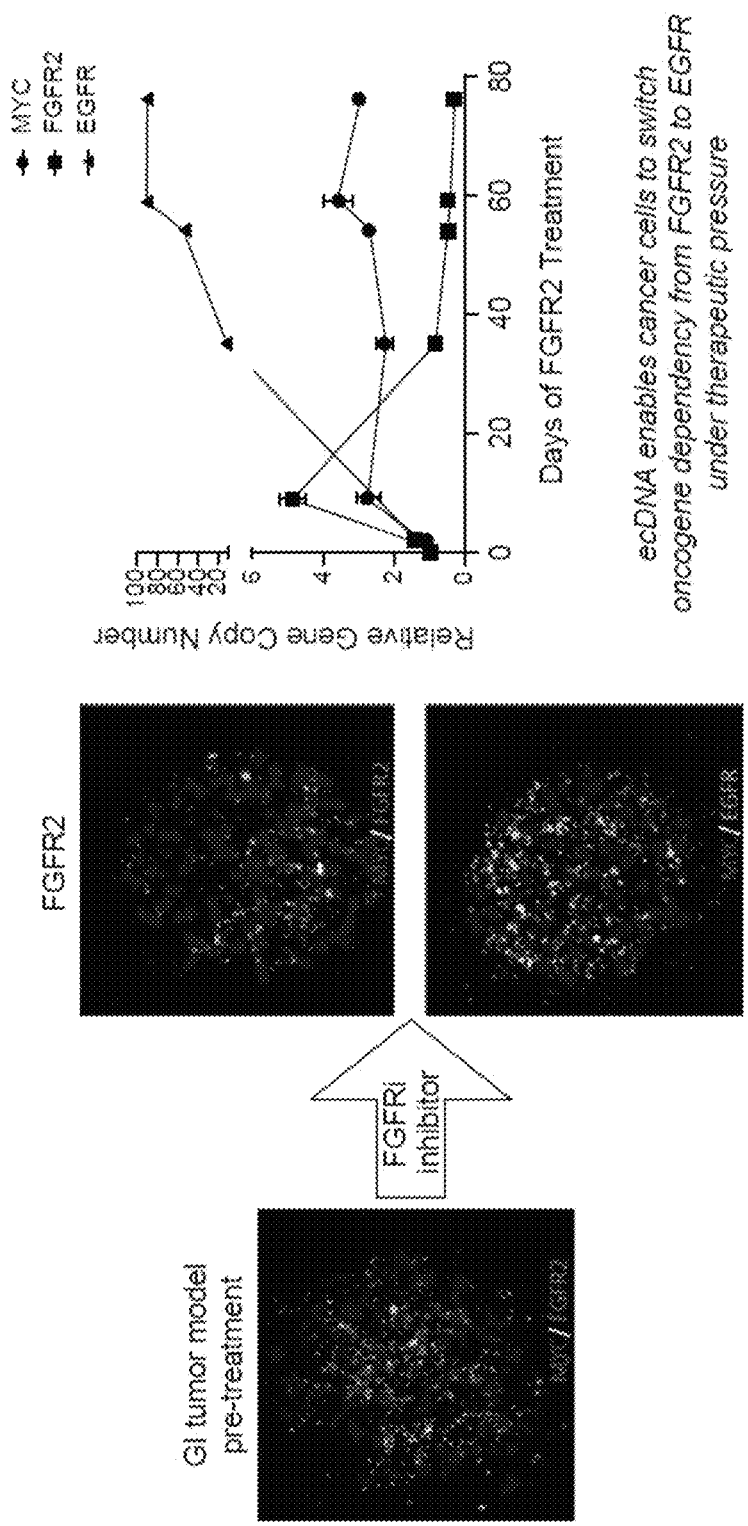
FIG. 1 shows ecDNA enable cancer cells to resist therapeutic pressure by altering oncogene dependency and this can be overcome by combination treatment with RNR inhibition using gemcitabine and another therapeutic agent.
Figure 25:
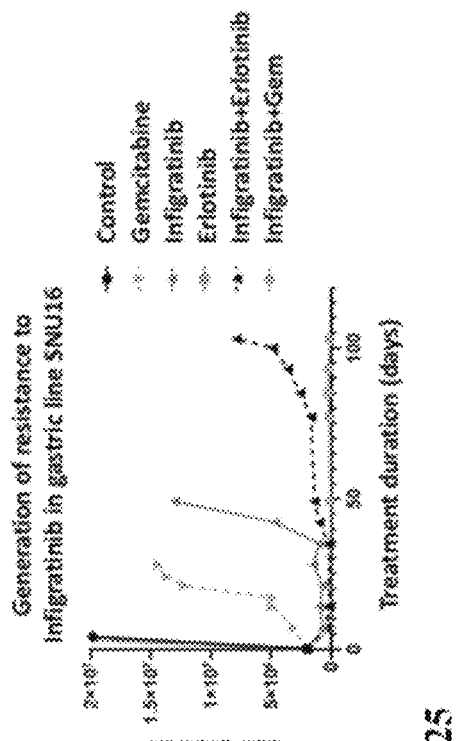
FIG. 25 shows growth of FGFR2 ecDNA-driven SNU16 cells in the presence of various agents.
Figure 25:
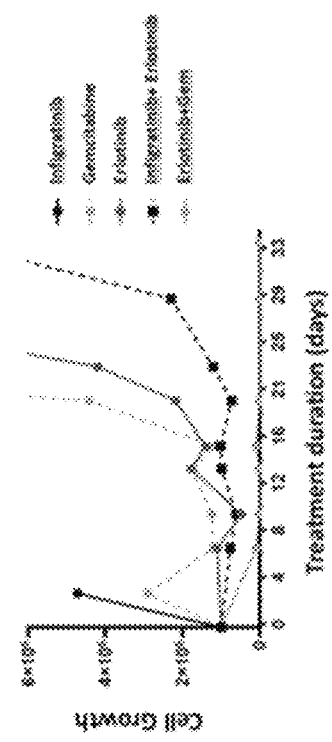
Figure 26:
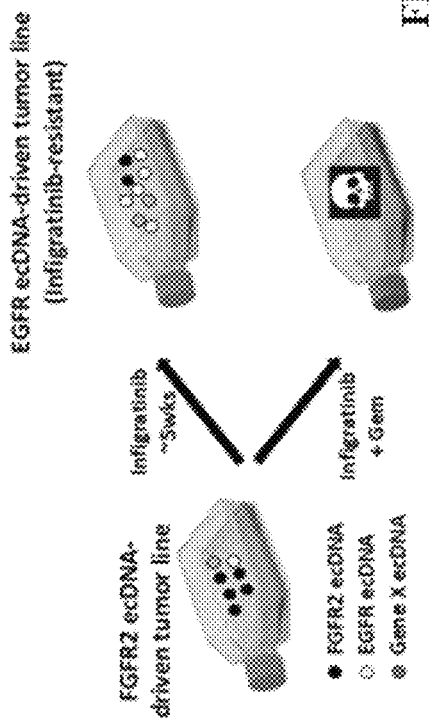
FIG. 26 shows growth of EGFR ecDNA-driven SNU16 cells in the presence of various agents.
Figure 26:
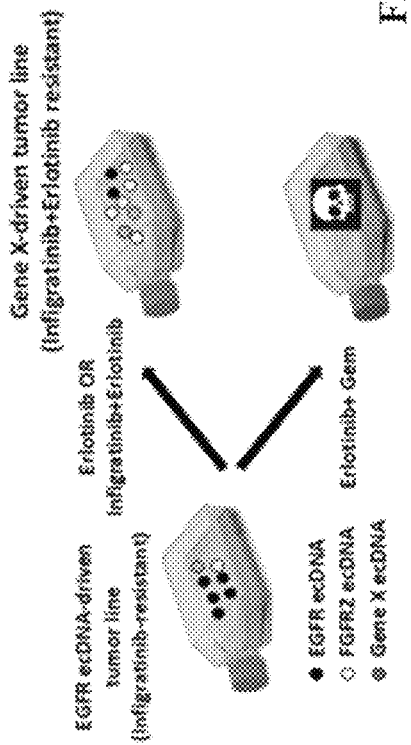

A SNU16 gastric cancer model shown in FIG. 1 recapitulates the clinical observation of "non-responsiveness" to targeted FGFR inhibitor therapy in the case of FGFR2 amplified cancers. The tumor cells predominantly harbor ecDNA amplified MYC and FGFR2. Although not shown here, the tumor cells demonstrate initial sensitivity to the FGFR inhibitor therapy, with substantial cell reduction in the first two weeks of treatment. However, by five weeks the cell line is growing normally again and is completely resistant to FGFR inhibition. This rapid resistance is correlated with a reduction in FGFR2 on ecDNA and a striking increase in EGFR on ecDNA. The underlying ecDNA machinery enables rapid oncogene repertoire change in response to targeted therapeutic pressure. The kinetics of this evolution in vitro are consistent with a clinical "non-responder" phenotype, despite the fact that the original tumor population was largely sensitive to FGFR inhibition. These findings help account for the observed lack of clinical efficacy demonstrated for oncogene-directed therapies (e.g. FGFR, EGFR. MET) when these oncogenes are activated via amplification. Therapeutically targeting the underlying ecDNA machinery constitutes an unprecedented and orthogonal strategy to overcome therapeutic resistance associated with oncogene amplified tumors. In accordance, FIG. 25 shows that simultaneous inhibition of FGFR2 with infigratinib and ecDNA with RNR inhibitor gemcitabine completely inhibits cell growth and prevents development of resistance. Similarly. FIG. 26 shows that cells that become resistant to infigratinib become mainly driven by EGFR amplification on ecDNA and are initially sensitive to EGFR inhibitor erlotinib but develop secondary resistance within three weeks. However, simultaneous inhibition of EGFR by erlotinib and RNR inhibition by gemcitabine completely inhibits cell growth and prevents development of secondary resistance. Importantly, upfront simultaneous inhibition of FGFR2 and EGFR by infigratinib and erlotinib, respectively, simply delays development of resistance.

Figure 2:
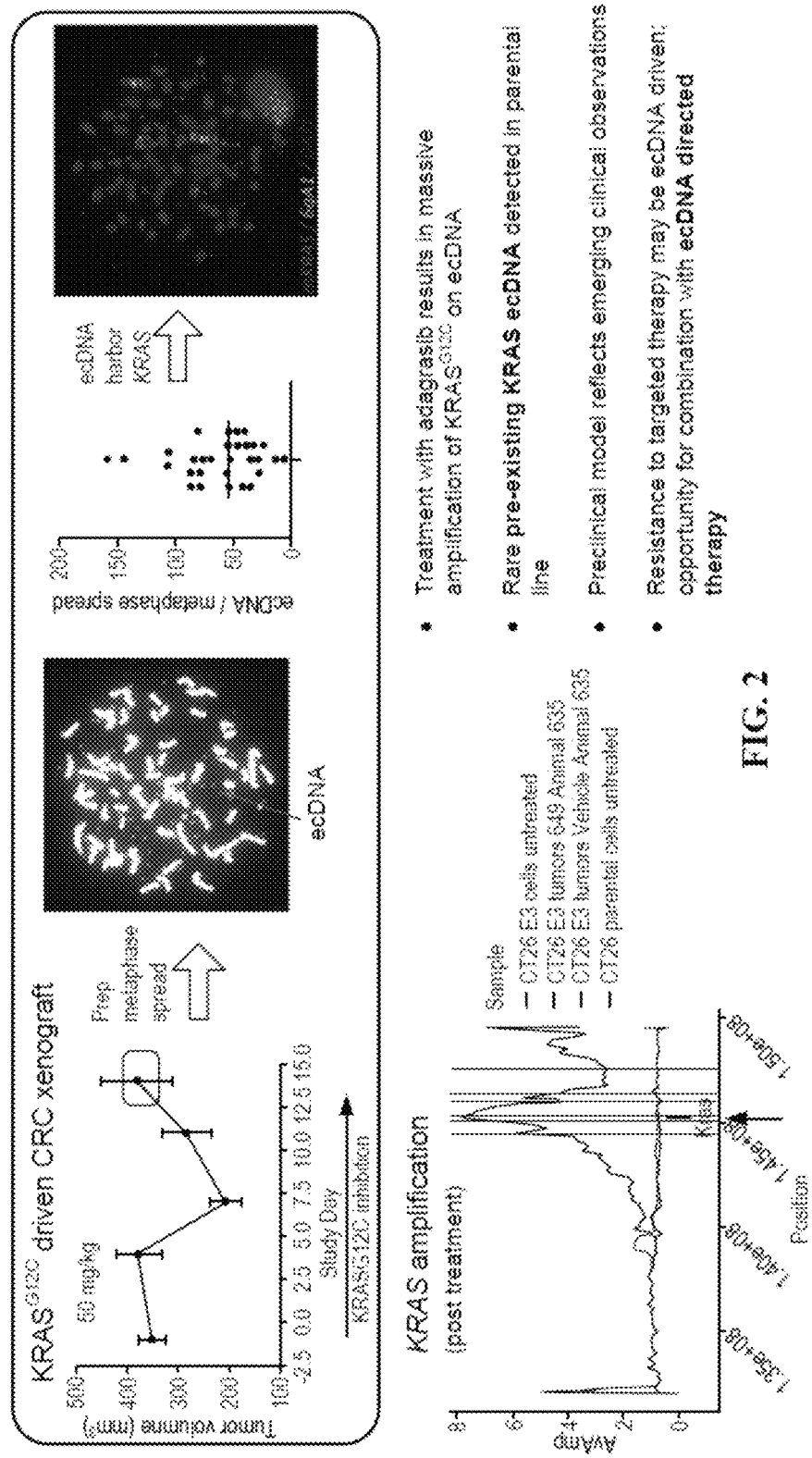
FIG. 2 shows rapid preclinical resistance (in vitro and in vivo) to treatment with a selective $KRAS^{G12C}$ inhibitor, adagrasib, in colorectal cancer (CRC) models is strongly associated with ecDNA.

A second in vivo model shown in FIG. 2 exemplifies another resistance mechanism associated with ecDNA wherein targeted therapy against activating mutant $KRAS^{G12C}$ using the selective KRASG12C inhibitor MRTX849 results in initial tumor reduction followed by rapid resistance and regrowth. The initial tumor does not have significant ecDNA, whereas the resistant tumor shows clear evidence of ecDNA harboring amplified $KRAS^{G12C}$. Prior published data is consistent with a similar likely ecDNA-mediated phenomenon of oncogene amplification driving resistance to EGFR and BRAF inhibitors in BRAF mutant colorectal cancer. These results indicate a unique utility for an ecDNA-directed therapy to address a major resistance mechanism associated with mutant activated MAPK pathway inhibition.

The oncology field has struggled to find the appropriate genetic background/sensitivity signature to successfully deploy Replication Stress (RS)-targeted therapies including ATR. CHK1 and WEE1. ATR inhibitors are showing some potential in ATM-mutant prostate cancer, but studies are ongoing. Synthetic lethality associated with oncogene amplification has been proposed (such as MYC, MYCN, MYCL, CCNE1 in particular, as they have been associated with increased RS), along with other genetic alterations and/or HPV+. The data supporting these dependencies were far from conclusive and too heterogeneous. Provided herein are methods wherein ecDNA-directed inhibition (inhibition of a replication stress pathway component) exhibits synthetic lethality with a cancer-targeted agent. In some cases, synthetic lethality with RS-targeted agents includes synthetic lethality of a cancer targeted agent with inhibition of a replication stress pathway component, such as with ribonucleotide reductase (RNR) or CHK1 inhibitors. In some cases, a tumor background is identified as hyper-sensitive to a replication stress pathway inhibition agent and allows a sufficient therapeutic index to enable tolerated doses that are efficacious. In some cases, inhibition of a component of the replication stress pathway results in reduced ecDNA copy number and enhanced cytotoxicity in ecDNA positive cells. In some cases, enhanced cytotoxicity results from the combination of the inhibition of a component of the replication stress pathway and inhibition of a cancer-target, such as an oncogene.

Methods of Treatment

In an aspect, provided herein are methods of treating cancer in a subject, for example methods of treating a tumor or tumor cells in a subject. In some cases, methods herein comprise administering a replication stress pathway agent (RSPA) in an amount sufficient to induce replication stress in the tumor or tumor cells. In some cases, the method further comprises administering a cancer-targeted therapeutic agent. In some cases, the tumor or tumor cells have an extrachromosomal deoxynucleic acid (ecDNA) signature. In some cases, growth or size of the tumor or growth or number of tumor cells is reduced.

In an aspect of methods herein, a tumor or tumor cells are determined to have an ecDNA signature. In some cases, a tumor or tumor cells are determined to have an ecDNA signature when the tumor or tumor cells have one or more characteristics associated with ecDNA+ tumors or tumor cells. For example, in some cases, the ecDNA signature is selected from the group consisting of a gene amplification; a p53 loss of function mutation; absence of microsatellite instability (MSI-H); a low level of PD-L1 expression; a low level of tumor inflammation signature (TIS); a low level of tumor mutational burden (TMB); an increased frequency of allele substitutions, insertions, or deletions (indels); and any combination thereof.

In an aspect of methods herein, the method further comprises administering a cancer-targeted therapeutic agent, directed to an activity of a protein product of a target gene. In some cases, the treatment with the cancer-targeted therapeutic agent and the RSPA reduces amplification or expression of the target gene in the tumor or tumor cells. In some cases, the cancer-targeted therapeutic agent is administered prior to the RSPA. In some cases, the cancer-targeted therapeutic agent is administered concurrently with the RSPA. In some cases, the cancer-targeted therapeutic agent is administered prior to the RSPA.

In an aspect of methods herein, the tumor or tumor cells have an ecDNA signature. In some cases, the tumor or tumor cells develop the ecDNA signature after administration of the cancer-targeted therapeutic agent. In some cases, the tumor or tumor cells develop the ecDNA signature prior to treatment. In some cases, the method prevents an increase of ecDNA in the tumor or tumor cells.

In an aspect of methods provided herein, the cancer-targeted therapeutic agent targets a protein product of an oncogene. In some cases, the oncogene comprises a point mutation, an insertion, a deletion, a fusion, or a combination thereof. In some cases, the cancer-targeted therapeutic agent targets a gene selected from the group consisting of AKT, ALK, AR, BCL-2, BCR-ABL, BRAF, CDK4, CDK6, c-MET, EGFR, ER. ERBB3, ERRB2, FAK, FGFR1, FGFR2, FGFR3, FGFR4, FLT3, GR, HRAS, IGF1R, KIT, KRAS, MCL-1, MDM2, MDM4, MTOR. MYC, MYCL, MYCN, NRAS, NRG1, NTRK1, NTRK2, NTRK3, PDGFR, PIK3CA/B, PIK3Cδ. RET, and ROS1. In some cases, the cancer-targeted therapeutic agent targets one or more genes provided in Table 1.

In an aspect of methods provided herein, the tumor or tumor cells comprise an amplification of a first gene or portion thereof. In some cases, the first gene is an oncogene. In some cases, the first gene is a drug resistance gene. In some cases, the amplification is present on ecDNA. In some cases, the first gene is selected from the group consisting of AKT, ALK, AR, BCL-2, BCR-ABL, BRAF, CDK4, CDK6, c-MET, EGFR, ER, ERRB2, ERBB3, FAK, FGFR1. FGFR2, FGFR3, FGFR4, FLT3, GR, HRAS, IGF1R, KRAS, KIT, MCL-1, MDM2, MDM4MTOR, NRAS, PDGFR, RET, and ROS1. In some cases, the first gene comprises one or more genes provided in Table 1. In some cases, the cancer-targeted therapeutic agent is directed against the first gene. In some cases, the subject has not been previously treated with the cancer-targeted therapeutic agent. In some cases, the tumor or tumor cells have not been previously treated with the cancer-targeted therapeutic agent. In some cases, the method prevents an increase of ecDNA in the tumor or tumor cells. In some cases, the method prevents a further increase in the amplification of the first gene. In some cases, such further amplification occurs if only the cancer-targeted therapeutic agent is administered, but when the treatment includes both the cancer-targeted therapeutic agent and the RSPA, the further increase in amplification is inhibited or prevented.

In an aspect of methods provided herein, the tumor or tumor cells are resistant or non-responsive to a previous therapeutic agent prior to treatment with the cancer-targeted therapeutic agent and the RSPA. In some cases, the tumor or tumor cells have been previously treated with the previous therapeutic agent. In some cases, the subject has been previously treated with the previous therapeutic agent. In some cases, after a period of treatment with the previous therapeutic agent, the tumor or tumor cells become resistant or non-responsive to such previous agent, and with the methods herein, when such tumor or tumor cells are treated with the cancer-targeted therapeutic agent (an agent that is, in some instances, different from the previous therapeutic agent) and the RSPA, the growth of the tumor or tumor cells is inhibited. In some cases, the treatment reduces the amount or level of ecDNA in the treated tumor or tumor cells or prevents a further increase in ecDNA amount or level.

In an aspect of methods provided herein, the cancer-targeted therapeutic agent is directed to an activity of a protein product of a target gene. In some cases, treatment with the cancer-targeted therapeutic agent and the RSPA reduces amplification or expression of the target gene in the tumor or tumor cells. In some cases, the target gene is an oncogene, a drug-resistance gene, a therapeutic target gene, or a checkpoint inhibitor gene. In some cases, the target gene is selected from the group consisting of KRAS, HRAS, NRAS, BRAF, EGFR, FGFR1, FGFR2, FGFR3, FGFR4, ALK, ROS1, RET, PDGFR, c-MET, IGF1R, FAK, BCR-ABL, MCL-1, CDK4, CDK6, ERRB2, ERBB3, MDM2, MTOR, FLT3, KIT, AKT, BCL-2, AR, ER, GR and MDM4. In some cases, the target gene comprises one or more genes provided in Table 1. In some cases, the target gene is found on or found amplified on ecDNA and treatment with the cancer-targeted therapeutic agent and the RSPA reduces ecDNA, including ecDNA comprising copies of the target gene.

In various aspects of methods provided herein, in some cases, the ecDNA signature of the tumor or tumor cells is known prior to beginning treatment of the tumor or tumor cells. For example, the tumor or tumor cells are biopsied or otherwise collected and assayed for one or more ecDNA signatures. In some cases, a determination of how to treat the tumor or tumor cells is based, in whole or in part, the presence or absence of an ecDNA signature. In some cases, the ecDNA signature is known after treatment of the tumor or tumor cells has commenced.

In an aspect of methods provided herein, the method of treatment with a cancer-targeted therapeutic agent and an RSPA improves an objective response rate and/or extends a duration of treatment response as compared to treatment with the cancer-targeted therapeutic agent in the absence of the RSPA. In some cases, the method increases a period of progression free survival as compared to treatment with the cancer-targeted therapeutic agent in the absence of the RSPA.

In an aspect, there are provided methods of treating an ecDNA-associated tumor or tumor cells. In some cases, the method comprises, administering a RSPA and a cancer-targeted therapeutic agent to a subject identified as having a tumor or tumor cells having ecDNA. In some cases, growth or size of the tumor or growth or number of the tumor cells is decreased as a result of treatment.

In an aspect of methods provided herein, the tumor or tumor cells of the subject are identified as having an ecDNA signature. In some cases, the ecDNA signature is selected from the group consisting of a gene amplification; a p53 loss of function mutation; absence of microsatellite instability (MSI-H); a low level of PD-L1 expression; a low level of tumor inflammation signature (TIS); a low level of tumor mutational burden (TMB); an increased frequency of allele substitutions, insertions, or deletions (indels); and any combination thereof.

In an aspect of methods provided herein, the tumor or tumor cells are identified as having ecDNA by imaging ecDNA in cells, detecting ecDNA using an oncogene binding agent, or by DNA sequencing. In some cases, ecDNA is identified in circulating tumor DNA.

In various aspects of methods provided herein, the tumor or tumor cells are comprised by a solid tumor. In some cases, presence of ecDNA in the solid tumor is reduced or abolished as a result of treatment with a cancer-targeted therapeutic agent and an RSPA. In some cases, a level of ecDNA is reduced in the solid tumor after treatment as compared to the level of ecDNA prior to treatment. In some cases, a level of oncogene amplification and/or a level of copy number variation (CNV) in the solid tumor is reduced after treatment with a cancer-targeted therapeutic agent and an RSPA as compared to the level of oncogene amplification and/or CNV in the solid tumor prior to treatment.

In various aspects of methods provided herein, the tumor or tumor cells include circulating tumor cells. In some cases, presence of ecDNA in the circulating tumor cells is reduced or abolished as a result of treatment with a cancer-targeted therapeutic agent and an RSPA. In some cases, a level of ecDNA is reduced in the circulating tumor cells after treatment as compared to the level of ecDNA prior to treatment. In some cases, a level of oncogene amplification and/or a level of copy number variation (CNV) in the circulating tumor cells is reduced after treatment as compared to the level of oncogene amplification and/or CNV in the circulating tumor cells prior to treatment. In some cases, the presence or level of ecDNA is identified in circulating tumor DNA.

In various aspects of methods provided herein that employ treatment with a RSPA and a cancer-targeted therapeutic agent, the RSPA is selected from the group consisting of a RNR inhibitor, an ATR inhibitor, a CHK1 inhibitor, a WEE1 inhibitor, and a PARG inhibitor. In some cases, the RNR inhibitor is selected from the group consisting of gemcitabine, hydroxyurea, triapine, 5-chloro-2-(n-((1S,2R)-2-(6-fluoro-2,3-dimethylphenyl)-1-(5-oxo-4,5-dihydro-1,3,4-oxadiazol-2-yl)propyl)sulfamoyl)benzamide, clofarabine, fludarabine, motexafin gadolinium, cladribine, tezacitabine, and COH29 (N-[4-(3,4-dihydroxyphenyl)-5-phenyl-1,3-thiazol-2-yl]-3,4-dihydroxybenzamide). In some cases, the CHK1 inhibitor is selected from the group consisting of GDC-0575, prexasertib, LY-2880070, SRA737, XCCS-605B, rabusertib (LY-2603618), SCH-900776, RG-7602, AZD-7762, PF-477736, and BEBT-260. In some cases, the WEE1 inhibitor is selected from the group consisting of AZD1775 (MK1775), ZN-c3, Debio 0123, IMP7068, SDR-7995, SDR-7778, NUV-569, PD0166285, PD0407824, SC-0191, DC-859/A, bosutinib, and Bos-I. In some cases, the ATR inhibitor is selected from the group consisting of RP-3500, M-6620, berzosertib (M-6620, VX-970; VE-822), AZZ-6738, AZ-20, M-4344 (VX-803), BAY-1895344, M-1774, IMP-9064, nLs-BG-129, SC-0245, BKT-300, ART-0380, ATRN-119, ATRN-212, NU-6027.

In various aspects of methods provided herein that employ treatment with a cancer-targeted therapeutic agent and an RSPA, the cancer targeted therapeutic agent is selected from the group consisting of abemaciclib, ado-trastuzumab emtansine, afatinib, alectinib, ALRN-6924, AMG232, AMG-510, apatinib, ARS-3248, AXL1717, AZD-3759, bevacizumab, bortezomib, brigatinib, cabozantinib, capmatinib, ceritinib, cetuximab, CGM097, crizotinib, dabrafenib, dacomitinib, dasatinib, DS-3032b, encorafenib, entrectinib, erdafitinib, erlotinib, everolimus, famtrastuzumab deruxtecan, figitumumab, gefitinib, gossypol, HDM201, idasanutlin, imatinib, infigratinib, iniparib, lapatinib, larotrectinib, LEE011, lenvatinib. LGX818, lorlatinib, MEK162, MK-8242 SCH 900242, MRTX849, navitoclax, necitumumab, nilotinib, obatoclax, olaparib, OSI-906, osimertinib, palbociclib, panitumumab. PD-0332991, perisofine, pertuzumab, PL225B, repotrectinib, ribociclib, RO5045337, salinomycin, salirasib, SAR405838 MI-77301, sorafenib, sotorasib, sunitinib, tamoxifen, temsirolimus, tipifarnib, tivanitab, tofacitinib, trametinib, trastuzumab, tucatinib, UPR1376, VAL-083, vemurafenib, vemurafenib, vintafolide, and zoptarelin doxorubicin. In some cases, the cancer targeted therapeutic agent targets a protein encoded by one or more genes provided in Table 1.

TABLE 1

Example Genes

| Gene | Description |
| --- | --- |
| ABCB(1-11) | ABC binding cassette subfamily A |
| ABCC(1-13) | ABC binding cassette subfamily C |
| ABCG(1-5) | ABC binding cassette subfamily G |
| ABL1 | encodes ABL kinase |
| AKT(1-3) | family encoding AKT serine/threonine kinases |
| ALK | anaplastic lymphoma kinase |
| NRC3C4 (AR) | androgen receptor |
| BCL2 | encodes BCL-2 apoptosis regulator |
| BCR | encodes breakpoint cluster region protein |
| BRAF | encodes B-raf serine/threonine kinase |
| CCND1 | Cyclin D1 |
| CCNE1 | Cyclin E1 |
| CDK4 | cell division protein kinase 4 |
| CDK6 | cell division protein kinase 6 |
| EGFR | Epidermal growth factor receptor (also known as ERBBI and HER1) |
| ERBB(1-4) | HER1-4 family of receptor proteins, including EGFR |
| ESR(1-2) | estrogen receptor (alpha and beta) |
| FAK | focal adhesion kinase |
| FGFR(1-4) | FGFR1-4 family of receptor proteins |
| FLT3 | FMS like tyrosine kinase 3, aka CD135 |
| NR3C1 (GR) | glucocorticoid receptor |
| HRAS | encodes RAS GTPase/signaling protein HRAS |
| IGF1R | insulin like growth factor receptor (IGF-1R) |
| KIT | encodes c-Kit, aka CD117 |
| KRAS | encodes RAS GTPase/signaling protein KRAS |
| MCL1 | encodes MCL-1, myeloid leukemia cell differentiation protein |
| MDM2 | mouse double minute 2 |
| MDM4 | mouse double minute 4 |
| MET | encodes c-Met protein (aka HGFR) |
| MTOR | encodes mechanistic target of rapamycin (mTOR) |
| MYC | encodes c-Myc |
| MYCL | encodes l-Myc |
| MYCN | encodes n-Myc |
| NRAS | encodes RAS GTPase/signaling protein NRAS |
| NRG1 | encodes neuregulin 1 |
| NTRK(1-3) | neurotrophic tyrosine receptor kinase |
| PDGFR | encodes platelet derived growth factor receptor |
| NR3C3 (PGR) | progesterone receptor |
| PIK3CA/B/D/G | encodes phosphatidylinositol 3-kinase subunits alpha/beta/delta/gamma |
| PIK3Cδ | encodes phosphatidylinositol 3-kinase delta |
| RET | encodes RET proto-oncogene |
| ROS1 | encodes ROS proto-oncogene 1 |
| S100A8(MRP8) | encodes S100 calcium binding protein A8 |

In an aspect of methods provided herein, the RSPA is an RNR inhibitor and the RSPA is administered at a sub-therapeutic dose relative to its recommended use as a single agent. In some cases, the RNR inhibitor is gemcitabine. Alternatively, the RNR inhibitor is not gemcitabine or hydroxy urea.

In an aspect of methods provided herein, the RSPA is not gemcitabine. In some cases, the RSPA is not gemcitabine when the cancer-targeted therapeutic agent is an EGFR inhibitor.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Certain Definitions

As used herein the term "about" or "approximately" means within an acceptable error range for the particular value as determined by one of ordinary skill in the art, which can depend in part on how the value is measured or determined. i.e., the limitations of the measurement system. For example, "about" can mean within 1 or more than 1 standard deviation, per the practice in the art. As another example, "about" can mean a range of up to 20%, up to 10%, up to 5%, or up to 1% of a given value. With respect to biological systems or processes, the term "about" can mean within an order of magnitude, such as within 5-fold or within 2-fold of a value. Where particular values are described in the application and claims, unless otherwise stated, the term "about" means within an acceptable error range for the particular value.

The term "subject," as used herein, generally refers to a vertebrate, such as a mammal (e.g., a human). Mammals include, but are not limited to, murines, simians, humans, farm animals, sport animals, and pets (e.g., a dog or a cat). Tissues, cells, and their progeny of a biological entity obtained in vivo or cultured in vitro are also encompassed. In some embodiments, the subject is a patient. In some embodiments, the subject is symptomatic with respect to a disease (e.g., cancer). Alternatively, in some cases, the subject is asymptomatic with respect to the disease. In some cases, the subject does not have the disease.

The term "biological sample," as used herein, generally refers to a sample derived from or obtained from a subject, such as a mammal (e.g., a human). Biological samples are contemplated to include but are not limited to, hair, fingernails, skin, sweat, tears, ocular fluids, nasal swab or nasopharyngeal wash, sputum, throat swab, saliva, mucus, blood, serum, plasma, placental fluid, amniotic fluid, cord blood, emphatic fluids, cavity fluids, earwax, oil, glandular secretions, bile, lymph, pus, microbiota, meconium, breast milk, bone marrow, bone, CNS tissue, cerebrospinal fluid, adipose tissue, synovial fluid, stool, gastric fluid, urine, semen, vaginal secretions, stomach, small intestine, large intestine, rectum, pancreas, liver, kidney, bladder, lung, and other tissues and fluids derived from or obtained from a subject.

The term "treating" as used herein, generally refers to administering an agent, or carrying out a procedure, for the purposes of obtaining an effect. In some cases, the effect is prophylactic in terms of completely or partially preventing a disease or symptom thereof and/or is therapeutic in terms of effecting a partial or complete cure for a disease and/or one or more symptoms of the disease. "Treatment," as used herein, may include treatment of a tumor in a mammal, particularly in a human, and includes: (a) preventing the disease or a symptom of a disease from occurring in a subject which may be predisposed to the disease but has not yet been diagnosed as having it (e.g., including diseases that may be associated with or caused by a primary disease; (b) inhibiting the disease, i.e., arresting its development; and (c) relieving the disease, i.e., causing regression of the disease. Treating may refer to any indicia of success in the treatment or amelioration or prevention of an cancer, including any objective or subjective parameter such as abatement; remission; diminishing of symptoms or making the disease condition more tolerable to the patient; slowing in the rate of degeneration or decline; or making the final point of degeneration less debilitating. The treatment or amelioration of symptoms is based on one or more objective or subjective parameters; including the results of an examination by a physician. Accordingly, the term "treating" includes the administration of the compounds or agents of the present invention to prevent or delay, to alleviate, or to arrest or inhibit development of the symptoms or conditions associated with cancer or other diseases. The term "therapeutic effect" refers to the reduction, elimination, or prevention of the disease, symptoms of the disease, or side effects of the disease in the subject.

The term "tumor" or "tumor cells" as used herein, generally refers to cells that grow and divide more than they should or do not die when they should. In some cases, tumor cells are present in a solid mass, such as a solid tumor, or in some cases, tumor cells are found in a non-solid form, such as in blood cancers. Tumor or tumor cells also can include metastasis or metastasizing cells, where cancer cells break away from the original (primary) tumor and may form a new tumor in other organs or tissues of the body.

The term "oncogene" as used herein, generally refers to a gene that has the potential to cause cancer when inappropriately activated. In tumors or tumor cells, these genes are often mutated to remove negative regulatory domains or expressed at high levels.

The term "ecDNA signature" as used herein, generally refers to one or more characteristics common to tumors or tumor cells that are ecDNA+. In some cases, the ecDNA signature is selected from the group consisting of a gene amplification; a p53 loss of function mutation; absence of microsatellite instability (MSI-H); a low level of PD-L1 expression; a low level of tumor inflammation signature (TIS); a low level of tumor mutational burden (TMB); an increased frequency of allele substitutions, insertions, or deletions (indels); and any combination thereof. In some cases, ecDNA signature includes a detection or identification of ecDNA using an imaging technology. In some cases, ecDNA signature does not include any imaging or direct detection of ecDNA.

The terms "replication stress pathway agent," "RSPA," "replication stress pathway inhibitor," and "RS pathway inhibitor" as used herein, generally refer to an agent that causes replication stress in a cell, such as a tumor cell. In some cases, the RSPA is an inhibitor of a replication stress pathway component, where inhibition increases replication stress. Replication stress as used herein refers to a stress that affects DNA replication and/or DNA synthesis and can include but is not limited to the slowing or stalling of replication fork progression and/or interference with DNA synthesis. Exemplary replication stress pathway agents include but are not limited to agents that inhibit RNR (ribonucleotide reductase), CHK1 (checkpoint kinase 1). ATR (Rad3-related protein), WEE1, E2F, PARG (poly(ADP ribose)glycohydrolase), or RRM2 (ribonucleotide reductase regulatory subunit 2).

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

EXAMPLES

The following examples are given for the purpose of illustrating various embodiments of the present disclosure and are not meant to limit the disclosure herein in any fashion. The present examples, along with the methods described herein are presently representative of preferred embodiments, are exemplary, and are not intended as limitations on the scope of the disclosure herein. Changes therein and other uses which are encompassed within the spirit of the disclosure as defined by the scope of the claims will occur to those having ordinary skill in the art.

Example 1: Inhibition of RS Pathway in ecDNA-Positive Cancer

Figure 3:
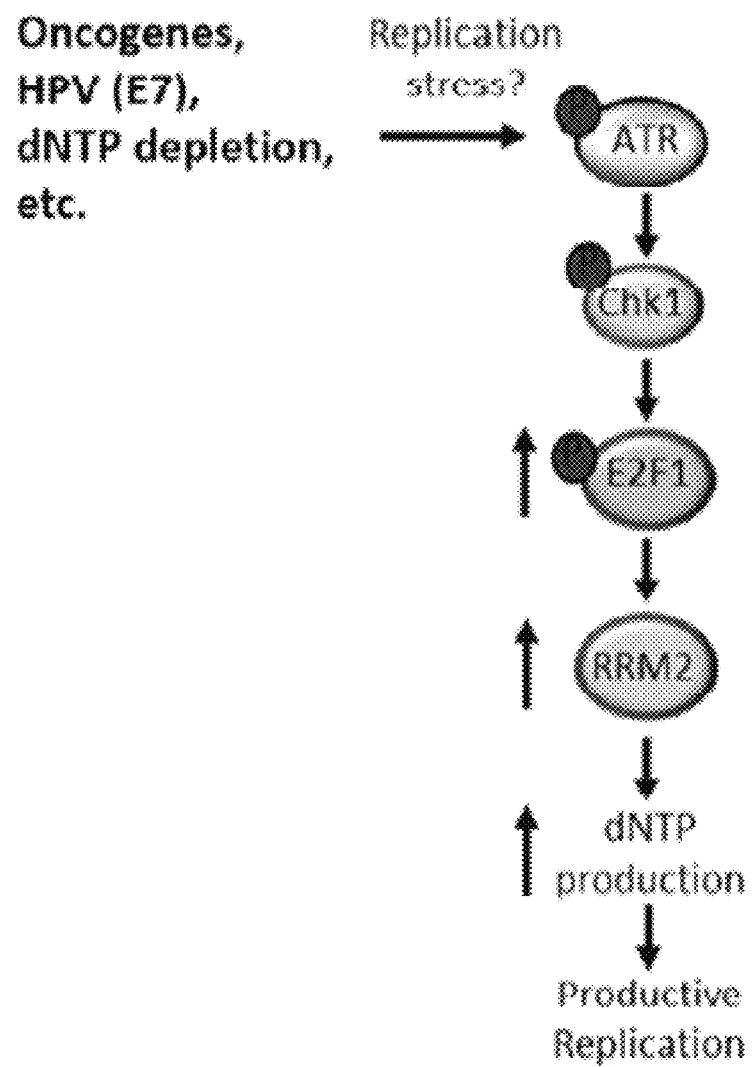
FIG. 3 shows ribonucleotide reductase (RNR) & CHK1 function in replication stress response.
Figure 4:
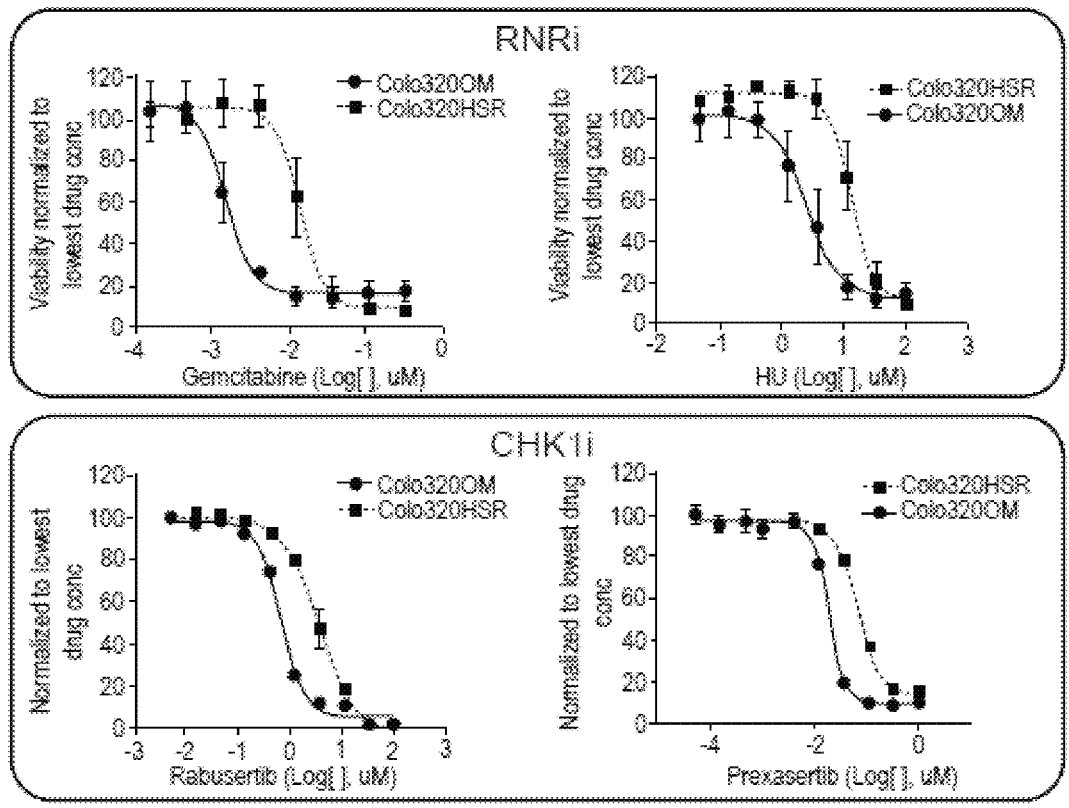
FIG. 4 shows ecDNA-driven tumor cells are more sensitive to inhibition of RNR or CHK1.
Figure 4:
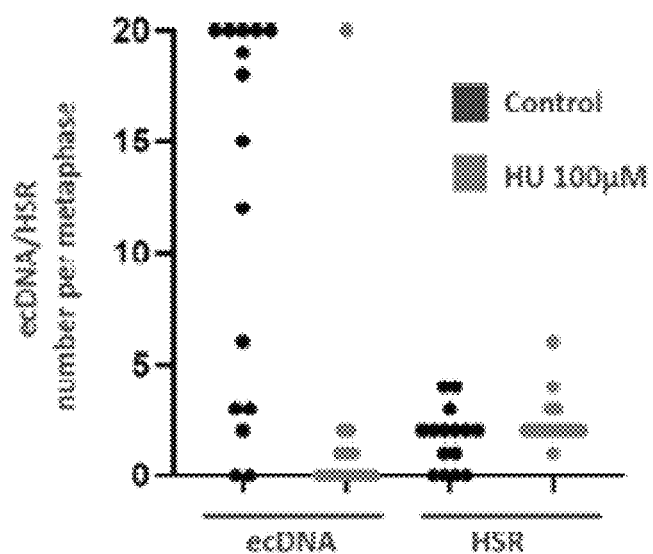

FIG. 3 illustrates the replication stress pathway that is activated in some cases by oncogenes such as HPV7 (E7), dNTP depletion, and other instances.

CHK1 and RNR function in the replication stress (RS) response pathway within the DNA damage response network. A range of factors in tumor cells may activate the RS pathway to maintain proliferation and survival during replication stress. Inhibition of targets in this pathway could be synthetically lethal in these tumor cells by elevating the level of RS to toxic levels. Both RNR and CHK1 are essential; therefore, two related challenges with clinical development of RNR and CHK1 inhibitors is patient selection and therapeutic index.

Figure 12:
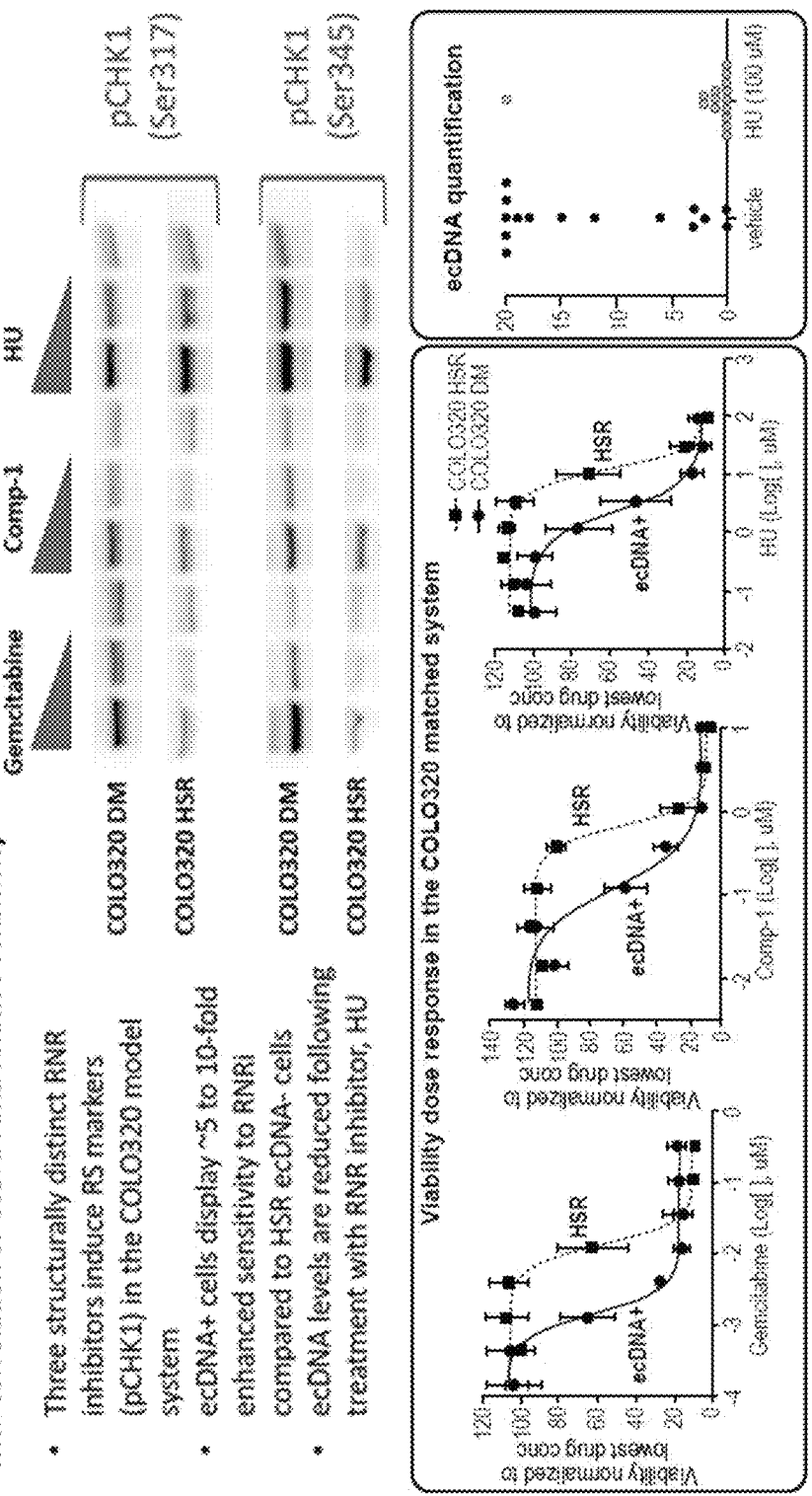
FIG. 12 shows structurally distinct RNR inhibitors induce replication stress markers in Colo320 system with correlation to ecDNA and relative sensitivity.

FIG. 12 illustrates ecDNA-driven tumor cells are more sensitive to inhibition of RNR or CHK1. Multiple structurally distinct inhibitors of RNR and CHK1 demonstrate ~5-10 fold enhanced toxicity in ecDNA-driven tumor cells compared to matched non-ecDNA bearing cells. Treatment with an RNR inhibitor results in reduced copies of MYC-encoding ecDNA.

Colo320 ecDNA+ (cell line COLO320 DM) and Colo320 ecDNA– (chromosomally amplified, cell line COLO320 HSR) cells (colorectal adenocarcinoma cell lines, ATCC) were treated with three structurally distinct RNR inhibitors, gemcitabine, hydroxyurea (HU), or compound 1 (comp-1 (5-chloro-2-(n-((1S,2R)-2-(6-fluoro-2,3-dimethylphenyl)-1-(5-oxo-4,5-dihydro-1,3,4-oxadiazol-2-yl)propyl)sulfamoyl) benzamide)). As shown in FIG. 12, ecDNA positive cells (Colo320 DM) were 5-10 fold more sensitive to the RNR inhibitor as compared to the ecDNA negative cell line (Colo320 HSR). All RNR inhibitors induced the replication stress marker, phosphorylation at serine positions 317 and 345 of CHK1, and in general the ecDNA positive cells had increased induction of this replication stress marker as compared to the ecDNA negative cells. The RNR inhibitor hydroxyurea (HU) treated ecDNA+ (Colo320 DM) cells and control cells (vehicle treated) were assessed for ecDNA. The vehicle treated cell line had high levels of ecDNA, as expected, whereas after treatment with the RNR inhibitor, hydroxyurea, the ecDNA copy number was markedly reduced.

Figure 13:
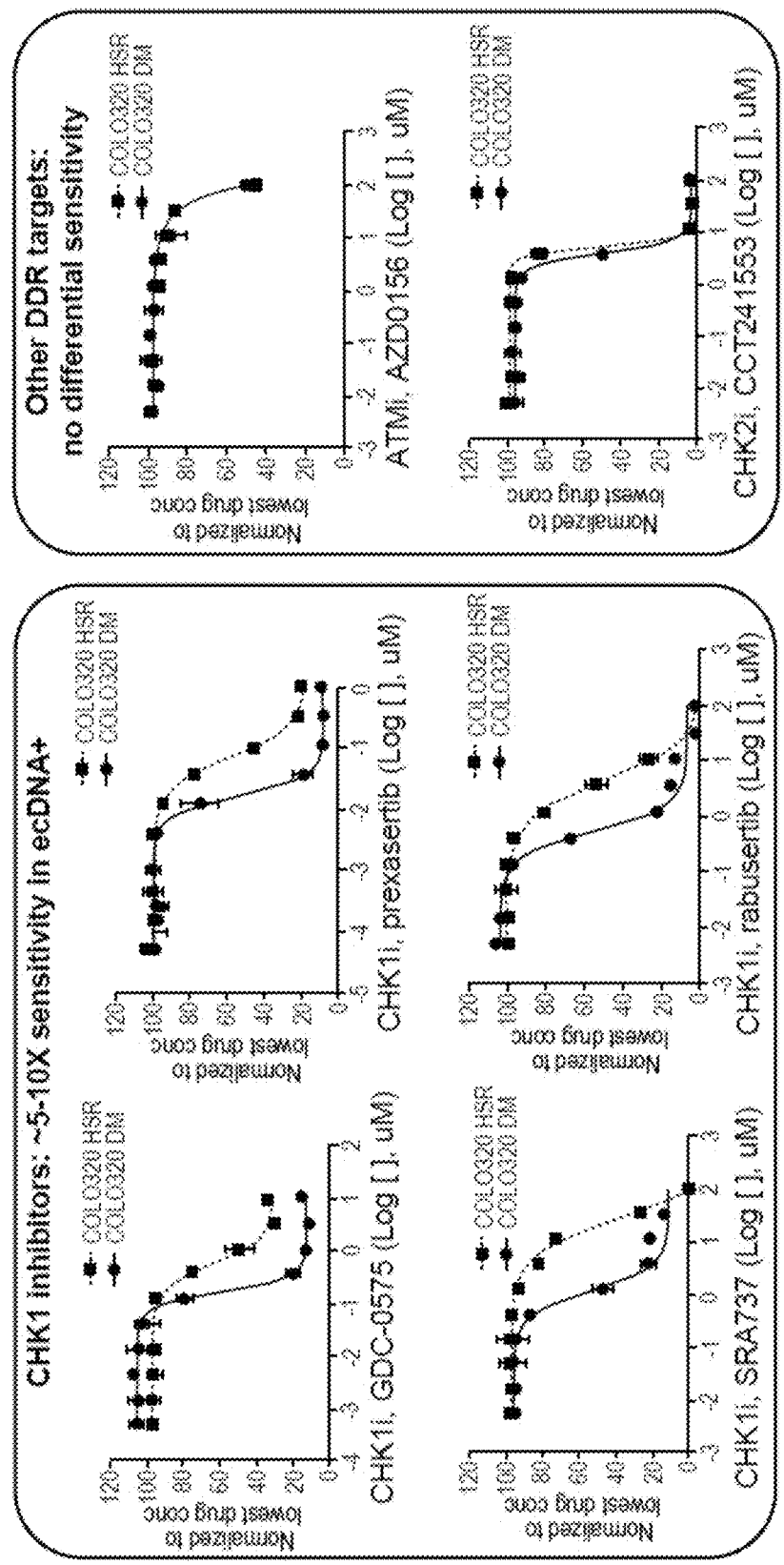
FIG. 13 shows ecDNA+ cells are more sensitive to CHK1 inhibitor (CHK1i) than ecDNA− cells.

The sensitivity of an ecDNA+ cell line (Colo320 DM) compared with an ecDNA– cell line (Colo320 HSR) to four structurally distinct CHK1 inhibitors was determined. The two cell lines were treated with GDC0575, Prexasertib, Rabusertib, or SRA737 for seven days. As shown in FIG. 13, Colo320 DM ecDNA+ cells displayed about 5-10 fold enhanced sensitivity to CHK1 inhibition compared with Colo320 HSR ecDNA– cells. In contrast, neither inhibiting CHK2 with CCT241533 nor inhibiting DDR target, ATM, with AZD0156 revealed any differential sensitivity between the two lines.

Figure 5:
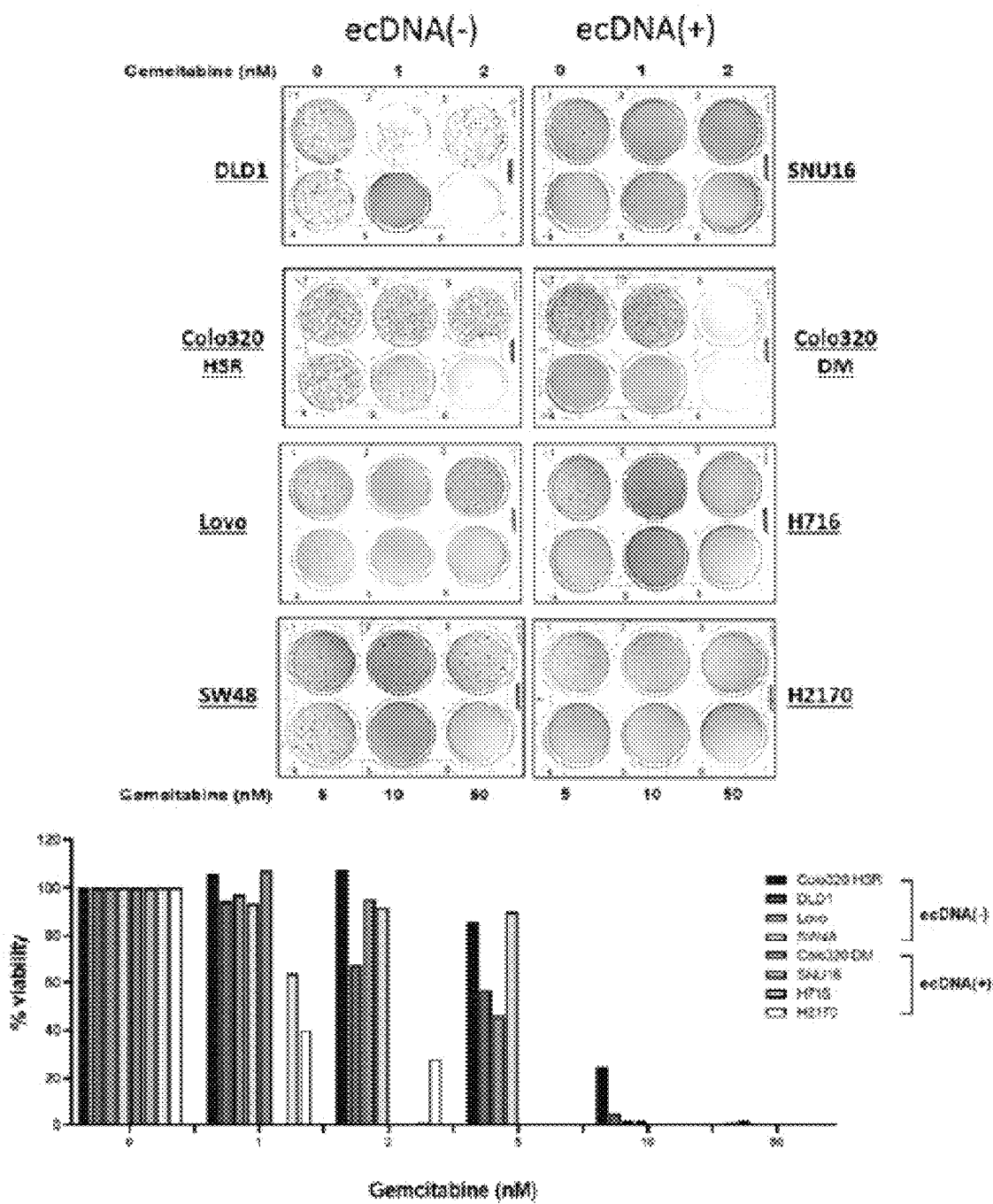
FIG. 5 shows differential sensitivity of ecDNA-positive (ecDNA(+)) versus ecDNA-negative (ecDNA(−)) cohort to inhibition of RNR using gemcitabine in a 3D colony formation assay.

FIG. 5 illustrates differential sensitivity of ecDNA-positive vs. ecDNA-negative cancer cells to inhibition of RNR using gemcitabine in a 3-dimensional colony formation assay conducted in soft-agar. A panel of ecDNA+ and ecDNA– cell lines were interrogated in a two-week soft-agar drug sensitivity assay. All lines were treated with a five-point dose range of gemcitabine for two weeks and stained with crystal violet (FIG. 5, top panel) to quantify individual colony counts by ImageJ analysis (plotted in FIG. 5, bottom panel). All ecDNA+ cell lines (SNU16, Colo320 DM, H716, and H2170) displayed 5-10 fold enhanced sensitivity to gemcitabine when compared with ecDNA– cell lines (DLD1, Colo320 HSR, Lovo, and SW48).

Figure 31:
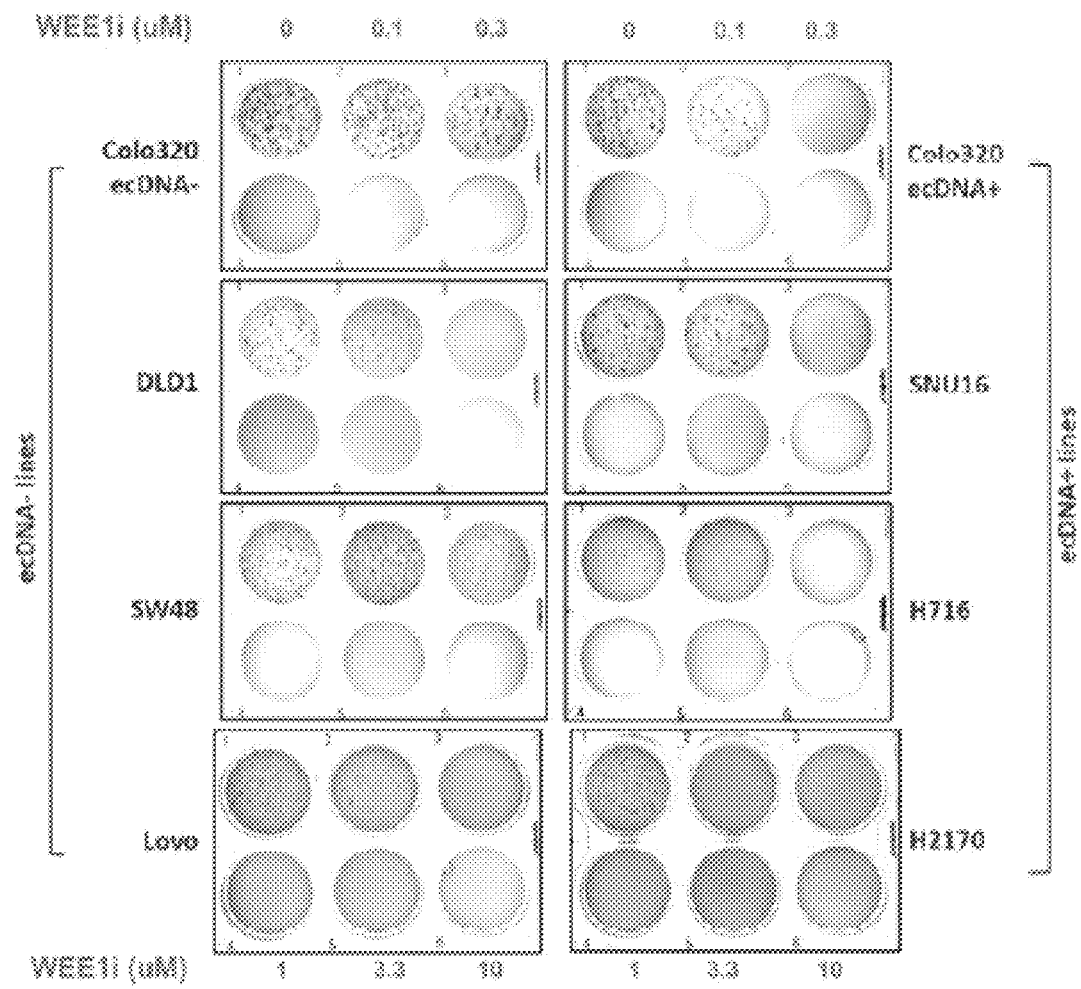
FIG. 31 shows sensitivity of ecDNA+ cells to WEE1 inhibition.

FIG. 31 illustrates sensitivity of ecDNA+ cells to inhibition of WEE1 using adavosertib in a 3-dimensional colony formation assay conducted in soft-agar. A panel of ecDNA+ cell lines were interrogated in a two-week soft agar drug sensitivity assay. All lines were treated with a five-point dose range of adavosertib for two weeks and stained with crystal violet to quantify individual colony counts. All cell lines demonstrated sensitivity to adavosertib.

Figure 32:
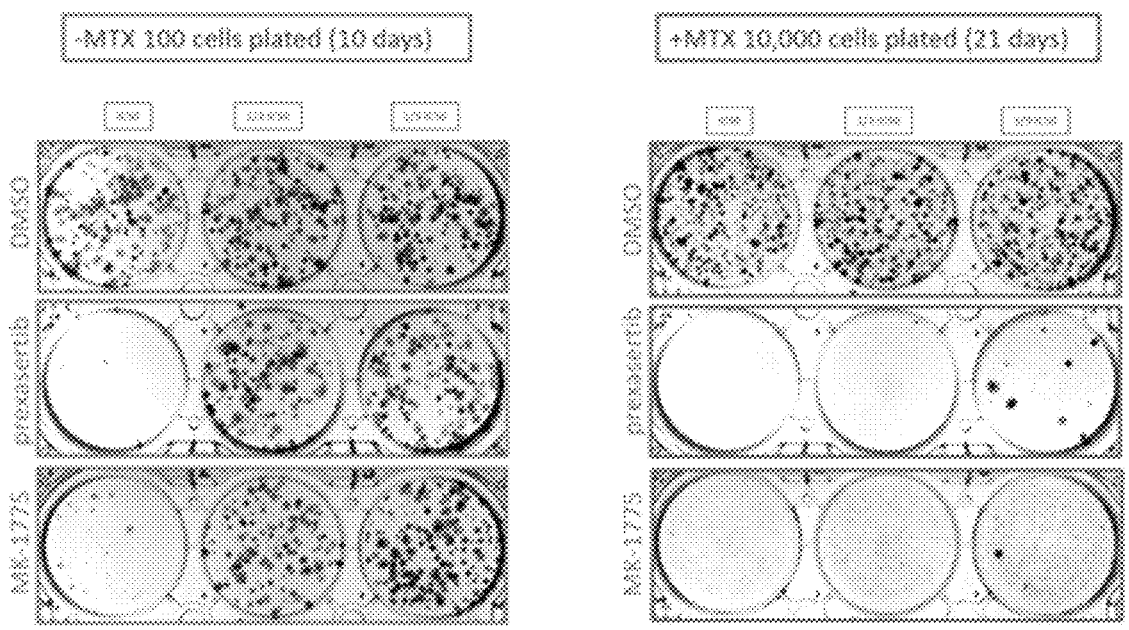
FIG. 32 shows WEE1 inhibition prevents methotrexate resistance.

FIG. 32 illustrates abrogation of resistance formation to methotrexate by WEE1 inhibition via adavosertib (MK-1775) in HeLa cells via colony formation assay. In FIG. 32 left panel, 100 cells were plated without methotrexate for 10 days then treated with DMSO, prexasertib (IC50, 1/3 IC50, or 1/9 IC50), or adavosertib (MK-1775) (IC50, 1/3 IC50, or 1/9 IC50). In FIG. 32, right panel, 10000 cells were plated with methotrexate for 21 days, and simultaneously treated with DMSO, prexasertib (IC50, 1/3 IC50, or 1/9 IC50), or adavosertib (MK-1775)(IC50, 1/3 IC50, or 1/9 IC50).

Sensitivity of an ecDNA+ (Colo320 DM) and an ecDNA– (Colo320 HSR) cell line models was determined by treating each with increasing concentrations of Prexasertib (CHK1i) over a seven day period. Cell proliferation was determined using MTS assay (FIG. 14, top left panel), while cytotoxicity was determined by measuring dead-cell protease activity using CytoTox-Glo assay (FIG. 14, top right panel). ecDNA bearing Colo320 DM showed enhanced sensitivity by 200 fold and 13.71 fold to the treatment with CHK1i when analyzing proliferation and cytotoxicity changes compared with Colo320 HSR ecDNA– cells.

Figure 14:
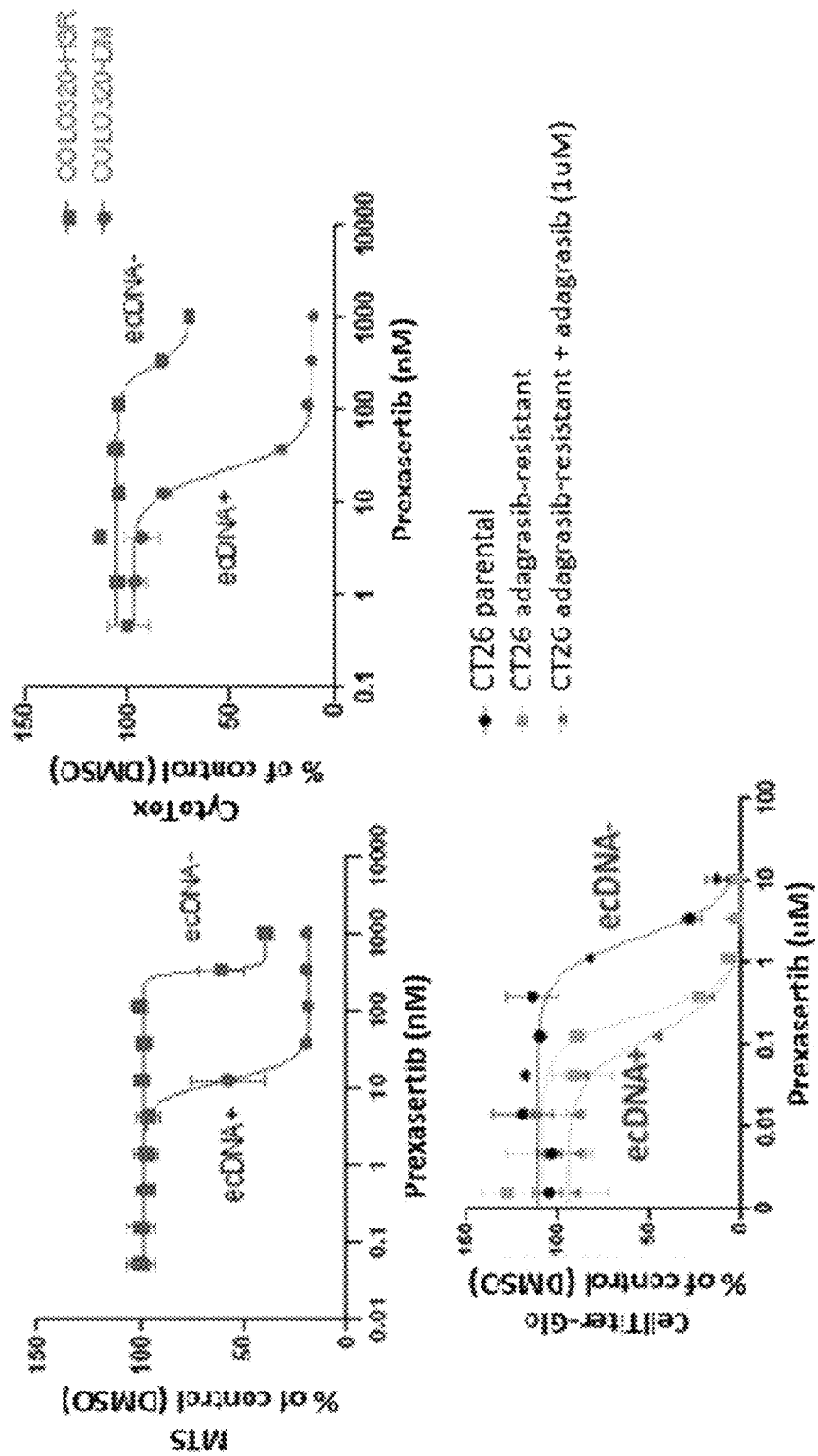
FIG. 14 shows assays and tumor cell models of ecDNA-dependent sensitivity to CHK1 inhibitors.

The sensitivity of parental CT26WT E3 cells (ecDNA– cell line) and adagrasib-resistant CT26WT E3 cells (ecDNA+) in the presence and absence of 1 μM adagrasib, to increasing concentrations of Prexasertib (CHK1i) for five days was determined using Cell Titer-glo assay. As shown in FIG. 14 bottom panel, adagrasib-resistant CT26WT E3 ecDNA+ cells displayed about 10 fold enhanced sensitivity to CHK1 inhibition compared with non-ecDNA bearing parental CT26WT E3 cells.

Figure 6:
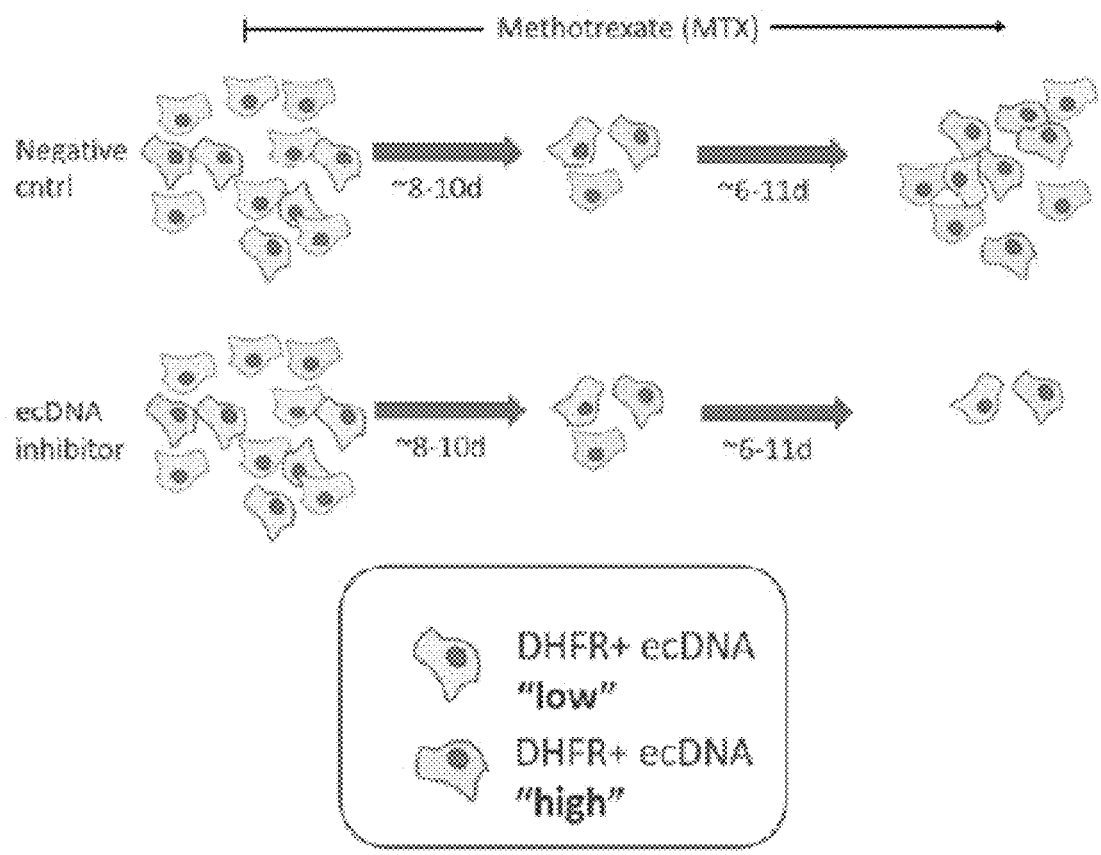
FIG. 6 shows HeLa methotrexate-resistant (MTX-R) ecDNA in a model assay.
Figure 6:
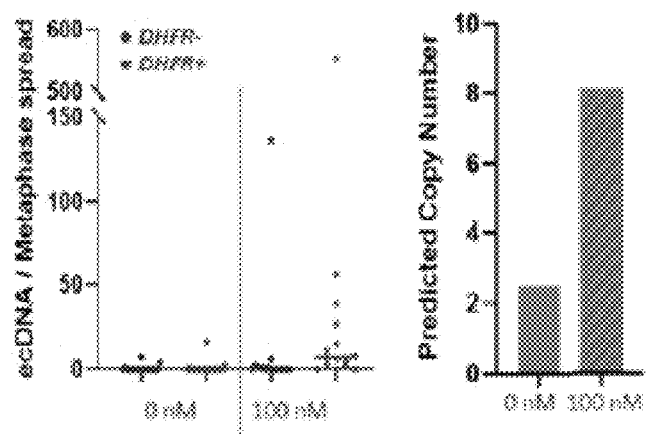
Figure 7:
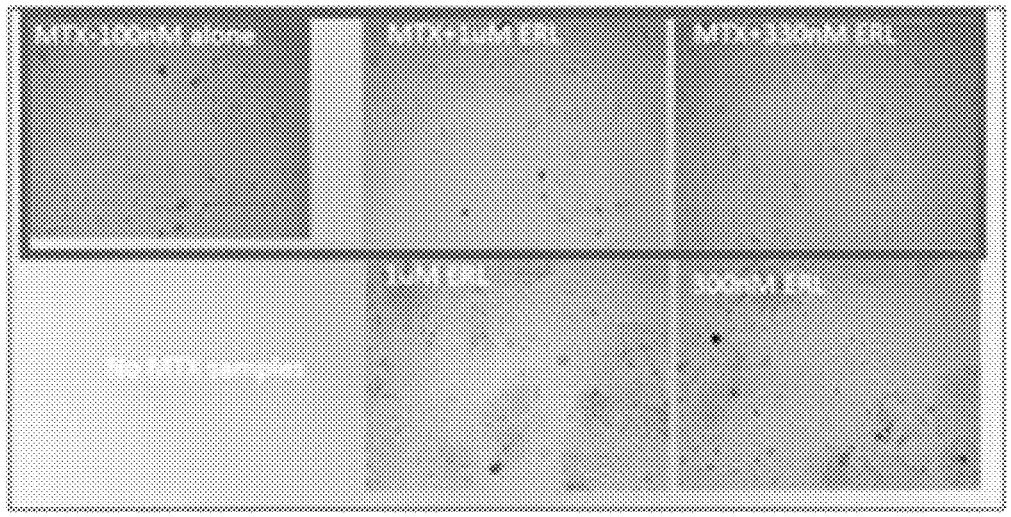
FIG. 7 shows CHK1 target validation in HeLa MTX-R model.
Figure 7:
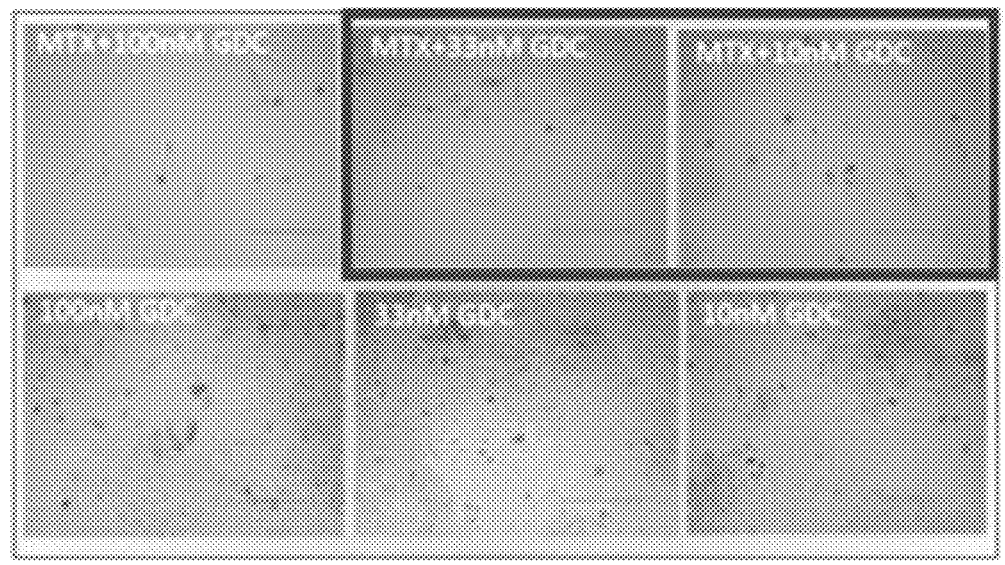
Figure 7:
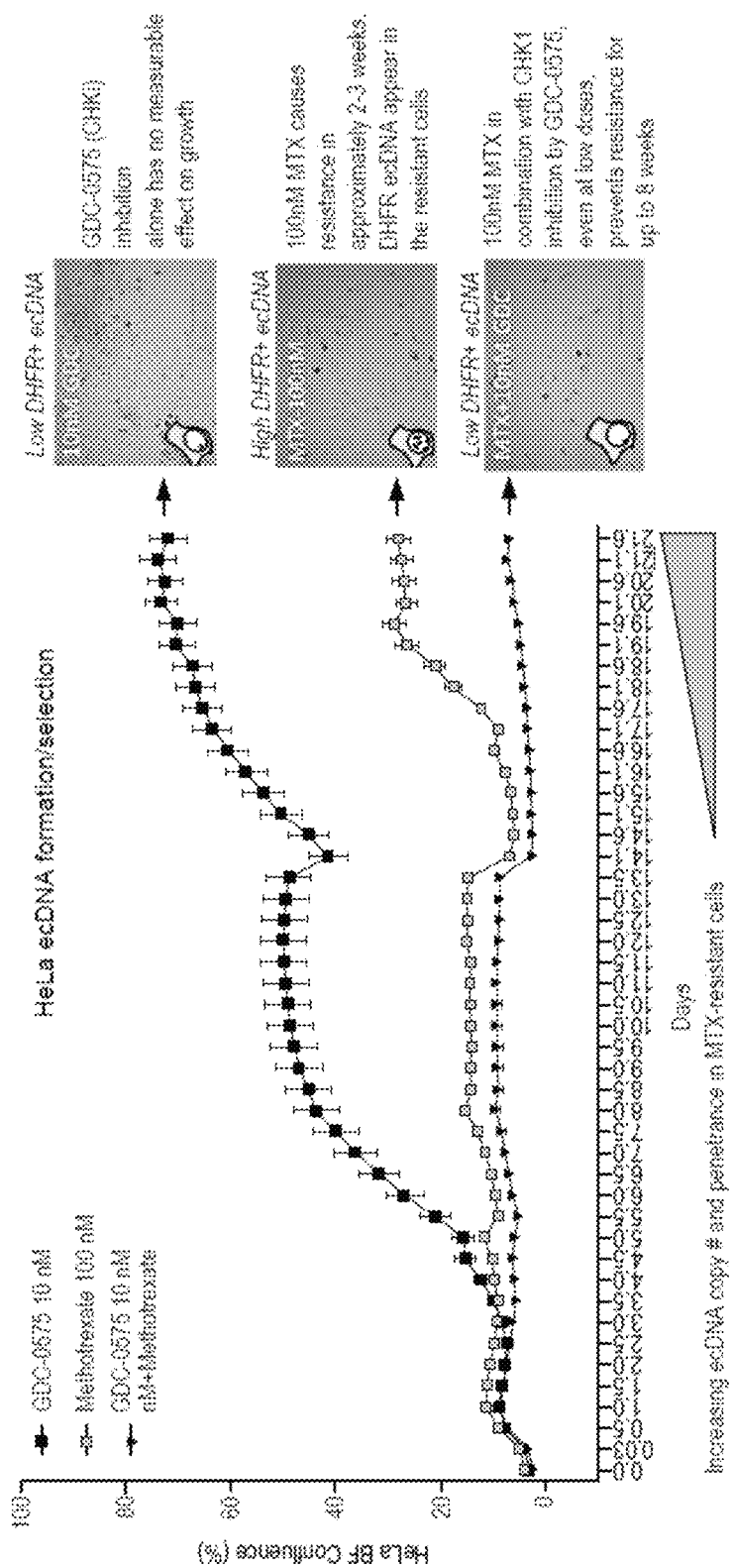
Figure 9:
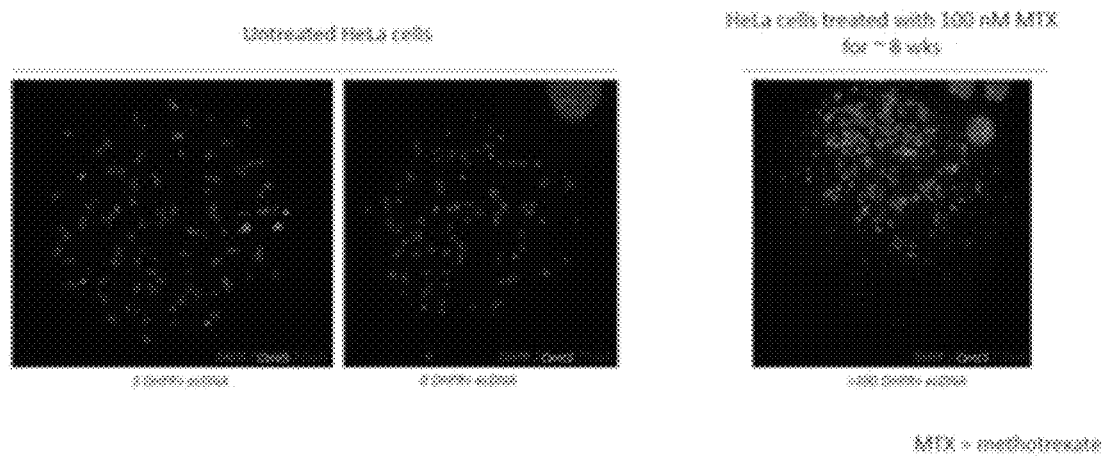
FIG. 9 shows fluorescence in situ hybridization (FISH) images of parental HeLa cells (left panels) MTX-R HeLa cells (right panel).

HeLa cells were treated with CHK1 inhibitor 10 nM GDC-0575 alone, with 100 nM methotrexate alone, or with a combination of the 10 nM GDC-0575 and 100 nM methotrexate over the course of three weeks. Cell confluence was measured via high-content microscopy over the time course. GDC-0575 had no effect on cell growth. Methotrexate initially resulted in little to no cell growth, but after two weeks in culture, the cells began to develop resistance and cell growth resumed. In contrast, the combination with the CHK1 inhibitor prevented development of methotrexate resistance. This effect lasted until termination of the study at eight weeks. FIG. 6 shows data related to ecDNA-positive methotrexate-resistant HeLa cancer cells. An RNR inhibitor abrogates rapid ecDNA-mediated resistance to methotrexate treatment, resulting in observed synthetic lethality. FIG. 9 shows FISH images of parental HeLa cells (left panels) and methotrexate-resistant HeLa cells (right panel). This data shows that the untreated HeLa cells have very few ecDNA-positive cells. In contrast, the methotrexate-resistant HeLa cells have increased levels of ecDNA. Preliminary CHK1 target validation in methotrexate-resistant HeLa cells is shown in FIG. 7. This data shows live cell microscopy suggests potential synthetic lethality with CHK1 inhibition in the formation of methotrexate resistance, via DHFR amplification, on ecDNA in HeLa cells.

Figure 27:
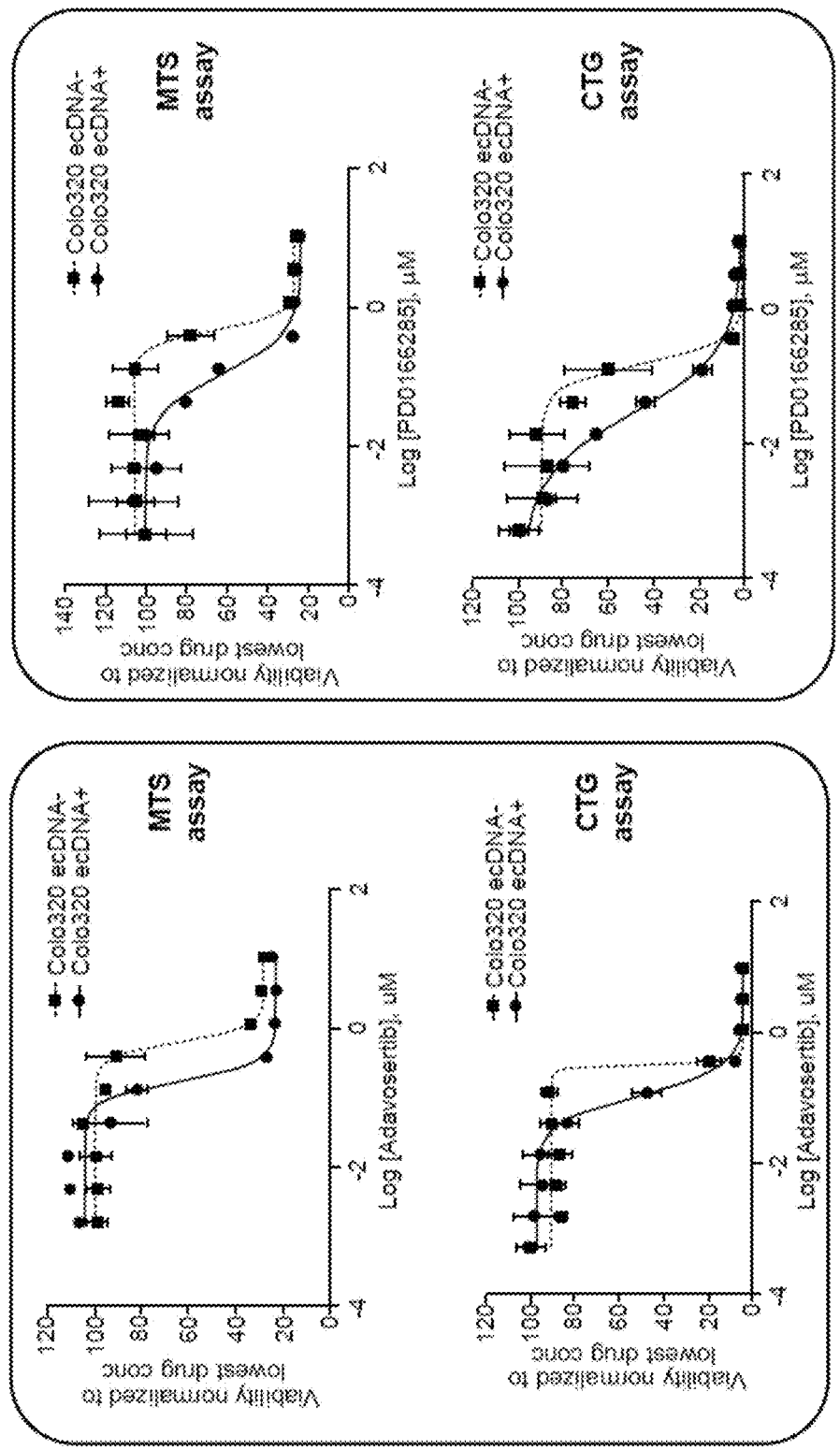
FIG. 27 shows sensitivity of ecDNA+ and ecDNA− cell lines to WEE1 inhibition.

Sensitivity of an ecDNA+ (Colo320 ecDNA+) and an ecDNA− (Colo320 ecDNA−) cell line models to WEE1 inhibition was determined by treating each with increasing concentrations of either adavosertib or PD0166285 over a 7 day period. Cell proliferation was determined using a MTS assay (FIG. 27, top panels), while viability was determined using CellTiter-glo assay (FIG. 27 bottom panels). Colo320 ecDNA+ cells compared with Colo320 ecDNA− cells showed enhanced sensitivity to the treatment with adavosertib and PD0166285 when analyzing proliferation and viability changes.

Figure 36:
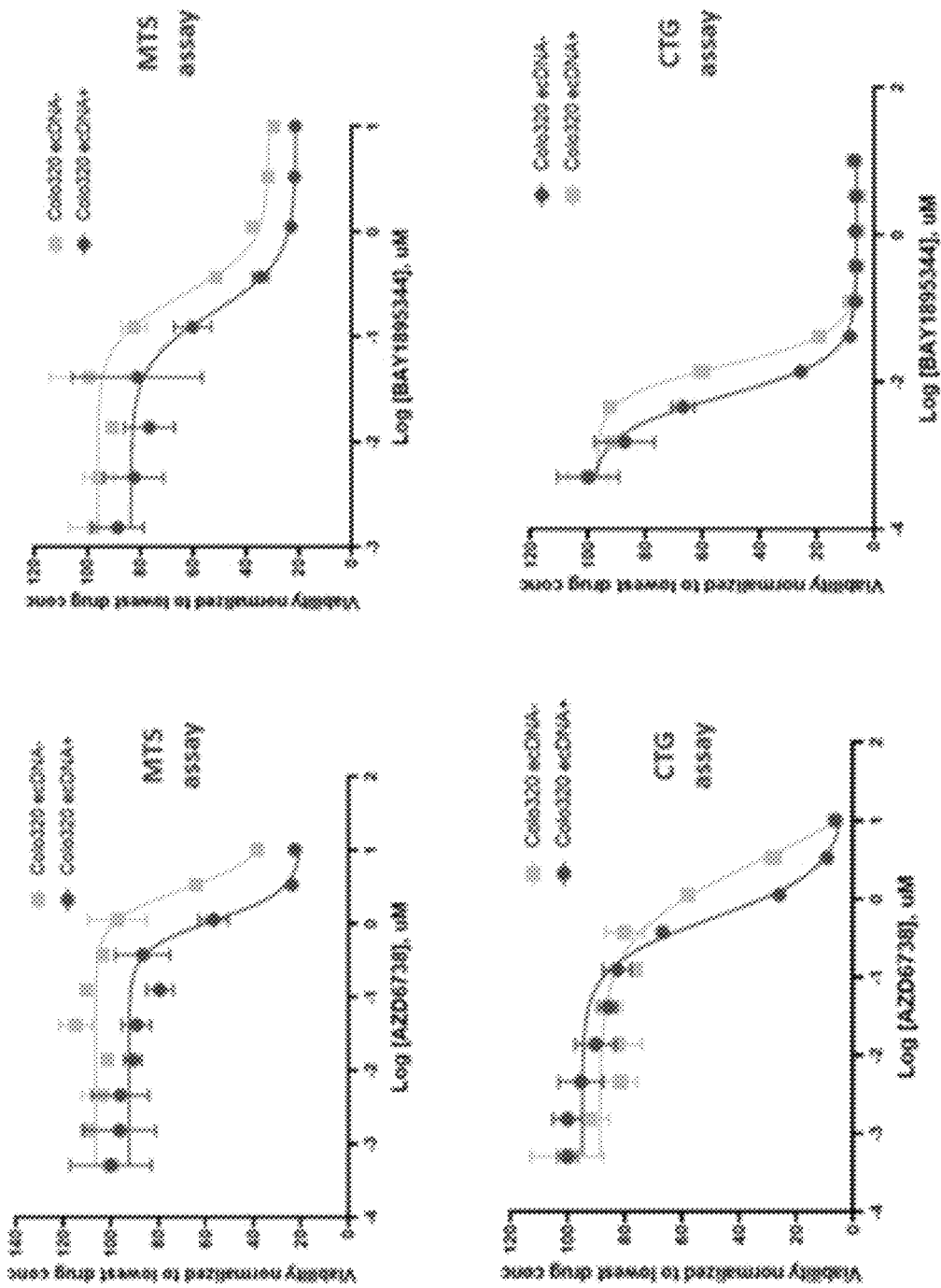
FIG. 36 shows sensitivity of ecDNA+ and ecDNA− cell lines to ATR inhibition.

Sensitivity of an ecDNA+ (Colo320 ecDNA+) and an ecDNA− (Colo320 ecDNA−) cell line models to ATR inhibition was determined by treating each with increasing concentrations of either AZD6738 or BAY1895344 over a 7 day period. Cell proliferation was determined using a MTS assay (FIG. 36, top panels), while viability was determined using CellTiter-glo assay (FIG. 36, bottom panels). Colo320 ecDNA+ cells compared with Colo320 ecDNA− cells showed enhanced sensitivity to the treatment with AZD6738 and BAY1895344 when analyzing proliferation and viability changes compared.

Figure 28:
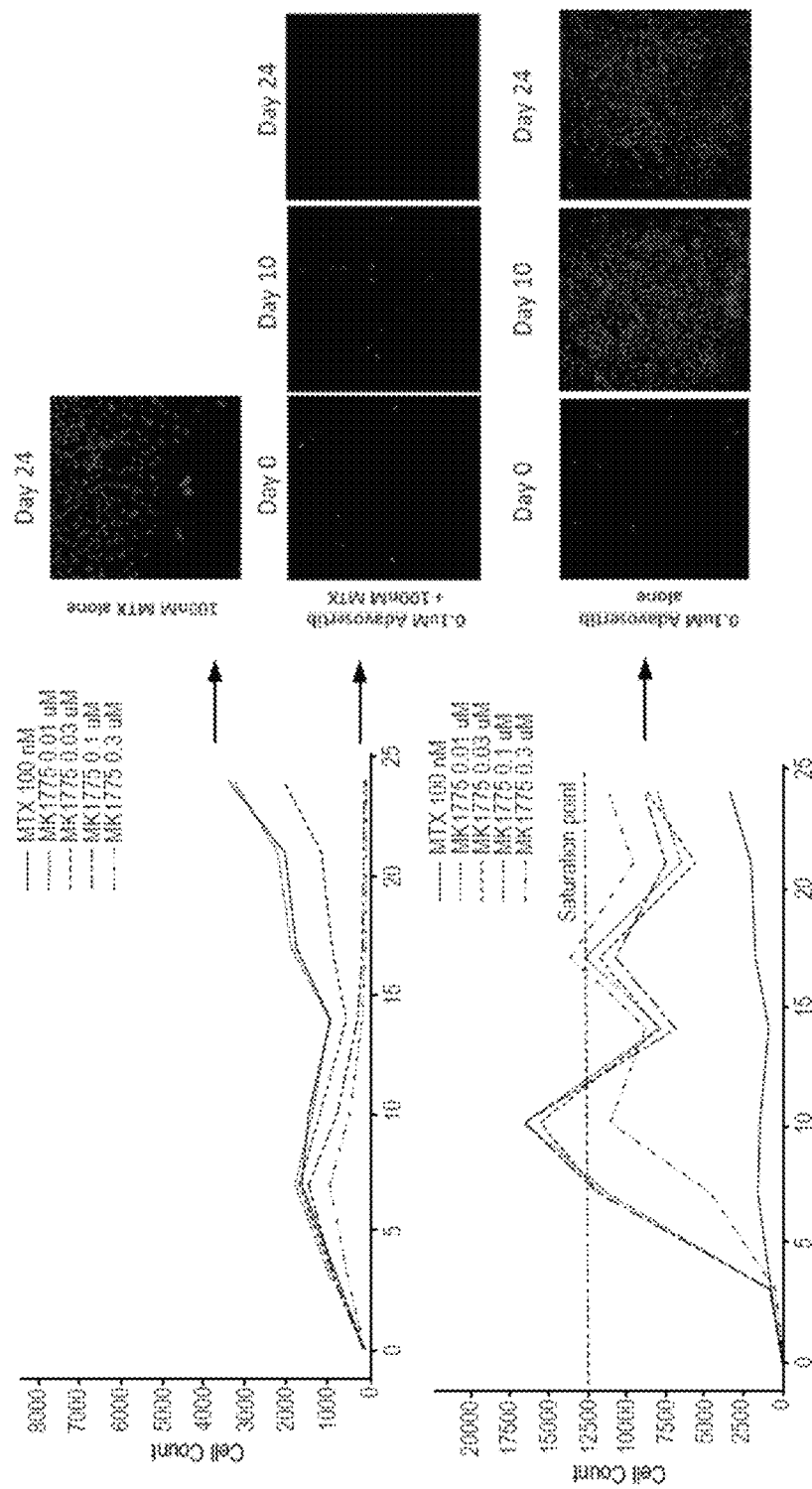
FIG. 28 shows adavosertib abrogation of methotrexate resistance in ecDNA+ cells.
Figure 29:
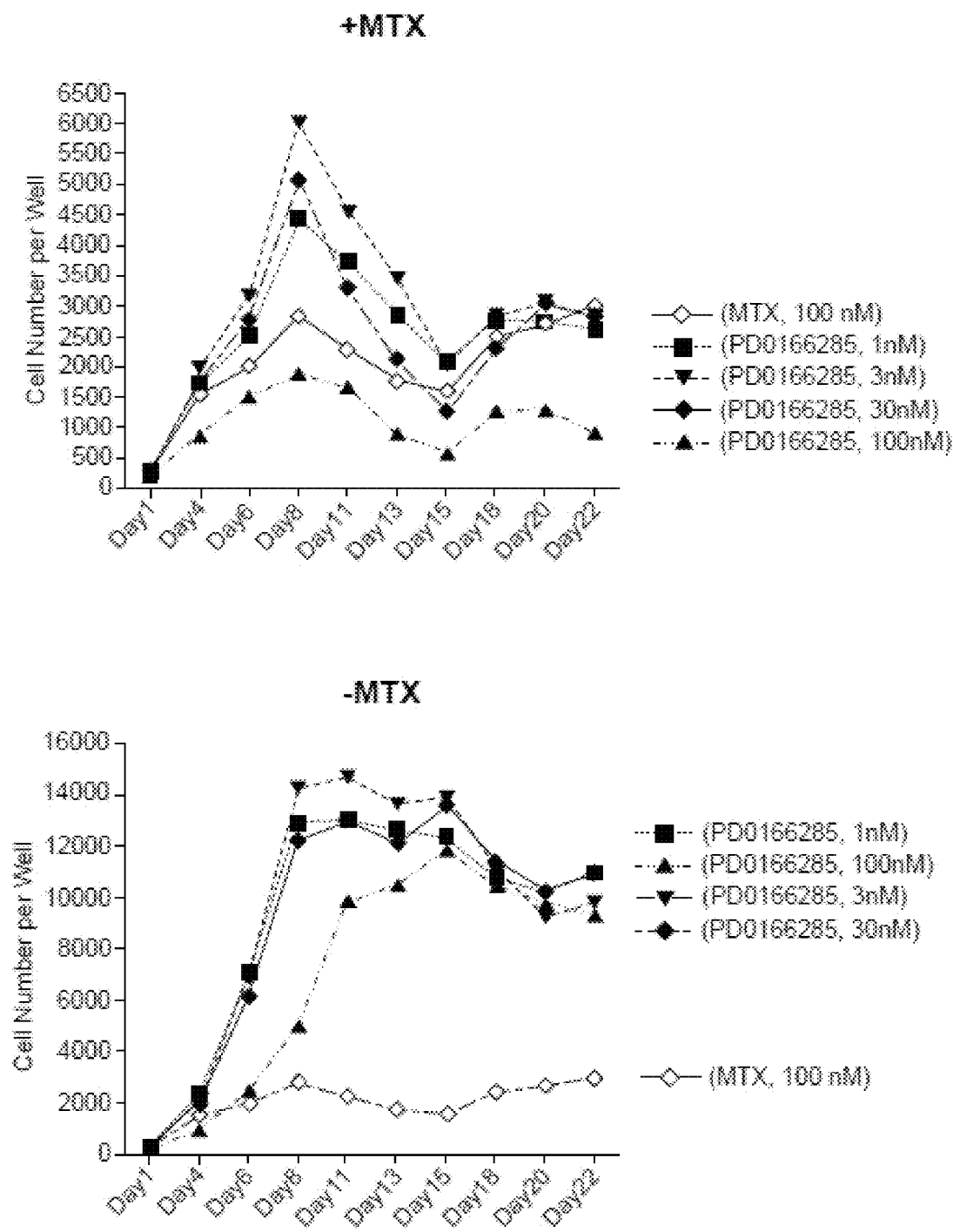
FIG. 29 shows PD1066285 abrogation of methotrexate resistance in ecDNA+ cells.

HeLa cells were treated with a WEE1 inhibitor, 0.01-0.3 µM adavosertib alone, with 1 nM-100 nM PD0166285, with 100 nM methotrexate alone, or with a combination of 0.01-0.3 µM adavosertib and 100 nM methotrexate or a combination of 1 nM-100 nM PD0166285 and 100 nM methotrexate over the course of three weeks. Cell confluence was measured via high-content microscopy over the time course. Methotrexate initially resulted in little to no cell growth, but after two weeks in culture, the cells began to develop resistance and cell growth resumed. In contrast, the combination with adavosertib prevented development of methotrexate resistance. FIG. 28 shows data related to adavosertib (MK1775) abrogation of methotrexate resistance in ecDNA-positive methotrexate resistant HeLa cancer cells as measured by NucRed. FIG. 29 shows data related to PD0166285 abrogation of methotrexate resistance in ecDNA-positive methotrexate resistant HeLa cancer cells.

Figure 35:
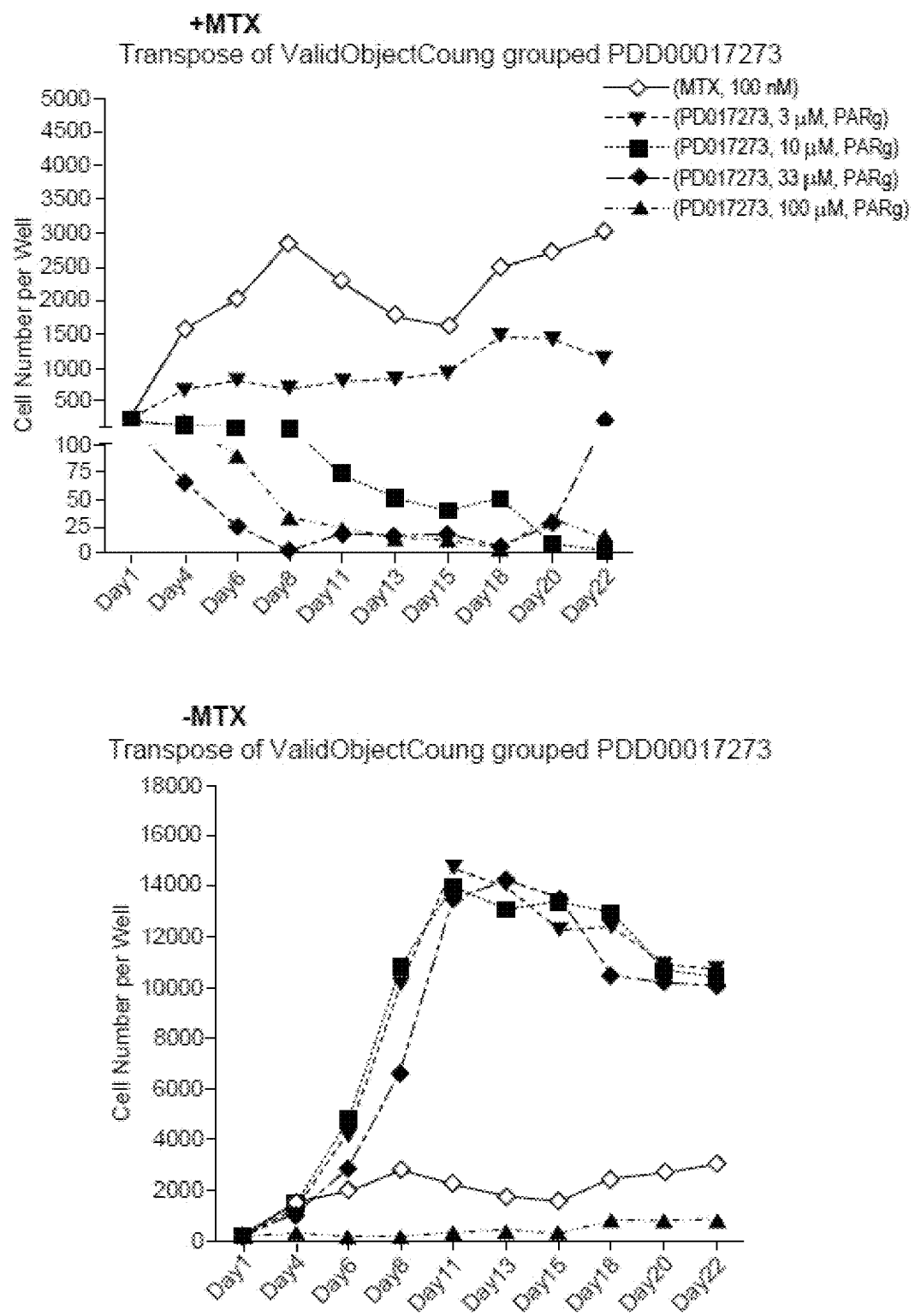
FIG. 35 PARG inhibition prevents methotrexate resistance.

HeLa cells were treated with a PARG inhibitor, 3-100 µM PD00017273 with (FIG. 35 top panel) or without (FIG. 35 bottom panel) 100 nM methotrexate over the course of 3 weeks. Cell confluence was measured via high-content microscopy over the time course. Methotrexate initially resulted in little to no cell growth, but after two weeks in culture, the cells began to develop resistance and cell growth resumed. In contrast, the combination with PD00017273 prevented development of methotrexate resistance.

Figure 8:
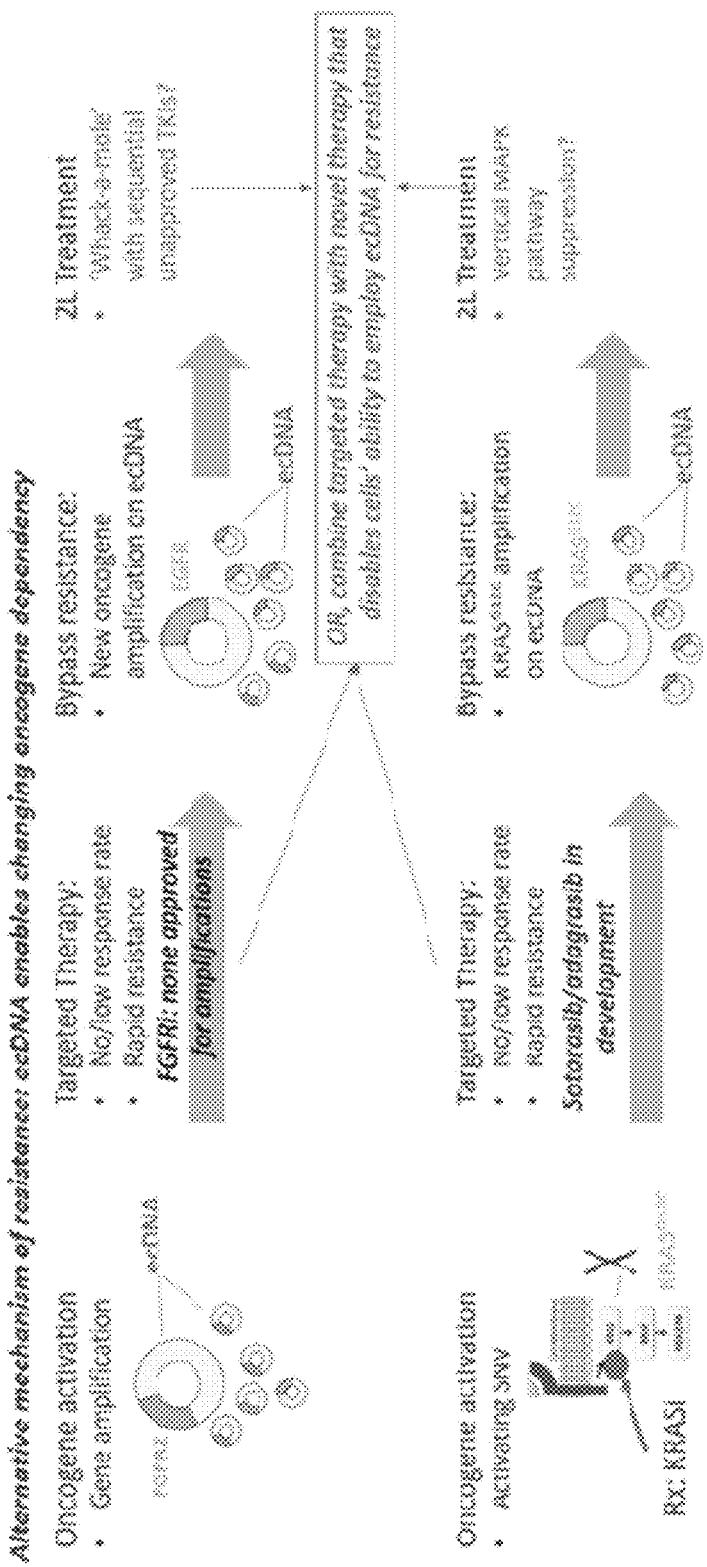
FIG. 8 shows ecDNA mediates an important and clinically distinct mechanism of resistance to targeted therapies.
Figure 37:
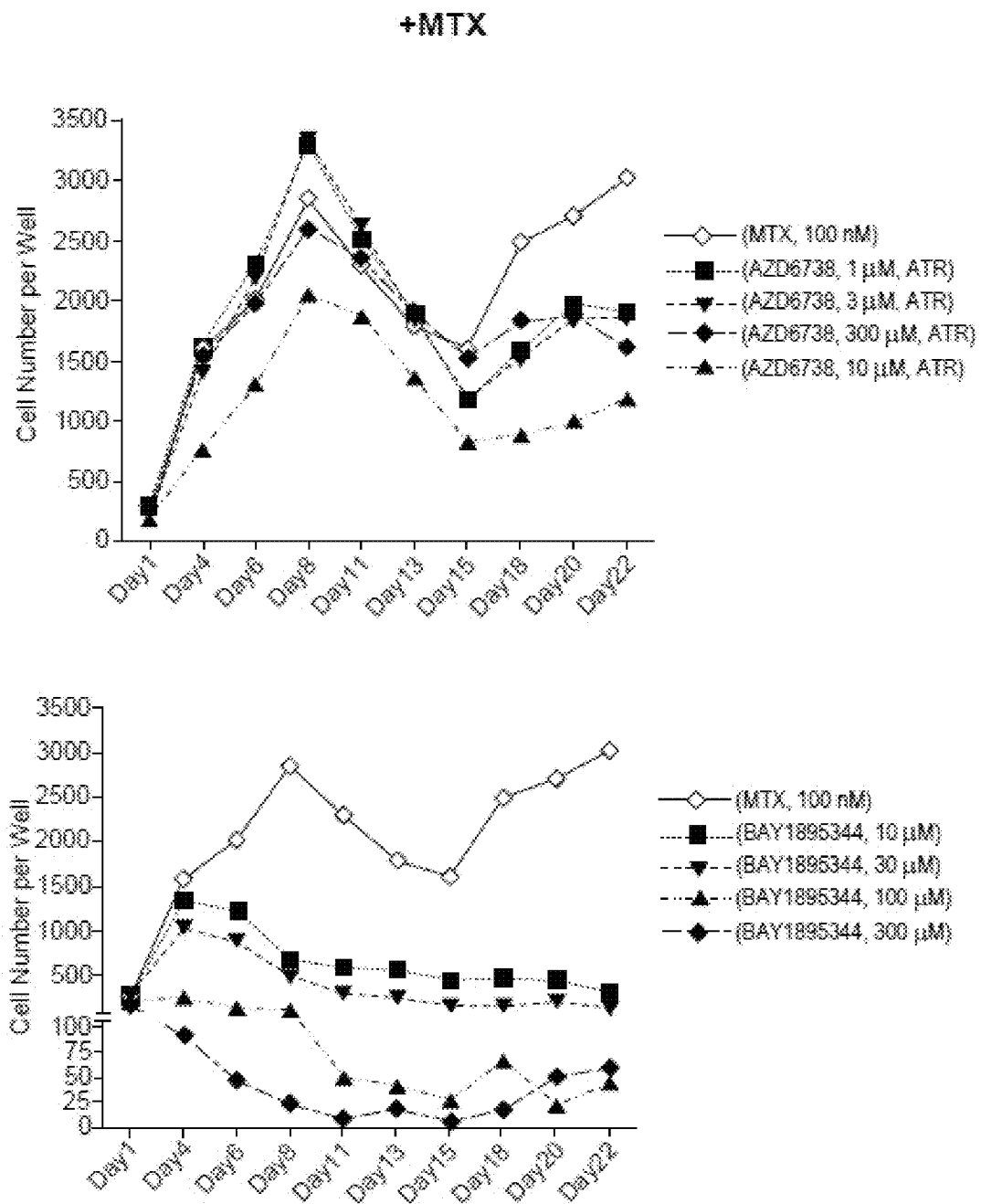
FIG. 37 shows ATR inhibition prevents methotrexate resistance.
Figure 37:
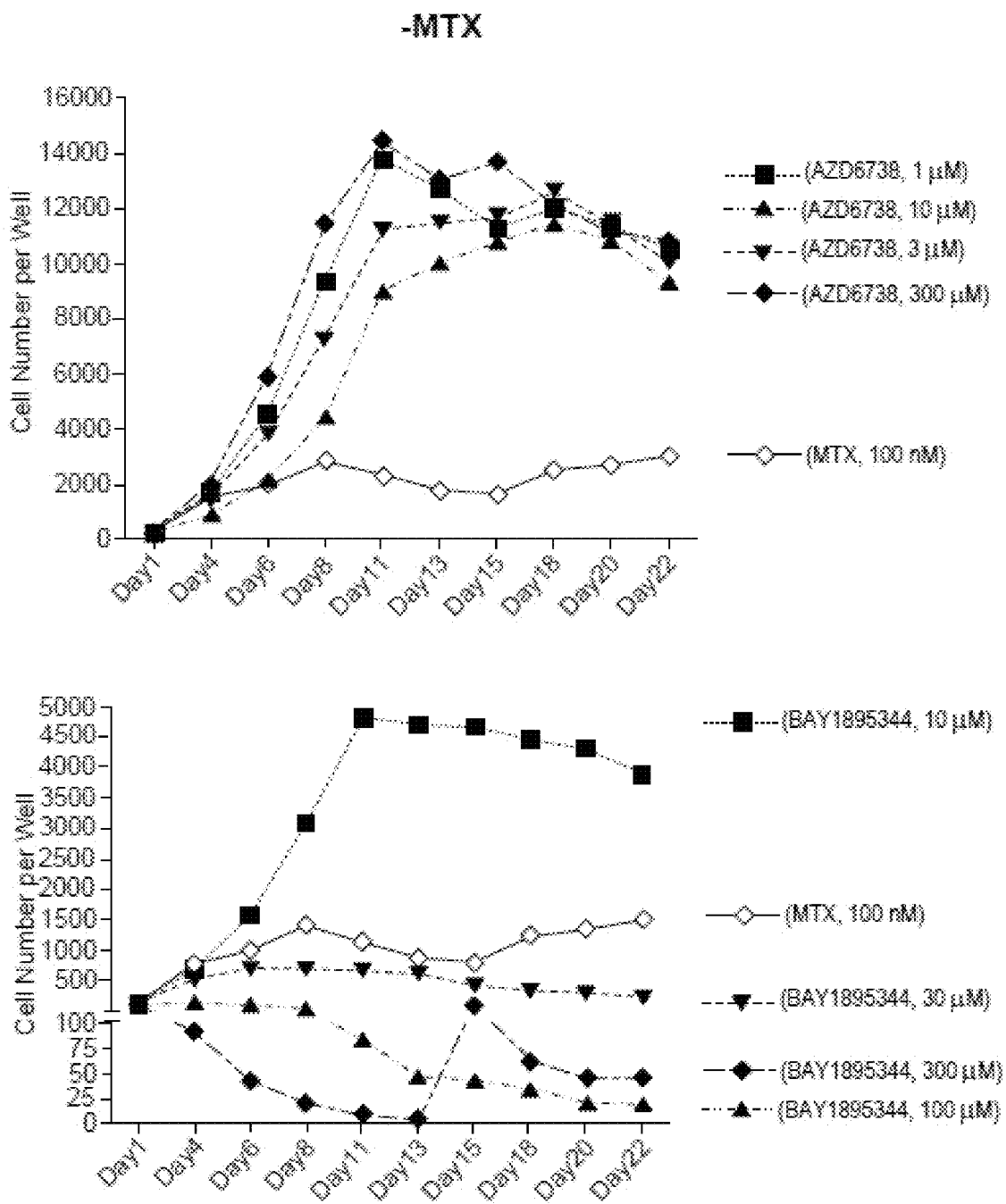

HeLa cells were treated with ATR inhibitors 300 nM-10 µM AZD6738 or 10-300 nM BAY1895344 with (FIG. 37, top panels) or without (FIG. 37, bottom panels) 100 nM methotrexate over the course of 3 weeks. Cell confluence was measured via high-content microscopy over the time course. AZD6738 showed synthetic lethality with 100 nM methotrexate but on its own, AZD6738 did not affect HeLa cell growth. However. BAY1895344 showed toxicity on its own above 10 nM.

ecDNA mediates an important and clinically distinct mechanism of resistance to targeted therapies. A model for this is shown in FIG. 8. This data suggests that there are immediate opportunities for utility of ecDNA-directed therapies, such as the use of one more RS-pathway targeting agents, including but not limited to those targeting RNR, ATR, CHK1 and WEE1, as a single agent or in combination with other therapies. First, tumors with non-mutant amplified oncogenes for which there are no approved targeted therapies (e.g. FGFR, EGFR, MET, KRAS, MDM2 amplifications). Second, tumors treated with one or more targeted agents where acquired resistance of the cancer develops when using the one or more targeted agents that directly inhibit activating mutant forms of certain oncoproteins (e.g. KRAS. BRAF, EGFR) as a consequence of focal amplification such as ecDNA-based amplification of the target gene itself.

Example 2: Routes to Resistance in ecDNA-Positive Cancer

In order to understand the mechanism of emergence of resistance to therapy mediated by ecDNA, it was determined whether resistant clones harboring ecDNA were pre-existing or if they were formed de-novo under therapy pressure. Barcoding experiments were performed in HeLa cells that become resistant to prolonged treatment with DHFR inhibitor methotrexate (MTX) through generation of ecDNA that harbors DHFR, hence overcoming MTX pressure.

Barcoding in Combination with Single Cells RNAseq Analysis.

Figure 10:
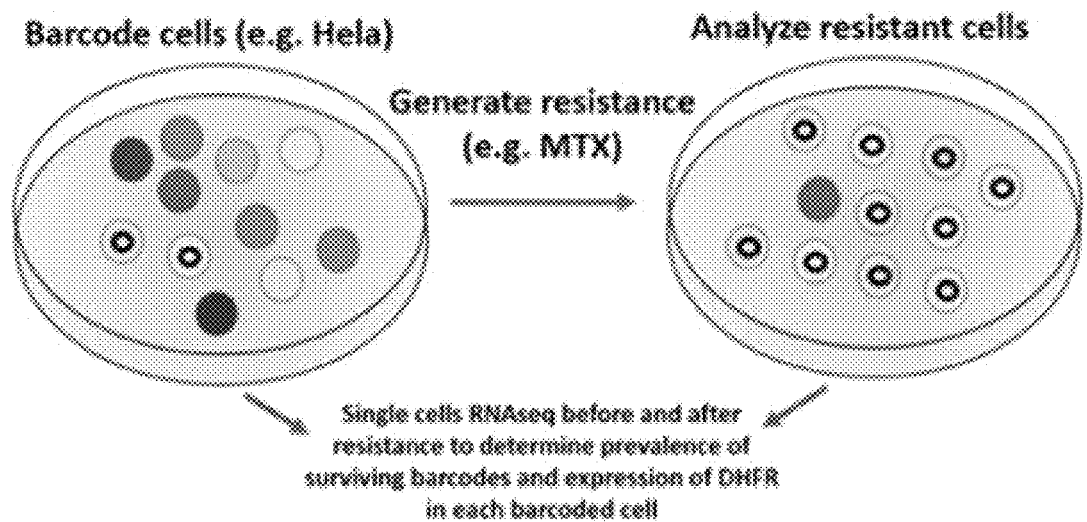
FIG. 10 illustrates the study using barcoding and single cell RNAseq for elucidation of pre-existing versus de-novo ecDNA-mediated resistance mechanisms.

The initial naïve population of cells was barcoded by stable lentiviral mediated integration of a barcode sequence into the genome of each cell. This barcode will also be expressed in the RNA of each cell. Single cell RNAseq analysis of cells will identify cells (though barcode) that harbor high expression of DHFR, indicative of presence of extra DHFR copies on ecDNA. Following several weeks of MTX pressure and generation of resistant cells, single cell RNAseq was performed again to identify the cells with barcodes that showed high DHFR expression before treatment that became resistant and survived MTX pressure. This indicates that the population of resistant cells expressing high DHFR (though extra copies on ecDNA) were pre-existing. Alternatively, the identification of cells that did not have high DHFR expression before treatment, but show high expression of DHFR following treatment indicates a de-novo generation of ecDNA (FIG. 10).

Barcoding with Parallel Resistance Replicates.

Figure 11:
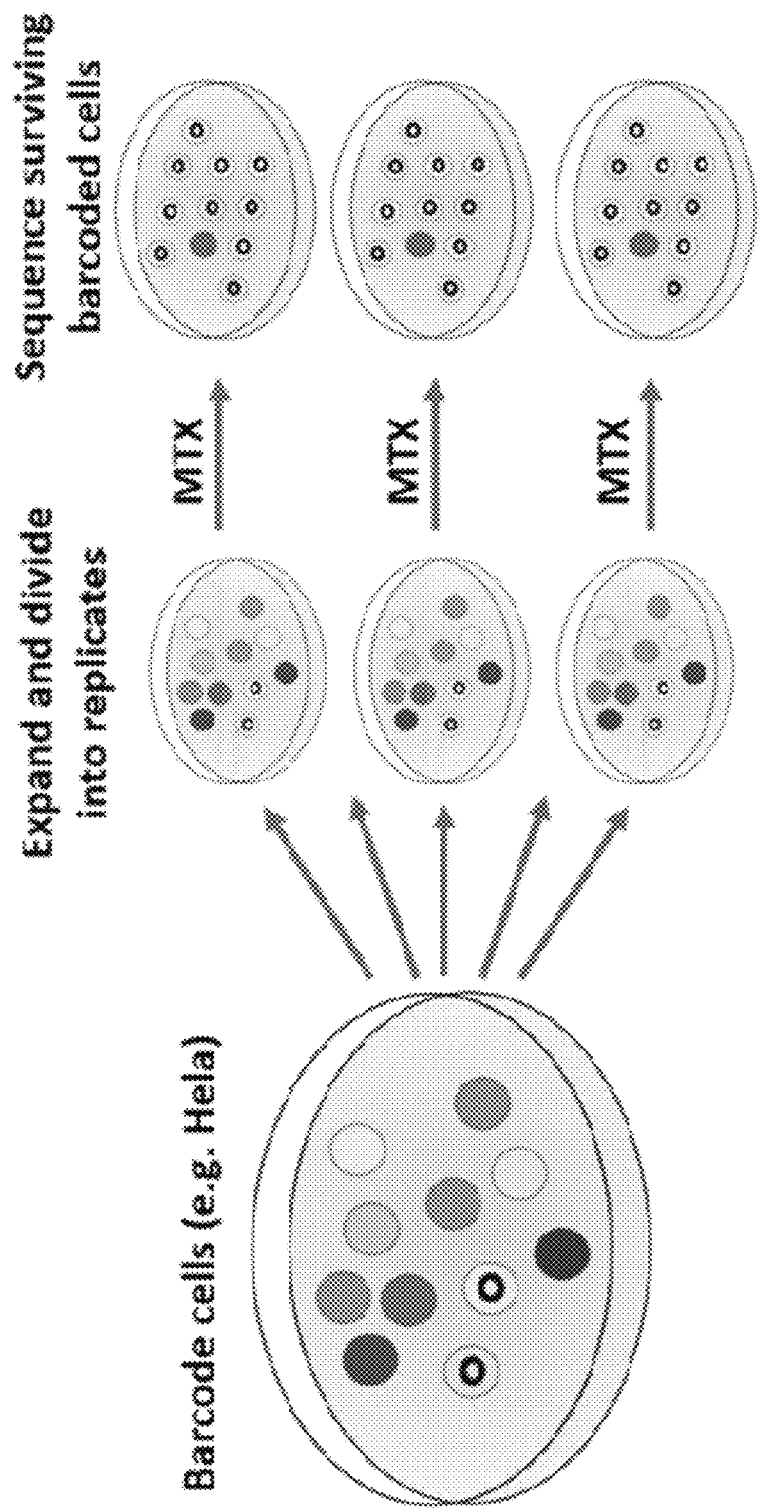
FIG. 11 illustrates the study using barcoding with replicate populations that develop methotrexate resistance to elucidate pre-existing versus de-novo ecDNA-mediated resistance.

The initial naïve population of HeLa cells were barcoded by stable lentiviral-mediated integration of a unique barcode sequence into the genome of each cell thus generating around 200,000 uniquely barcoded Hela cells. This barcoded population of cells were expanded and divided into 8 separate resistance experiments in parallel. The cells in these parallel replicates were treated with 100 nM MTX for several weeks to generate resistant populations of cells. Then, each replicate of resistant population of cells was sequenced to determine which barcodes became resistant. Common barcodes were identified in resistant cells across replicates, thereby indicating that these cells harbored resistance before treatment due to the presence of pre-existing ecDNA. In addition, a portion of barcodes were unique to individual replicates, indicating that resistance was formed de novo. (FIG. 11).

Example 3: Treatment of KRAS Mutant Tumors in Mice

Mice were implanted with CT26WT E3 G12C KRAS mutant tumor cells. Once tumors reached an average volume of 350 mm$^3$, mice were started on one of the following therapeutic regimens using a KRAS inhibitor (adagrasib) and/or an RNR inhibitor (gemcitabine): (1) vehicle only; (2) KRASi (adagrasib) 50 mg/kg orally once per day; (3) RNR (gemcitabine) 10 mg/kg intraperitoneal every other day; (4) RNRi (gemcitabine) 120 mg/kg intraperitoneal once per week; (5) RNRi (gemcitabine) 10 mg/kg intraperitoneal every other day+KRASi (adagrasib) 50 mg/kg orally once per day; or (6) RNRi (gemcitabine) 120 mg/kg intraperitoneal once per week+KRASi (adagrasib) 50 mg/kg orally once per day.

Figure 15:
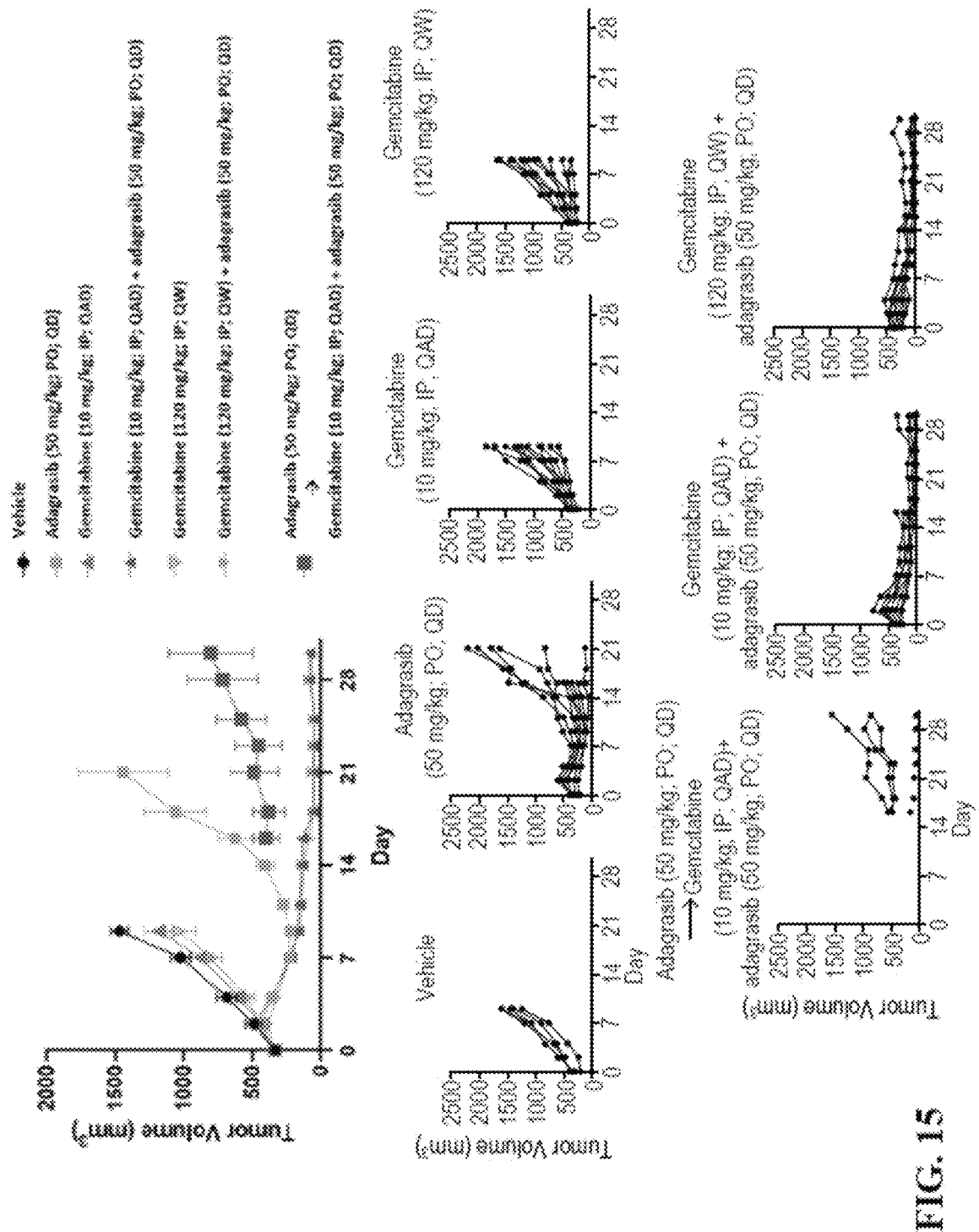
FIG. 15 shows growth of KRAS inhibitor (KRASi) resistant tumors in mice treated with various agents.
Figure 16:
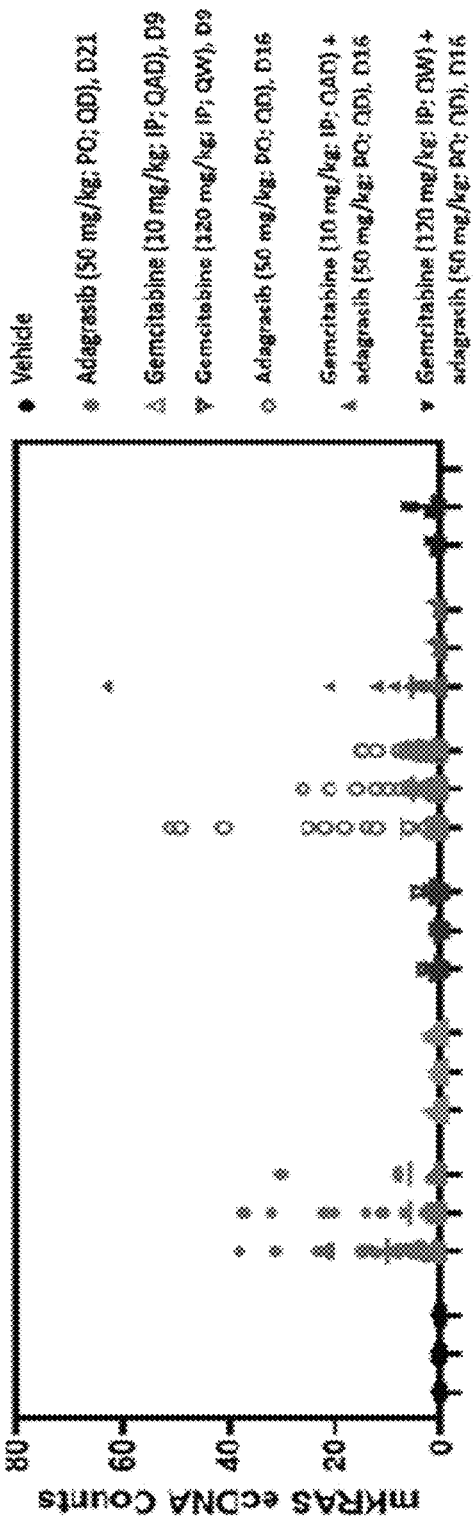
FIG. 16 shows ecDNA in tumors of mice treated with various agents.

As a single agent, only KRASi (adagrasib) resulted in a significant delay in tumor growth. However, by day 14, the tumors began to exhibit resistance to the KRASi (adagrasib) and tumor growth resumed. When the KRASi (adagrasib) was combined with the RNR inhibitor (gemcitabine), tumor growth was inhibited and continued through study day 30. To further assess the effect of combination, four mice that developed resistance on the KRASi (adagrasib) treatment were switched to treatment 5. Tumor growth in these mice was inhibited as compared to the mice that remained on the single agent treatment. Data illustrating the results of these experiments is provided in FIG. 15.

ecDNA were measured in metaphase spreads prepared from ex vivo cultures established from tumors taken from the mice on day of sacrifice. ecDNA counts were determined using FISH for murine KRAS. As shown in FIG. 16, no KRAS amplified ecDNA was seen in treatments 1 or 3. In comparison, treatments that resulted in KRASi resistance accumulated high levels of KRAS ecDNA, either at treatment group termination (D21) or on D16. KRAS ecDNA levels were significantly lower for mice treated with the combination of the KRAS inhibitor and RNR inhibitor from tumors isolated on D16.

Example 4: Treatment of KRAS Mutant Tumors in Mice

Mice were implanted with CT26WT E3 G12C KRAS mutant tumor cells. Once tumors reached an average volume of 350 mm$^3$, mice were started on one of the following therapeutic regimens using a KRAS inhibitor (adagrasib) and/or an RNR inhibitor (gemcitabine): (1) vehicle only; (2) KRASi (adagrasib) 50 mg/kg orally once per day; (3) RNRi (gemcitabine) 20 mg/kg intraperitoneal every other day; (4) RNRi (gemcitabine) 10 mg/kg intraperitoneal every other day+KRASi (adagrasib) 50 mg/kg orally once per day; or RNRi (gemcitabine) 20 mg/kg intraperitoneal every other day+KRASi (adagrasib) 50 mg/kg orally once per day.

Figure 17:
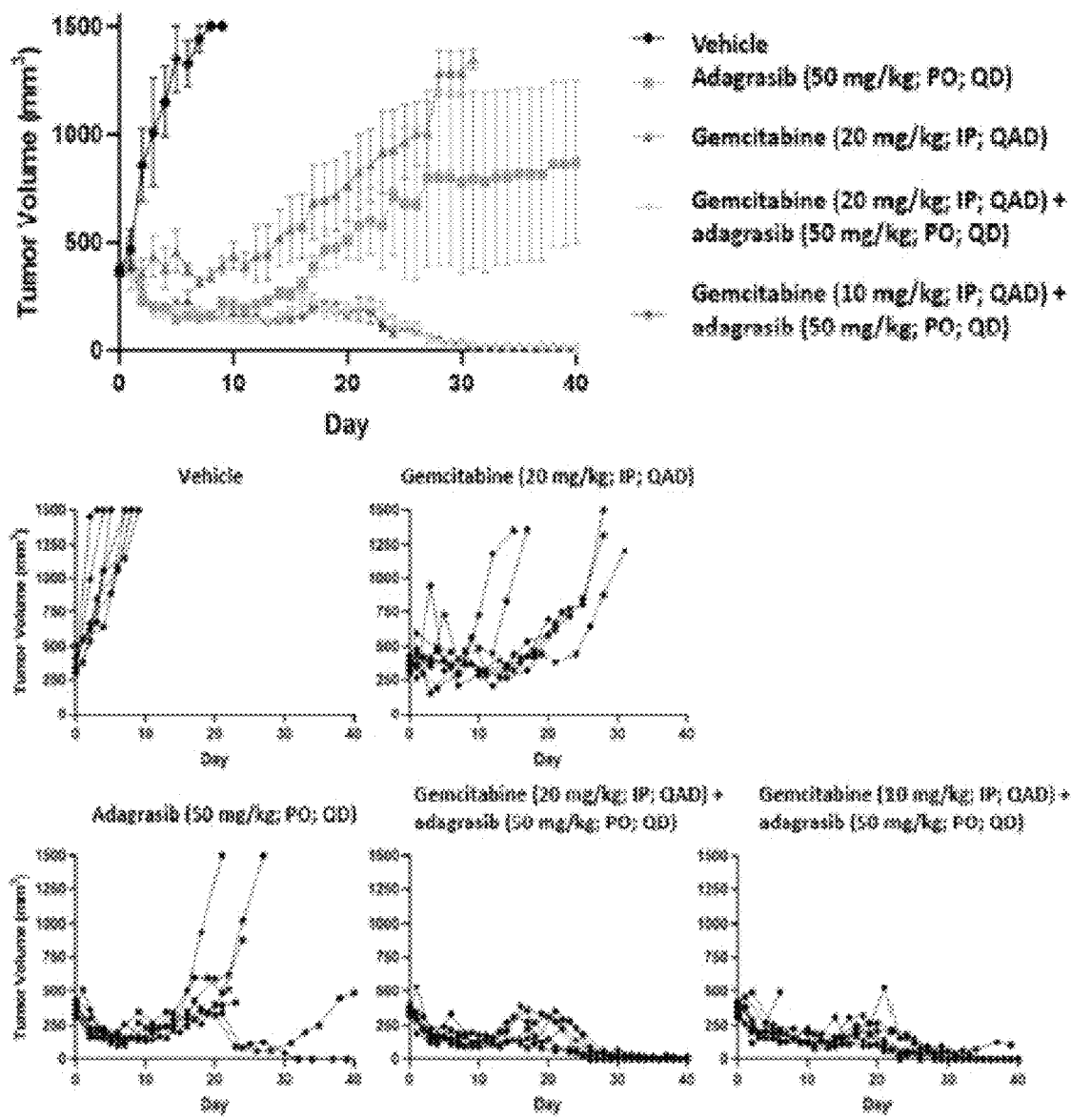
FIG. 17 shows tumor growth in mice treated with various agents.
Figure 18:
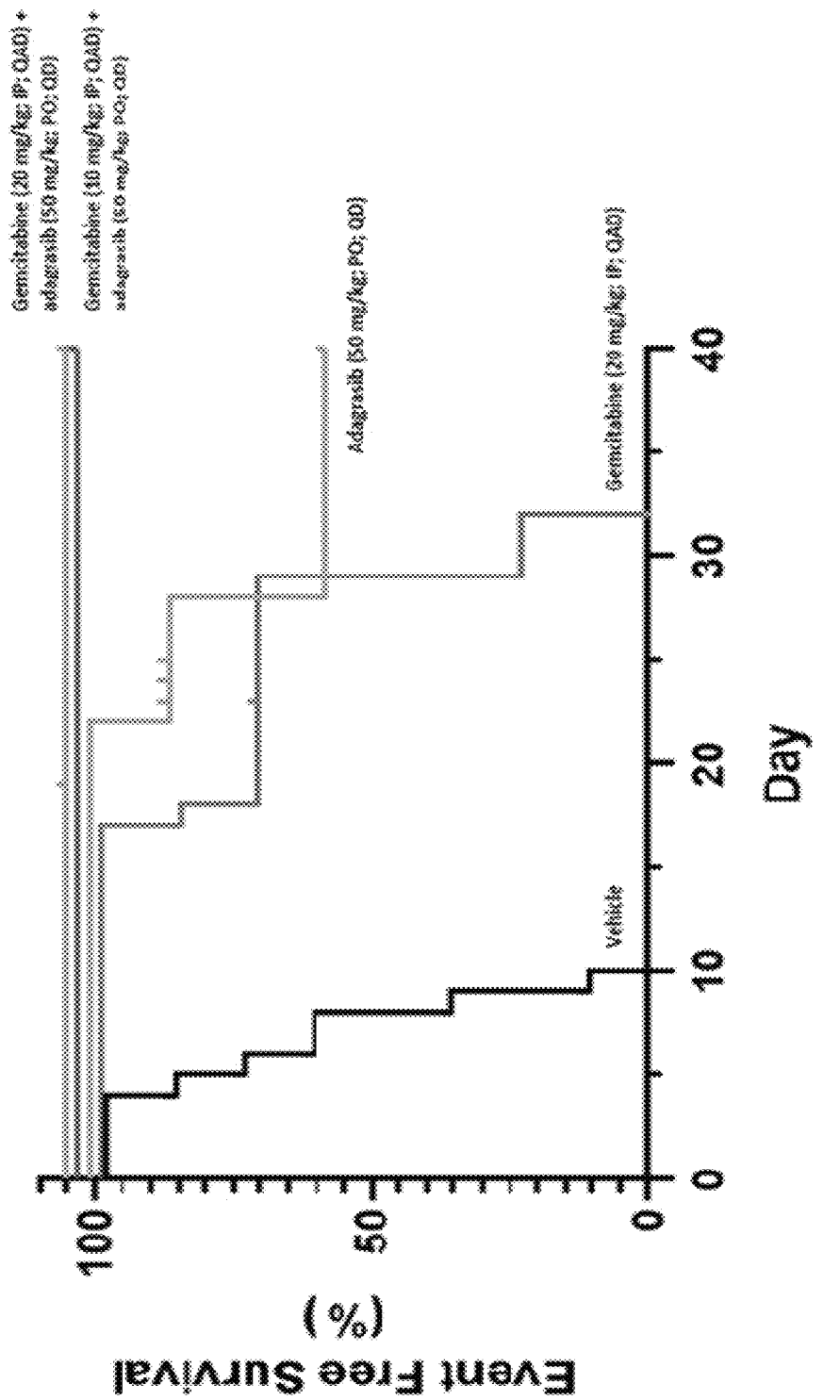
FIG. 18 shows event free survival in mice treated with various agents.

As shown in FIG. 17, substantial tumor growth was seen in treatments 1-3, with single agent KRASi (adagrasib) providing delay in tumor growth for about 2 weeks before the tumors developed resistance and tumor growth accelerated. The combination of KRASi and RNRi significantly inhibited tumor growth, reducing the tumor volume to near zero. At the lower dose of RNRi (treatment 4), 7 of 8 mice had a complete response and 7 of 7 mice had a complete response at the higher dose of RNRi (treatment 5). Survival plots for the treatments in this study are shown in FIG. 18.

Metaphase spreads were prepared from metaphase arrested and fixed ex vivo cultures established from tumors taken from mice in treatment groups and ecDNA was visualized by FISH for murine KRAS. KRAS amplified ecDNA was quantified by manual counts and/or by validated computer algorithm ecSEG (software package developed based on the methods of Rajkumar et al., Semantic Segmentation of Metaphase Images Containing Extrachromosomal DNA, iScience, Volume 21, 22 Nov. 2019, p 428-435).

Figure 19:
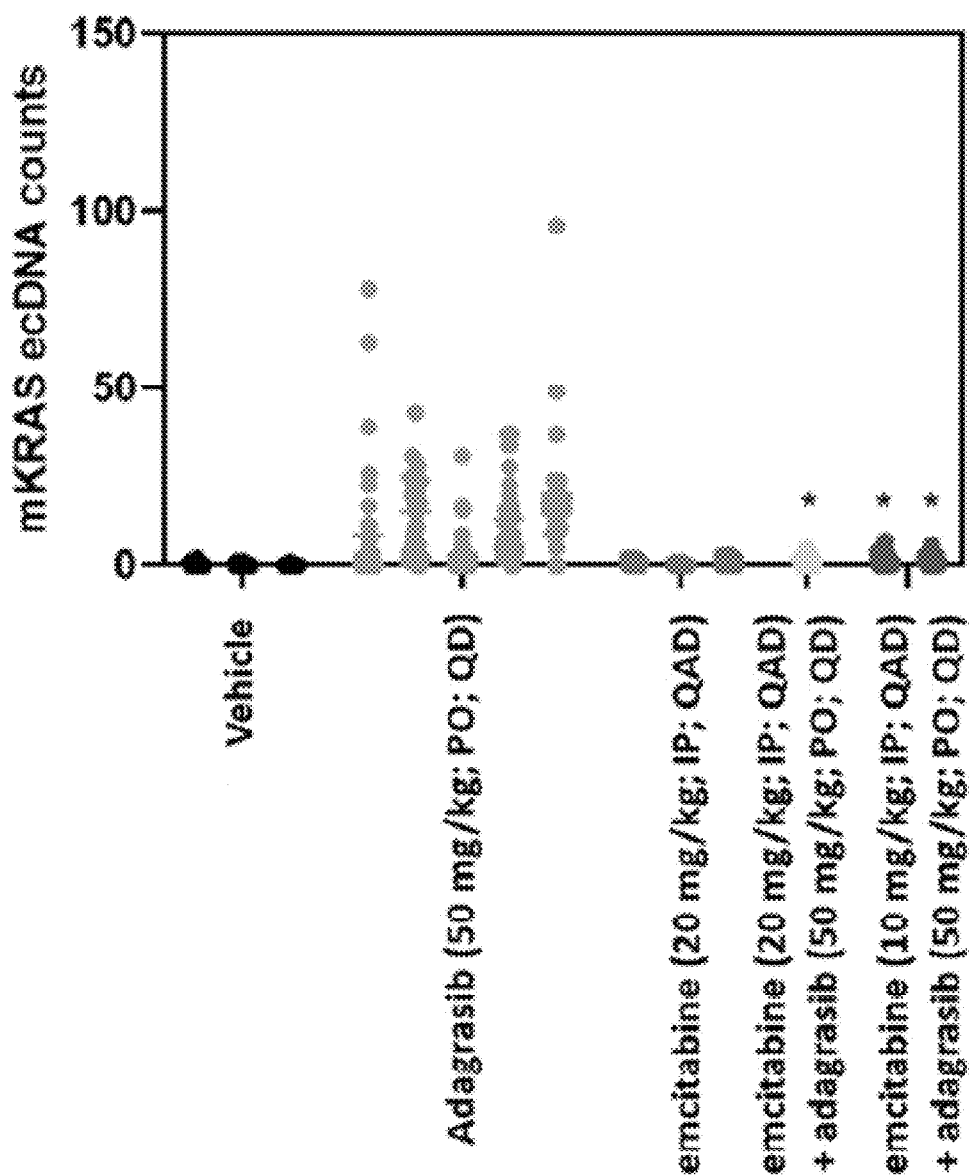
FIG. 19 shows ecDNA counts in cells from tumors in mice treated with various agents.

As shown in FIG. 19, tumors from vehicle treated and RNRi treated mice (treatment groups 1 and 3), little to know ecDNA was observed (92/100 vehicle; 78/95 RNRi). Where ecDNA were present, the copy number was low, 1-3 per metaphase spread. In contrast, KRASi treated mice (treatment group 2), samples taken from the rapidly growing tumors showed a high prevalence of ecDNA (117/161 metaphase spreads having ecDNA or ecDNA and chromosomal amplification of KRAS), with a significantly higher ecDNA count (an average of 16 KRAS ecDNA in ecDNA containing metaphase spreads). ecDNA was assessed in several mice from treatment groups 4 and 5, which were removed from treatment after day 40. As expected, very low ecDNA was present in these tumors and where ecDNA was present, the copy number was 1-7 ecDNA per metaphase spread. This data reinforces the mechanism of action of RNRi as an anti-ecDNA therapeutic.

Figure 20:
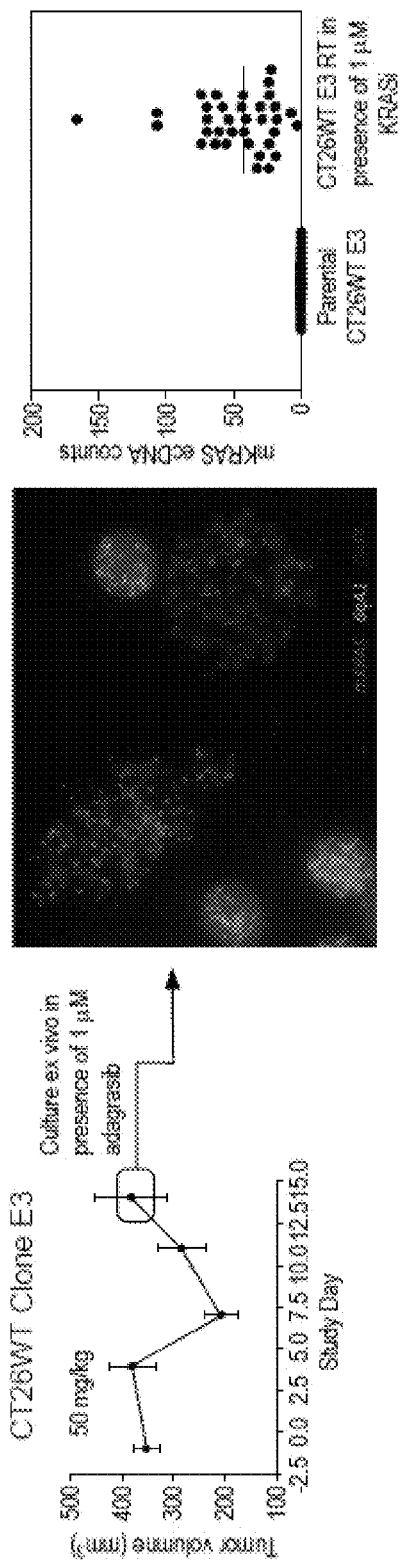
FIG. 20 shows KRAS ecDNA providing ex vivo propagation of resistant tumor cells.
Figure 20:
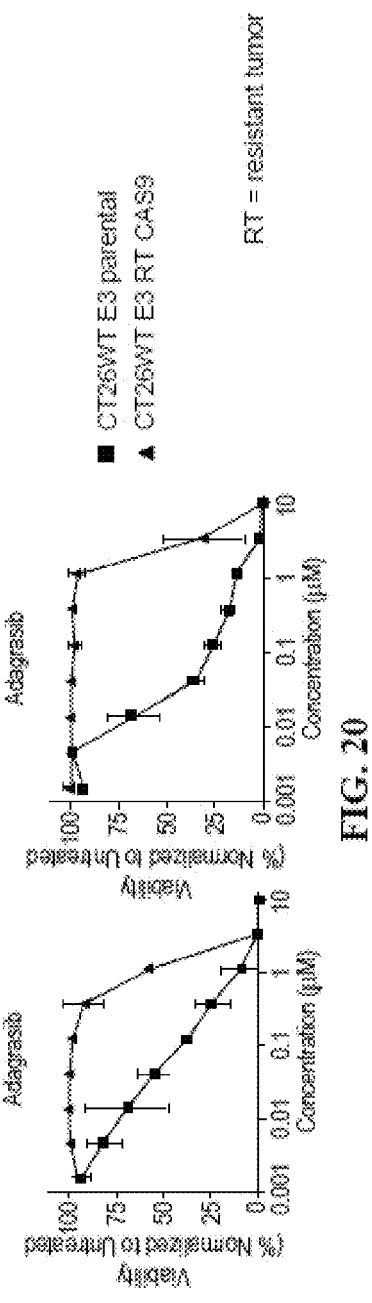

Example: 5: Ex Vivo Propagation of Resistant Tumor Cells Maintains KRAS ecDNA Providing Resistance In Vitro Cells from a CT26WT E3 G12C KRAS mutant tumor that became resistant to KRASi were propagated in vitro in the presence of 1 μM KRASi (adagrasib). The cells continued to grow in the presence of the drug, confirming drug resistance. The parental CT26 WT E3 line remained sensitive to the drug in culture. ecDNA were observed by FISH imaging and measured by manual counts and ecSEG. As shown in FIG. 20, the drug resistant cells had high-levels of ecDNA, whereas the parental line did not exhibit measurable ecDNA.

Example 6: KRASi and RNRi Inhibition of Tumor Growth In Vivo

Figure 21:
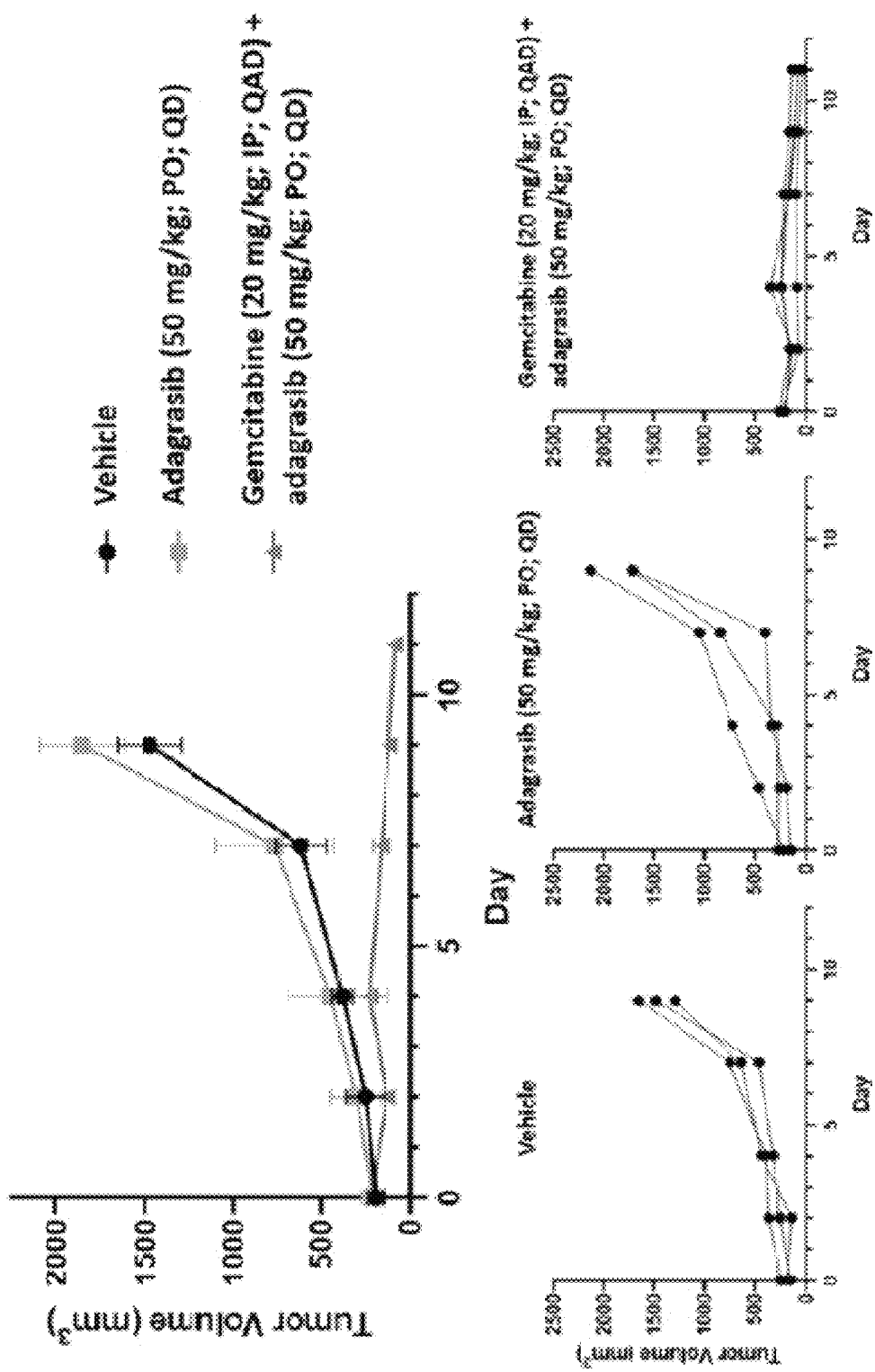
FIG. 21 shows inhibition of tumor growth in mice by the KRASi, adagrasib, and by the combination of adagrasib and the RNRi, gemcitabine.

KRASi resistant tumor cells cultured ex vivo from Example 5 were implanted into NOD-SCID mice. All mice in groups B and C were treated with KRASi (adagrasib) starting from the day of implantation. When tumors reached an average of 200 mm$^3$, the mice in group C were put onto the combination treatment. Treatment groups are as follows: (A) vehicle only; (B) KRASi (adagrasib) 50 mg/kg orally once per day; or (C) RNRi (gemcitabine) 20 mg/kg intraperitoneal every other day+KRASi (adagrasib) 50 mg/kg orally once per day. As shown in FIG. 21, the combination of KRASi and RNRi inhibited tumor growth in the animals.

Figure 22:
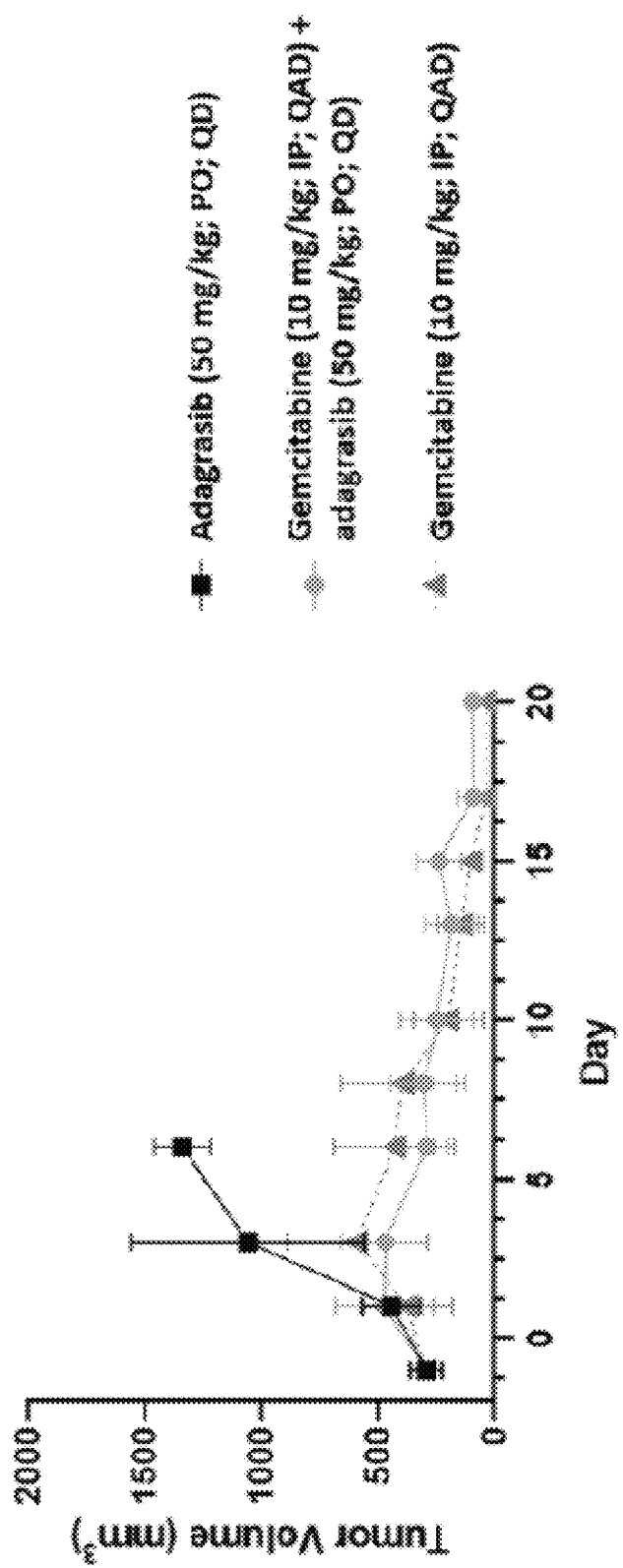
FIG. 22 shows inhibition of tumor growth in mice by RNRi, gemcitabine, and KRASi, adagrasib.

The implantation was repeated with similar conditions to test the efficacy of treatment with RNRi alone and in combination with KRASi. Mice were implanted with KRAS-resistant tumor cells as above. When the tumors reached 290 mm$^3$, mice were treated the following day as follows: (A) KRASi (adagrasib) 50 mg/kg orally once per day; (B) RNRi (gemcitabine) 10 mg/kg intraperitoneal every other day; or (C) RNRi (gemcitabine) 10 mg/kg intraperitoneal every other day+KRASi (adagrasib) 50 mg/kg orally once per day. Both RNRi alone and in combination with KRASi inhibited tumor growth in mice, as shown in FIG. 22.

Figure 23:
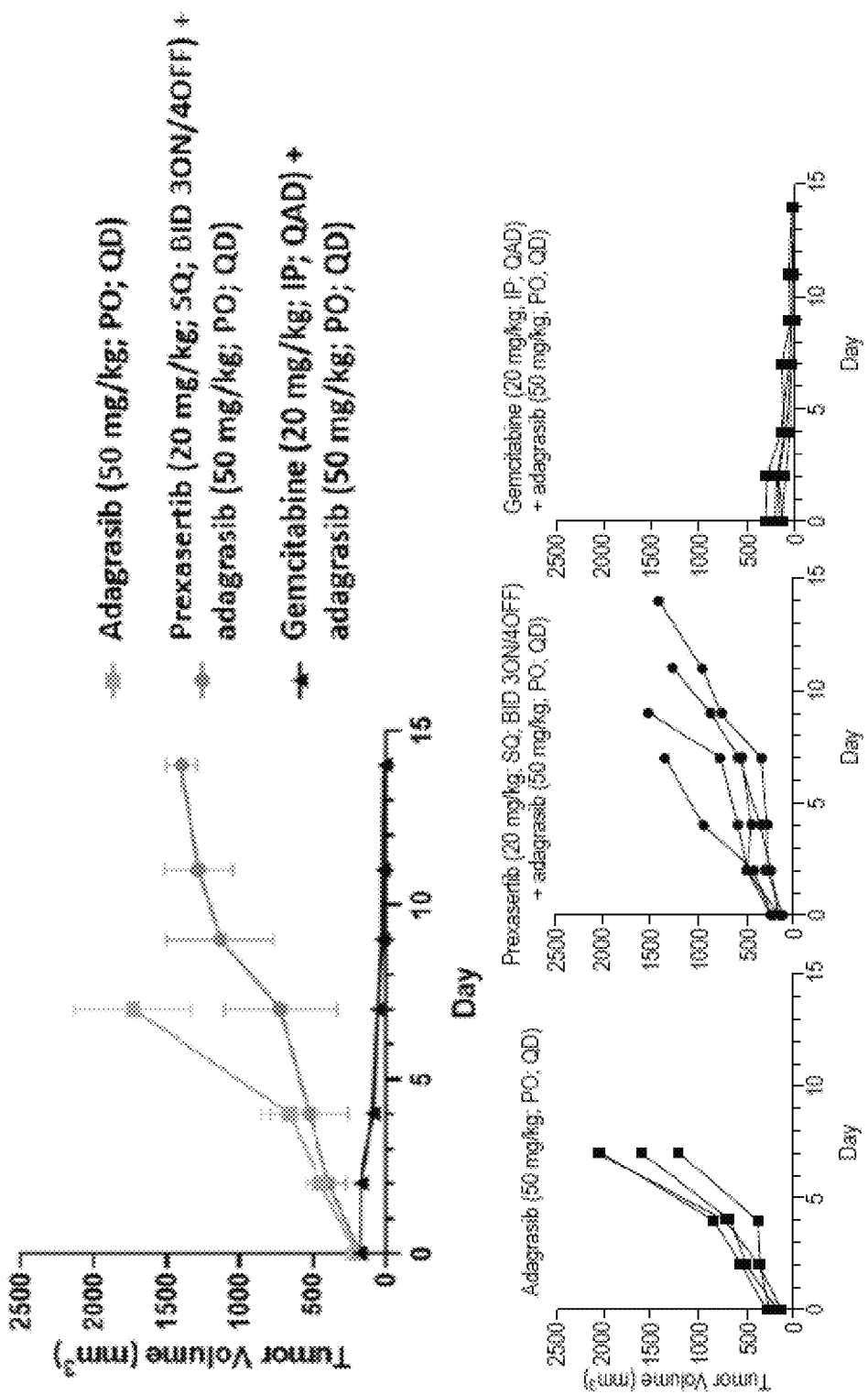
FIG. 23 shows inhibition of tumor growth in mice by RNRi, gemcitabine, and KRASi, adagrasib, and CHK1i, prexasertib.

The experiment was repeated with similar conditions to test the efficacy of treatment with CHK1i in combination with KRASi. Mice were implanted with the KRAS-resistant tumor cells as above. When the tumors reached about 180 mm$^3$, mice were treated as follows: (A) KRASi (adagrasib) 50 mg/kg orally once per day; (B) CHK1i (prexasertib) 20 mg/kg subcutaneous twice a day for three days of every 7 days; or (C) RNRi (gemcitabine) 10 mg/kg intraperitoneal every other day+KRASi (adagrasib) 50 mg/kg orally once per day. Both CHK1i and RNRi in combination with KRASi inhibited tumor growth in the mice (see FIG. 23).

Figure 45:
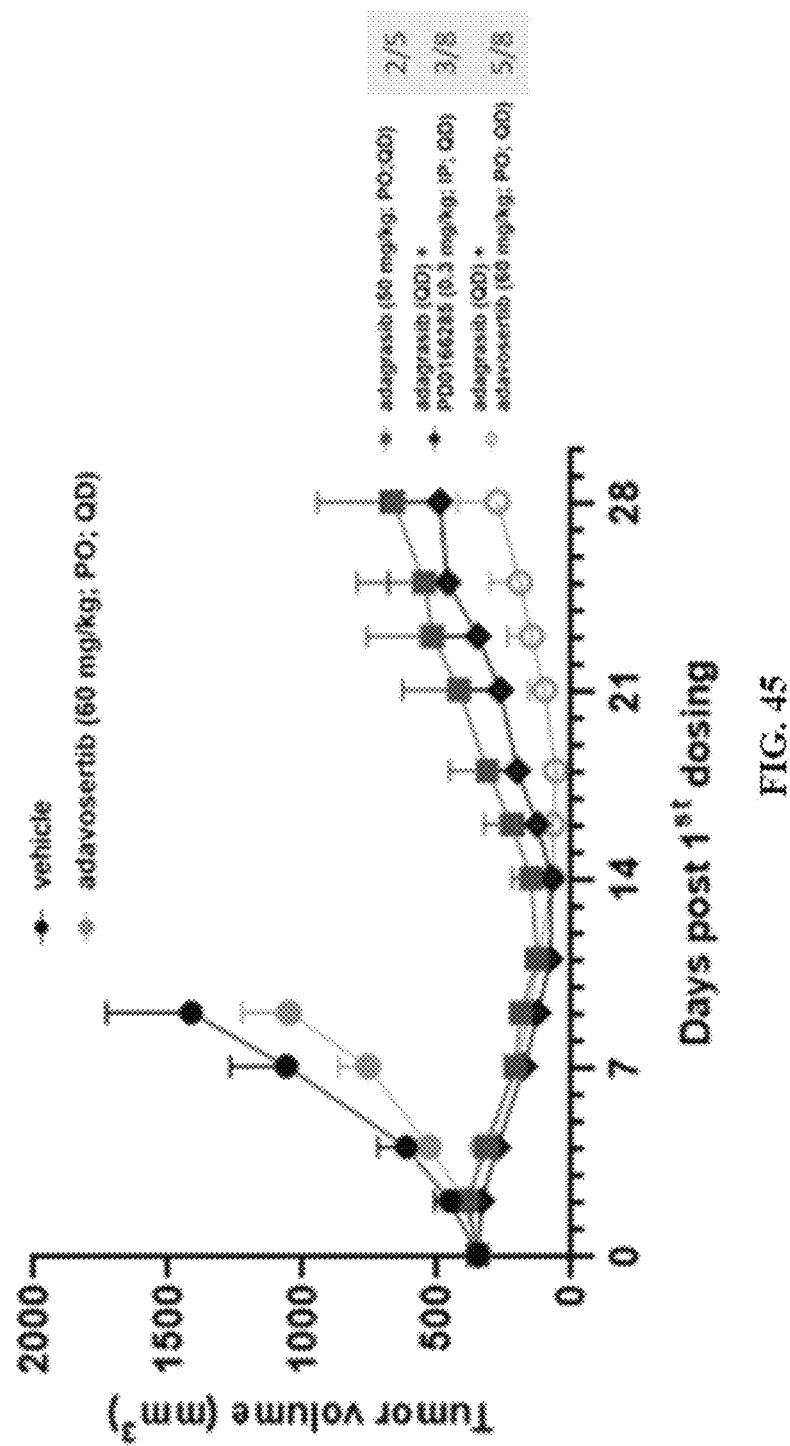
FIG. 45 shows inhibition of tumor growth in mice by WEE1i, adavosertib, or PD0166285; KRASi, adagrasib, and the combination.

The experiment was also repeated with similar conditions to test the efficacy of treatment with WEE1i in combination with KRASi. Mice were implanted with the KRAS-resistant tumor cells as above. When the tumors reached about 180 mm$^3$ mice were treated as follows: (A) KRASi (adagrasib) 50 mg/kg orally once per day, (B) WEE1i (adavosertib) 60 mg/kg orally once per day, (C) WEE1i (adavosertib) 60 mg/kg orally once per day+KRASi (adagrasib) 50 mg/kg orally once per day, or (D) WEE1i (PD0166285) 0.3 mg/kg intraperitoneally once per day. Both of the WEE1i in combination with the KRASi inhibited tumor growth in the mice, as well as the WEE1i, adavosertib, alone, though the most inhibition was observed with adagrasib and adavosertib (see FIG. 45).

Example 7: Treatment of SNU16 Cells In Vitro

Figure 24:
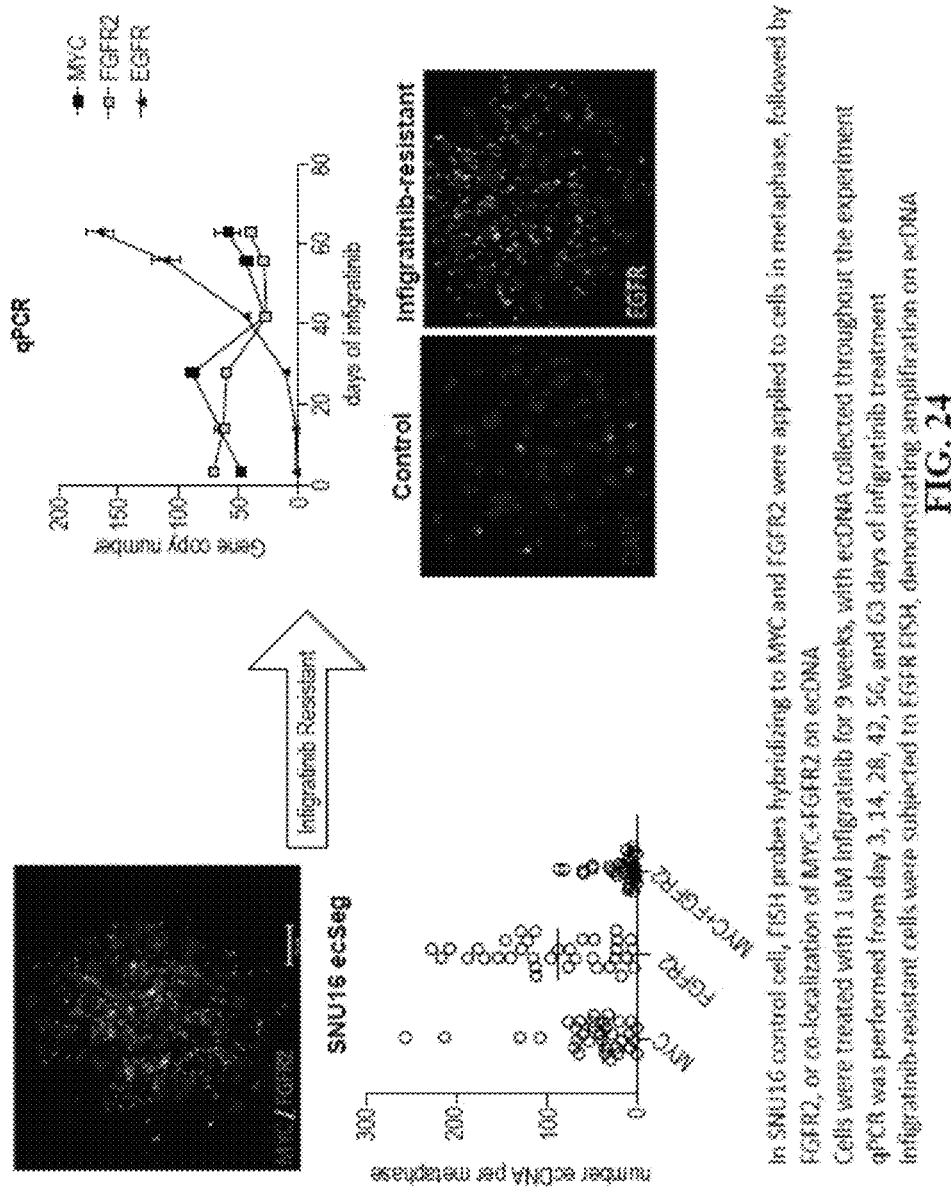
FIG. 24 shows growth of, and ecDNA content in, of SNU16 cells resistant to infigratinib.

SNU16 cells (human stomach undifferentiated adenocarcinoma cell line (ATCC)) in metaphase were assayed for the presence of MYC and FGFR2 by FISH. ecDNA was also quantified. As shown in FIG. 24, high levels of ecDNA containing MYC and FGFR2 are present in these cells, with a subset of the ecDNA containing both MYC and FGFR2.

The SNU16 cells were treated with 1 µM of an FGFR inhibitor (infigratinib) for 9 weeks. DNA was collected at days 3, 14, 28, 42, 56, and 63 days and qPCR was performed to assess copy number for MYC. FGFR2, and EGFR at each time point. Cells after 8 weeks of infigratinib treatment and untreated SNU16 control cells were also assayed by FISH for EGFR. As shown in FIG. 24, as cells developed resistance to the FGFR inhibitor (and thus continued to survive in infigratinib), the copy number of EGFR increased, whereas copy number for MYC and FGFR2, which were already amplified in the starting SNU16 cells, remained relatively constant. As shown by FISH in FIG. 24, EGFR amplification localized to ecDNA in these treated cells.

To assess ecDNA copy number dynamics throughout the development of infigratinib resistance, DNA was extracted using the QIAamp DNA Mini Kit (Qiagen) and the DNA was amplified via quantitative PCR (qPCR) using Taqman copy number assays (ThermoFisher). The EGFR Taqman assay ID was Hs00997424_cn; GFGR2 assay ID was Hs05182482_cn; and the MYC assay ID was Hs03660964_cn. The cycle threshold values were normalized to the internal RNase P Taqman assay, and gene copy number was calculated using the ΔΔCt method and the DNA from a diploid control cell line, DLD1.

To collect cells in metaphase for fluorescent in situ hybridization (FISH), the basic protocol as described in Turner et al, 2019, was followed. Briefly, cells were incubated for at least three hours with colcemid, followed by treatment with a potassium chloride hypotonic solution, and fixation using Camoy's solution (3:1 methanol:glacial acetic acid v/v). Fixed cells in metaphase were dropped onto humidified slides, followed by dehydration in ascending ethanol series. FISH probes hybridizing to EGFR, FGFR2, and MYC were purchased from Empire Genomics. Following probe hybridization, slides were washed with a solution of 0.4×SSC/0.3% IGEPAL buffer, followed by a final wash in 2×SSC/0.1% IGEPAL. Mounting media containing DAPI was applied to the slide, a coverslip was added, and cells in metaphase were imaged using a Keyence BZ-X800 microscope at 630× total magnification.

Images from the FISH assays were used to quantify the numbers of ecDNA containing EGFR, FGFR2, or MYC. Images were uploaded into the ecSEG software developed by Boundless Bio, Inc.

Example 8: RNRi Prevents Development of Primary and Secondary Resistance in SNU16 Cells FIG. 25 shows that simultaneous inhibition of FGFR2 with infigratinib and ecDNA with RNR inhibitor gemcitabine completely inhibits development of primary resistance to infigratinib, 2×10$^6$ SNU16 cells were divided into 6 groups and treated with 1 uM infigratinib, 1 uM erlotinib, 10 nM gemcitabine, 1 uM infigratinib+1 uM erlotinib, and 1 uM infigratinib+10 nM gemcitabine and the cell growth was recorded over 12 weeks. Each treatment arm was terminated once the cell number reached 5×10$^6$. Erlotinib treatment had no effect on cell growth on its own. Gemcitabine delayed cell growth for the first two weeks, but the cells continued to grow quickly after that. Infigratinib strongly suppressed cell growth for 5 weeks, after which cells developed resistance and grew rapidly. Combination treatment of erlotinib and infigratinib had a strong growth inhibitory affect for the first 5 weeks, after which cells started to develop resistance and increased their growth rate for the remainder of the study. However, combination treatment with infigratinib and gemcitabine completely inhibited cell growth for the entire duration of the study and no cells were able to develop resistance.

FIG. 26 shows that RNR inhibitor prevent development of secondary resistance to erlotinib in SNU16 cells. The infigratinib-resistant SNU16 cells (generated as shown in FIG. 25) were subdivided into six groups and each group of 1×10$^6$ cells was subjected to treatment with 1 uM infigratinib, 1 uM erlotinib, 10 nM gemcitabine, or 1 uM erlotinib+10 nM gemcitabine and the cell growth was recorded over 5 weeks. Each treatment arm was terminated once the cell number reached 5×10$^6$. Infigratinib treatment had no effect on cell growth on its own. Gemcitabine, as well as erlotinib, delayed cell growth for the first two weeks, but the cells continued to grow quickly after that. Combination treatment of erlotinib and infigratinib had a moderate growth inhibitory affect for the first 3 weeks, after which cells started to develop resistance and increased their growth rate for the remainder of the study. However, combination treatment with erlotinib and gemcitabine completely inhibited cell growth for the entire duration of the study and no cells were able to develop resistance.

Figure 30:
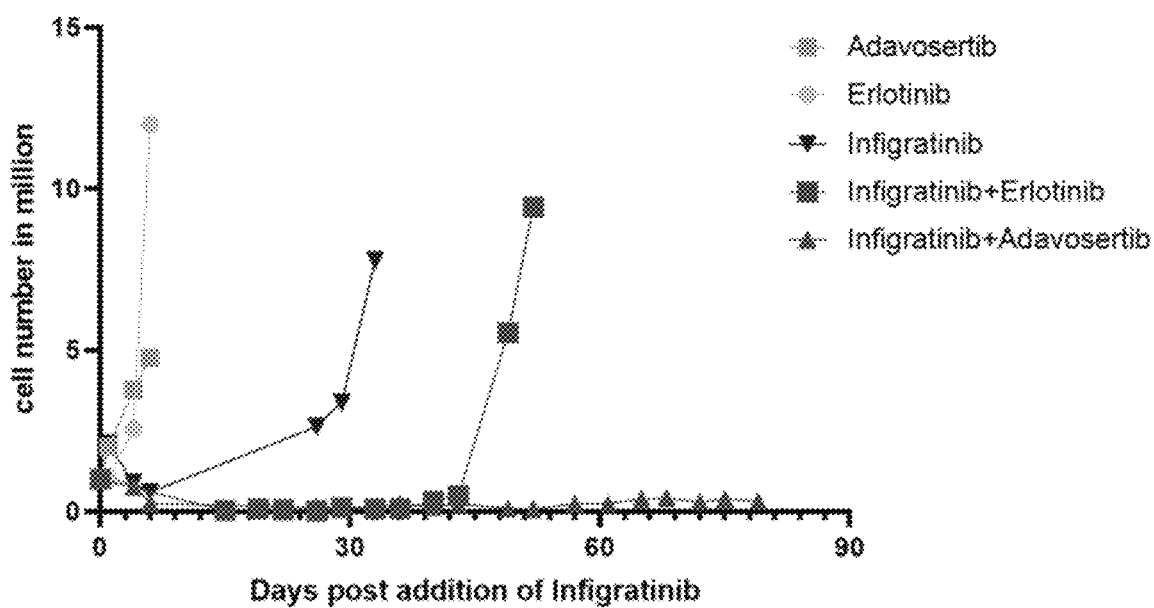
FIG. 30 shows adavosertib prevents resistance of infigratinib treatment in SNU16 cells.

FIG. 30 shows that WEE1 inhibitor, adavosertib, prevented resistance formation upon infigratinib treatment in SNU16 cells. SNU16 cells were subdivided into five groups and each group of 1×10$^6$ cells was subjected to treatment with 1 µM infigratinib, 1 µM erlotinib, 1 µM infigratinib and 1 µM erlotinib, 0.1 µM adavosertib and cell growth was recorded over 9 weeks. Infigratinib resulted in transient growth suppression and erlotinib treatment had no effect on cell growth on its own. Combination treatment of infigratinib and erlotinib delayed cell growth for about six weeks but the cells continued to grow quickly thereafter. However, combination treatment with infigratinib and adavosertib completely inhibited cell growth for the entire duration of the study and no cells were able to develop resistance.

Figure 34:
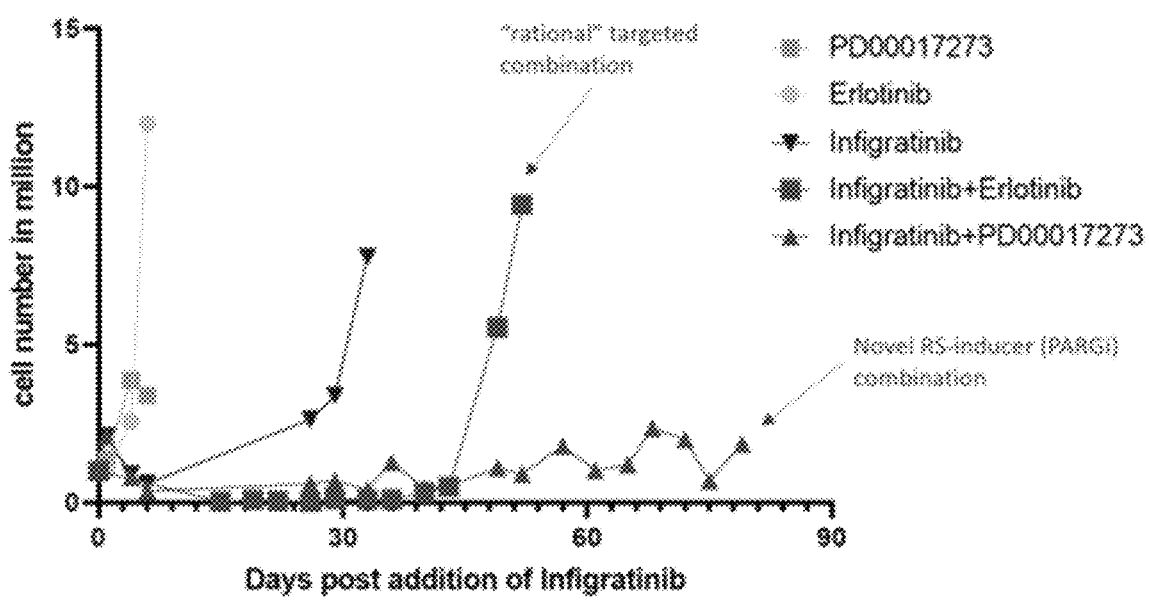
FIG. 34 shows PARG inhibition delays resistance formation to infigratinib treatment of SNU16 cells.

FIG. 34 shows that PARG inhibitor PD00017273 significantly delays resistance formation upon infigratinib treatment in SNU16 cells. SNU16 cells were subdivided into five groups and each group of 1×10$^6$ cells was subjected to treatment with infigratinib, erlotinib, PD00017273, infigratinib and erlotinib, or infigratinib and PD00017273 and cell growth was recorded over 9 weeks. PD00017273 and erlotinib alone had little to no effect on cell growth, whereas infigratinib demonstrated transient growth suppression for approximately 3 weeks. Combination treatment of infigratinib and erlotinib delayed cell growth for about six weeks but the cells continued to grow quickly thereafter. However, combination treatment with infigratinib and PD00017273 reduced cell growth and kept it at low levels for the duration of the study.

Methods: SNU16 control cells were cultured in RPMI-1640 media with 10% FBS under standard tissue culture conditions at 37° C. and with 5% CO$_2$. Low passage control cells were treated with 1 µM infigratinib over the course of 9 weeks. Cells were passaged as needed and media and infigratinib were replaced at least once per week. DNA was collected at day 3 and weeks 2, 4, 6, 8 and 9. Cells in metaphase were collected at 8 weeks from both control and infigratinib-resistant cells.

SNU16 (CRL-5974) cell line was purchased from ATCC. SNU16 cells were grown in RPMI 1640 medium (Fisher Scientific) with 10% FBS and 100 U/ml penicillin/streptomycin (Fisher Scientific). For the resistance experiments, SNU16 cells were plated at 2 million per T75 flask and were treated with either 1 µM infigratinib (Selleck Chemicals), 1 µM erlotinib (Selleck Chemicals), 10 nM gemcitabine (Sigma Aldrich), or a combination. The media was changed and fresh drug was added at least once per week. The cells were counted over the span of several weeks to measure cell growth.

Figure 33:
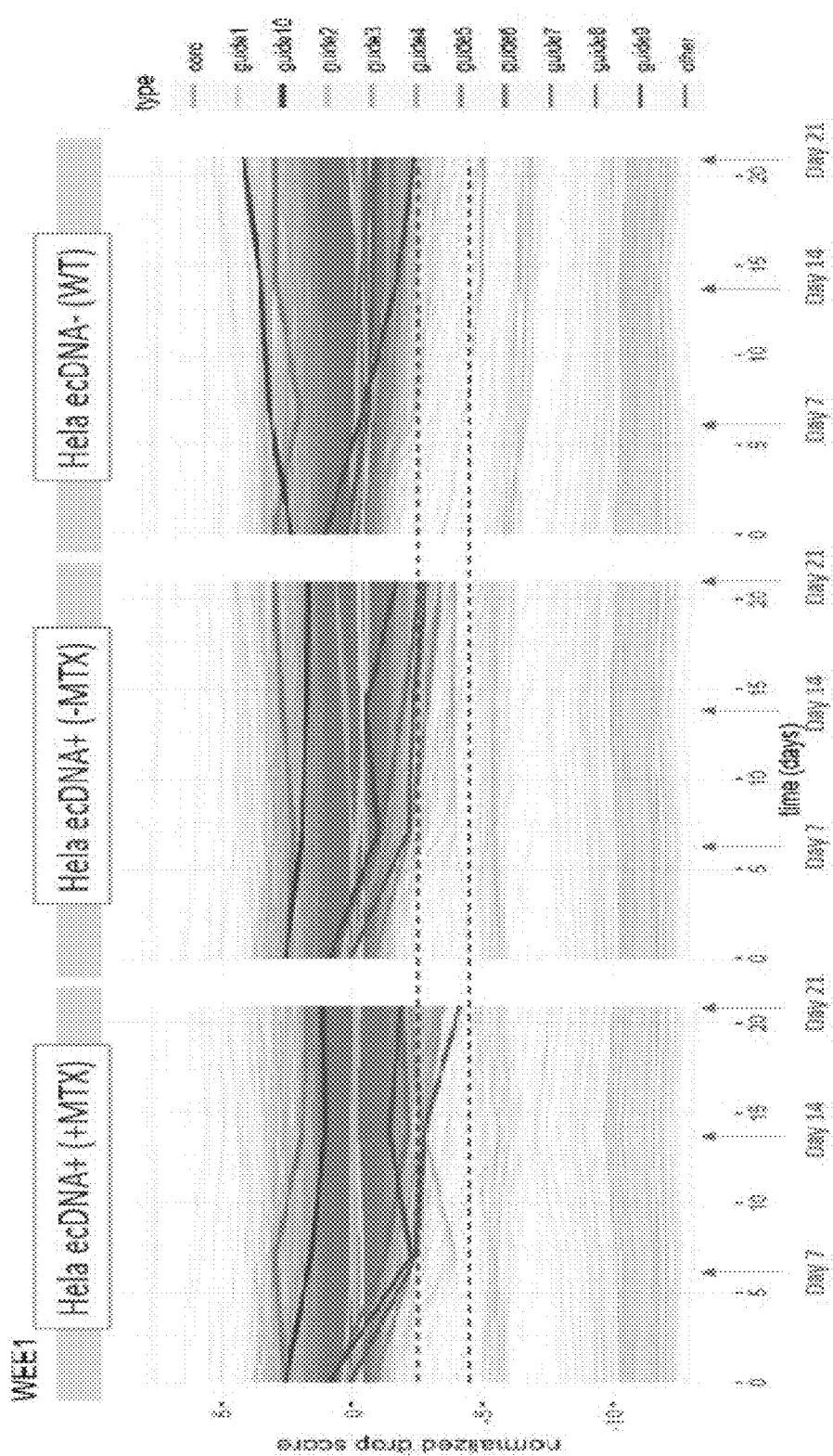
FIG. 33 shows a comparison in sensitivity of HeLa ecDNA+ and HeLa ecDNA− cells to WEE1 knockout.

Example 9: WEE1 Guide Dropout in HeLa ecDNA+ vs. HeLa ecDNA− Kinome CRISPR Screen FIG. 33 shows increased sensitivity of HeLa ecDNA+ over HeLa ecDNA− cells to WEE1 knockout in a pooled CRISPR screen. Levels of normalized sgRNA guide drop score for 10 different guides targeting WEE1 are shown for HeLa ecDNA− cells (WT) as well as HeLa ecDNA+ cells that harbor DHFR amplified on ecDNA. HeLa ecDNA+ were grown either in the absence (−MTX) or presence (+MTX) of 1 uM methotrexate for the duration of the CRISPR screen. Guide drop-out score relative to original levels within the pooled guide library were determined for all three arms by NGS sequencing at 7 days, 14 days and 21 days. Dotted horizontal lines denote differential drop score for the most effective WEE1 guides in ecDNA+ lines vs. ecDNA− line indicating higher sensitivity of ecDNA+ lines to WEE1 knockout further supporting increased sensitivity of these cells to inducers of replication stress.

Figure 38:
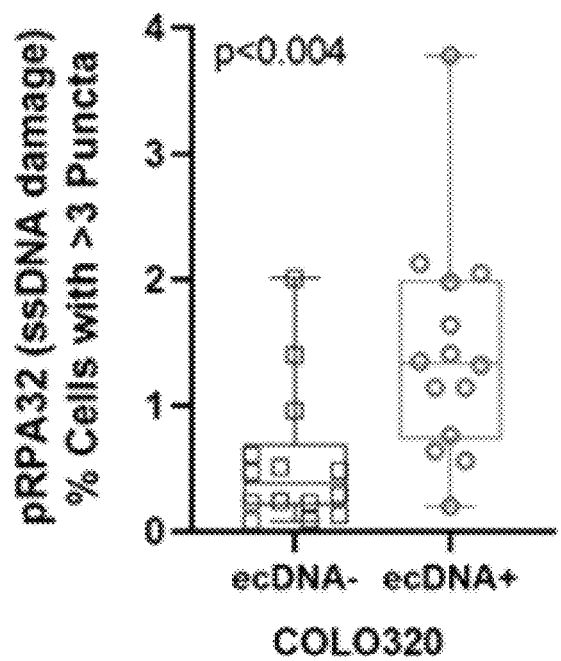
FIG. 38 shows replication stress of ecDNA+ cells.

Example 10: Basal Replication Stress Markers are Elevated and Sensitivity to RS Inducers is Enhanced in ecDNA+ Cells FIG. 38 shows ecDNA+ cells have heightened levels of basal replication stress. To determine intrinsic single-strand DNA (ssDNA)-damage induced replication stress, hyperphosphorylated form of Replication Protein A (RPA) 32 Ser4/Ser8 was detected by immunofluorescence in untreated and fixed ecDNA+ (Colo320 DM) and an ecDNA− (Colo320 HSR) cell line models. Representative box and whisker plot indicating % cell quantification of the total p-RPA32 S4/S8 foci (minimum threshold of >3 puncta/cell) detected by immunofluorescence in ecDNA+ and ecDNA− cells. Total number of 5000 ecDNA− and 6000 ecDNA+ cells with >3 puncta/cell were processed and analyzed. Statistical significance was calculated using nonparametric t-test. ecDNA+ cells are found to have heightened basal replication stress.

Figure 39A:
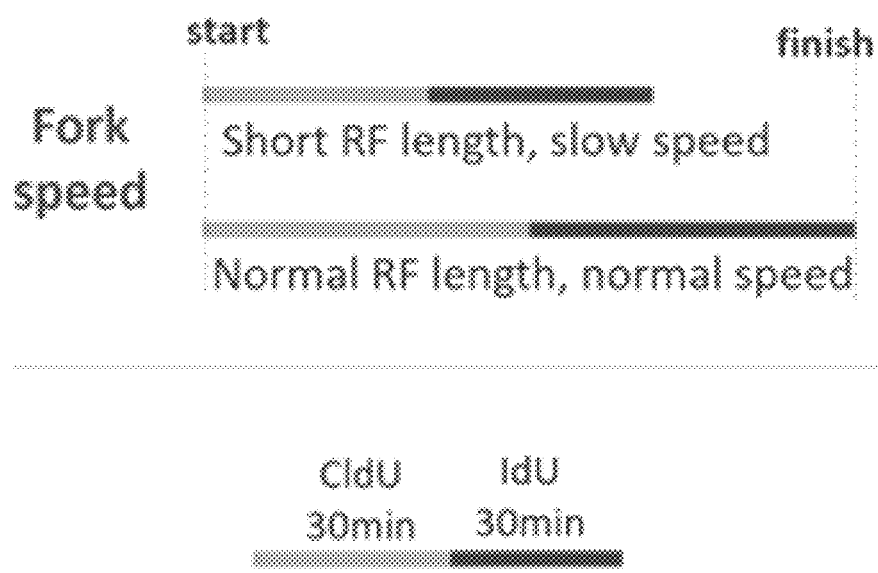
FIG. 39A shows replication fork speed of ecDNA+ and ecDNA− cells.
Figure 39B:
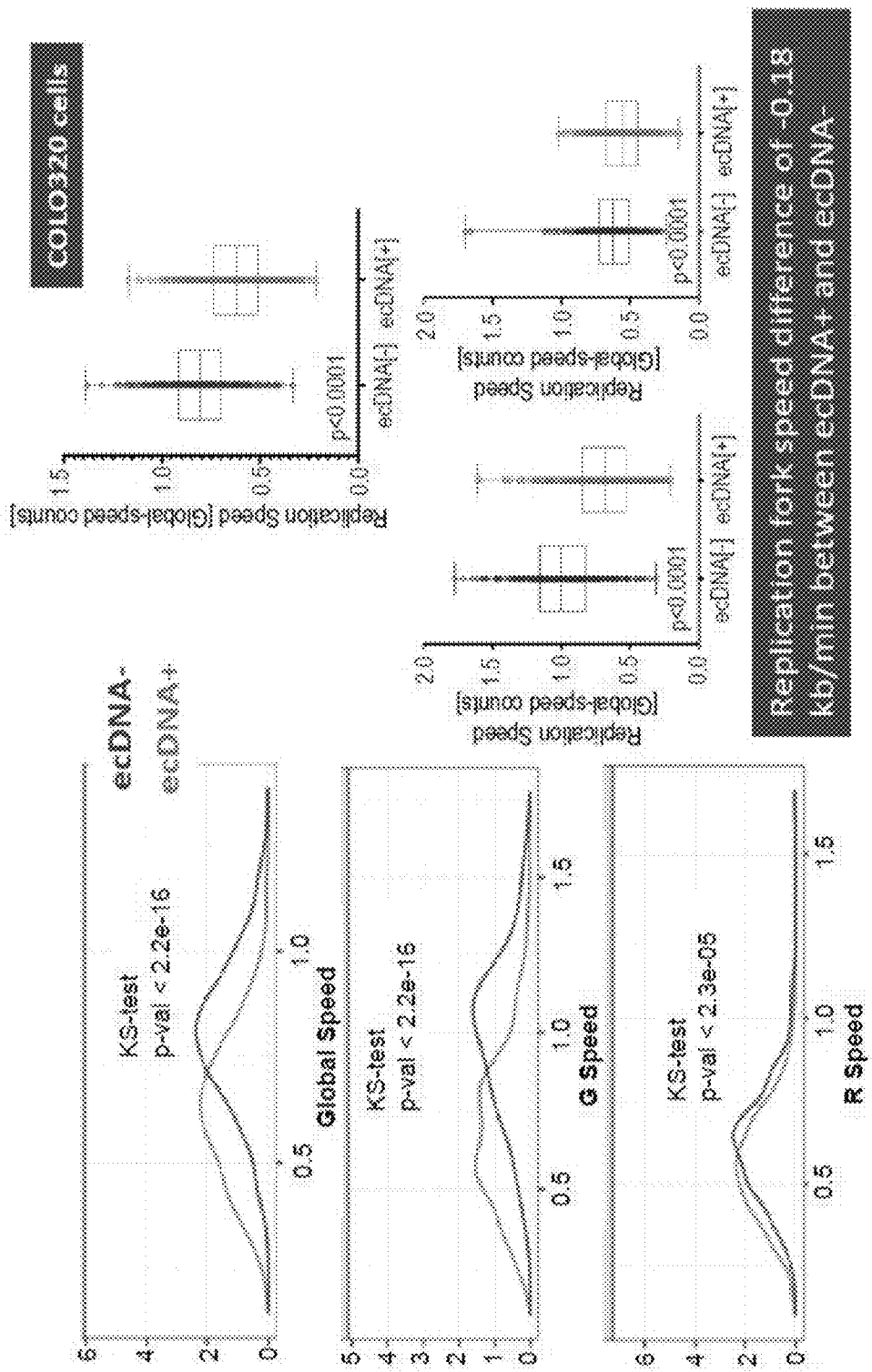
FIG. 39B shows replication fork speed of ecDNA+ and ecDNA− cells.

FIGS. 39A-39B shows that ecDNA+ cells have intrinsically reduced DNA replication fork speeds versus ecDNA− cells with comparable MYC gene amplification on chromosomes. In FIG. 39A, to allow analysis of replication tracts including measurements of fork speed, DNA fiber analysis was conducted in untreated ecDNA+ (Colo320 DM) and ecDNA−(Colo320 HSR) cell line models. The two cell models were pulse-labeled with the thymidine analogues chlorodeoxyuridine (CldU) and iododeoxyuridine (IdU) for 30 min each. Cells were lysed, DNA fibers spread out and immunostained using specific antibodies against CldU and IdU. As shown in FIG. 39B, ecDNA bearing Colo320 DM illustrated average reduced fork speed when compared with Colo320 HSR ecDNA− cells. A difference of −0.18 kb/min in replication fork speed between ecDNA+ and ecDNA− cells was observed. Statistical significance was calculated using nonparametric Kolmogorov-Smirnov test.

Figure 40A:
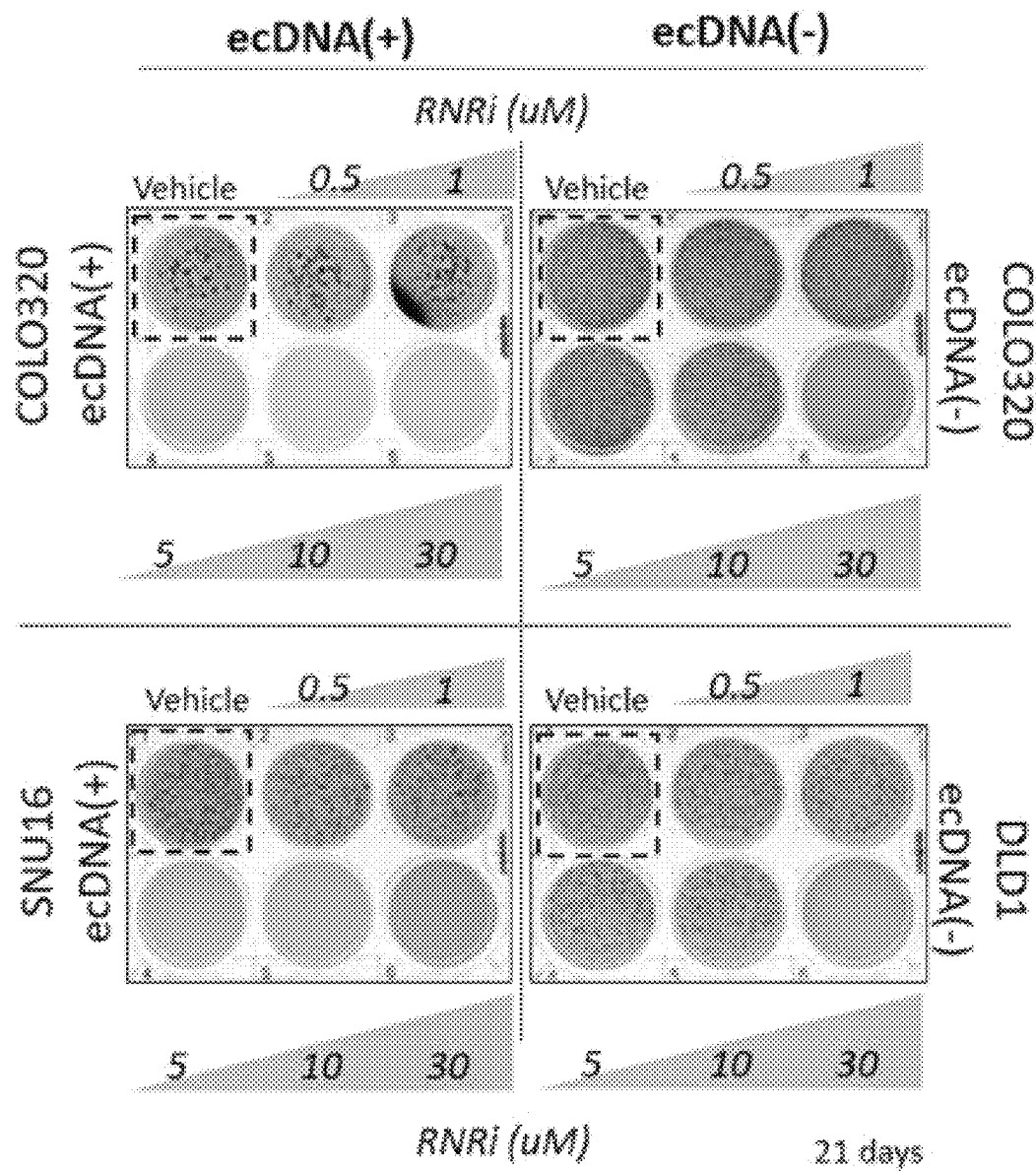
FIGS. 40A-40C show inhibition of RNR blocks nucleotide synthesis, enhanced replication stress, and reduced cellular transformation in ecDNA+ compared to ecDNA− tumor cells.
Figure 40B:
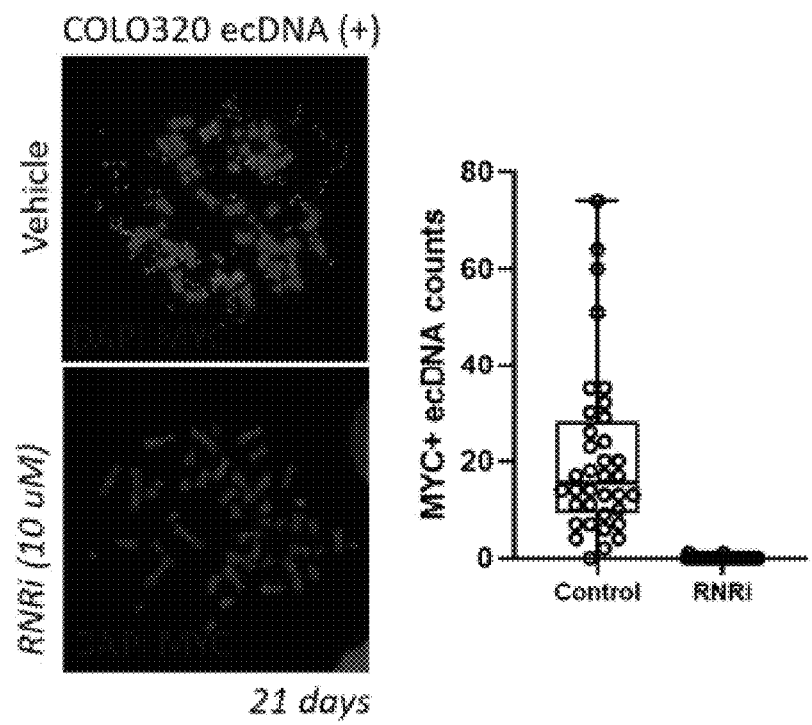
Figure 40C:
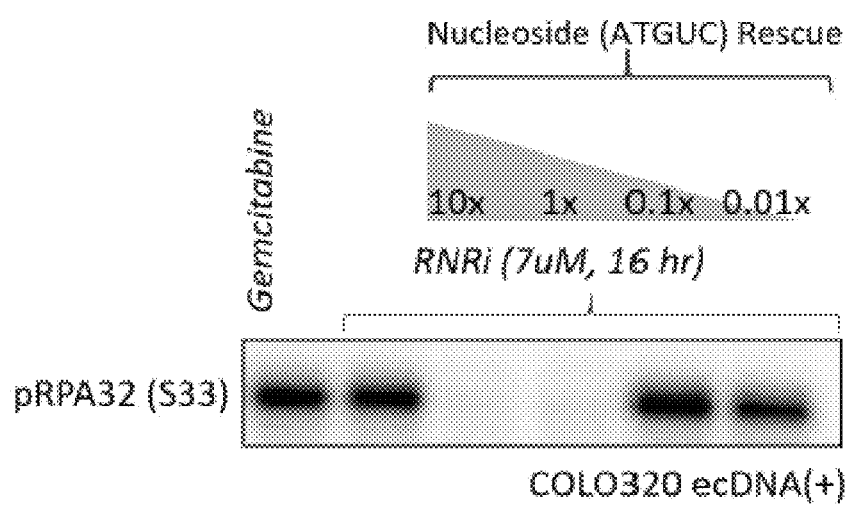

FIGS. 40A-40C show inhibition of RNR blocks nucleotide synthesis causing enhanced replication stress and reduced cellular transformation in ecDNA+ compared to ecDNA-tumor cells. As demonstrated, the exacerbated replication stress observed in ecDNA+ COLO320-DM cells upon inhibition of the RNR results in alteration of cell-proliferation/transformation in FIG. 40A. Data shown in FIG. 40B shows a representative FISH images and quantification of changes in ecDNA carrying amplified oncogene counts. Data shown in FIG. 40C demonstrates that the effects on replication stress by the RNRi are a result of nucleotide depletion. In FIG. 40A, to evaluate cellular transformation, an in vitro soft agar colony formation assay was conducted wherein ecDNA bearing COLO320-DM and SNU16 cell models were grown alongside ecDNA− cell models, COLO320-HSR and DLD1 in this 3D-format assay for 21 days. Cells were treated individually only once on the day of the seeding of cells at increasing doses of RNRi, (5-chloro-2-[[rac-(1S,2R)-2-(6-fluoro-2,3-dimethyl-phenyl)-1-(2-oxo-3H-1,3,4-oxadiazol-5-yl)propyl]sulfamoyl] benzamide). In FIG. 40B, to determine change in ecDNA carrying MYC amplified oncogene counts, ecDNA+ (COLO320-DM) cells were treated with an IC-90 dose (10 uM) of RNRi for 21 days. Cells in log-growth phase were arrested in metaphase. FISH (Florescent in-situ hybridization) for MYC oncogene was performed on the fixed metaphase spreads and the nuclei were counterstained with DAPI. In FIG. 40C, to determine if the exacerbated replication stress observed in the ecDNA+ COLO320-DM cells upon inhibition of the RNR is due to depleted cellular nucleotide pools, ecDNA+ COLO320-DM cells were simultaneously treated with a single IC-70 dose (7 uM) of RNRi, and increasing doses of exogenous nucleosides (ATGUC) for 16 hr. Cells were lysed and immunoblotted with pRPA32-S33 antibody as a marker of ssDNA-damage induced replication stress. Inhibition of RNR was found to block nucleotide synthesis causing enhanced replication stress and reduced cellular transformation in ecDNA+ compared to ecDNA(−) tumor cells.

Figure 41A:
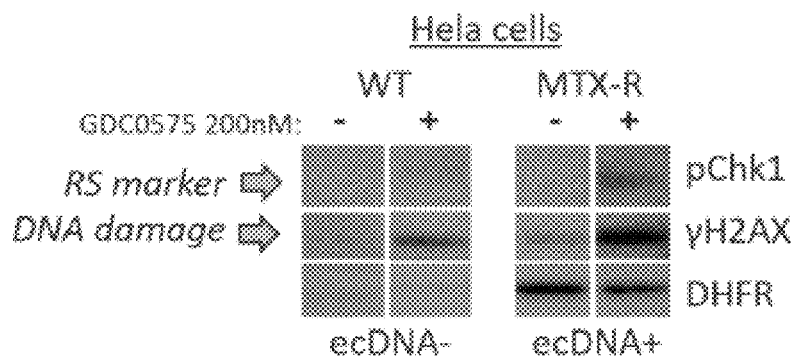
FIGS. 41A-41B shows ecDNA+ cells have increased replication stress in response to CHK1i.
Figure 41B:
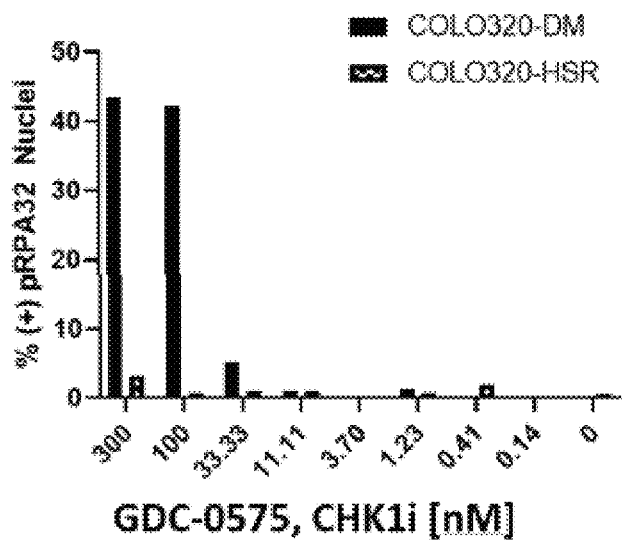

FIGS. 41A-41B show ecDNA+ cells demonstrate enhanced replication stress in response to CHK1i across multiple models. As shown in FIG. 41A, HeLa ecDNA+ cells show increased sensitivity over HeLa ecDNA− cells to Chk1 inhibition by GDC0575. DHFR protein levels were markedly upregulated in HeLa ecDNA+ cells which harbor DHFR ecDNA and were grown in the presence of 1 uM methotrexate (MTX) to maintain resistance (MTX-R). Upon treatment with 200 nM GDC0575 for 24 h, HeLa ecDNA+ cells exhibited a much stronger induction of markers of RS and DNA damage than ecDNA− cells. Increased Chk1 phosphorylation at S345 indicates higher activation of RS-activated ATR kinase, while increased gH2AX indicates increased damage resulting from DNA double stranded breaks triggered by replication stress. FIG. 41B shows an experiment to determine single-strand DNA (ssDNA)-damage induced replication stress upon inhibition of CHK1 pathway. Hyperphosphorylated form of Replication Protein A (RPA) 32 Ser4/Ser8 was detected by immunofluorescence in fixed ecDNA+ (Colo320 DM) and ecDNA− (Colo320 HSR) cell line models that were previously treated with CHK1 i GDC-0575 for 16 hr. Representative bar graph represents % total nuclei positive for P-RPA32 S4/S8 foci (minimum threshold of >3 puncta/nuclei) detected by immunofluorescence in ecDNA+ and ecDNA− cells. CHK1 inhibition was found to increases pRPA levels in ecDNA+ (DM) cells vs. matched ecDNA− (HSR) cells.

Figure 42A:
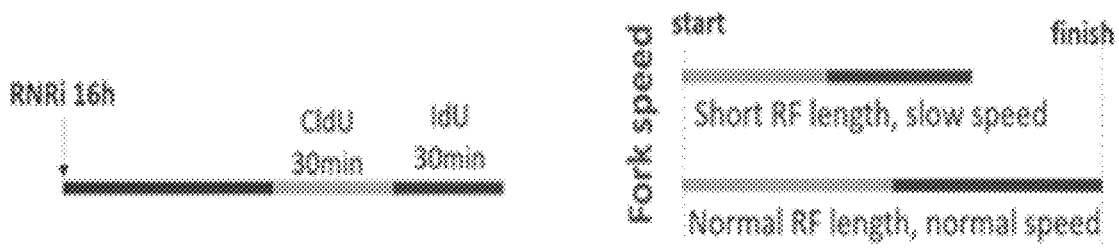
FIGS. 42A-42B shows increased replication fork dysfunction in ecDNA+ cancer cells compared with ecDNA− cells with RNR pathway inhibition.
Figure 42B:
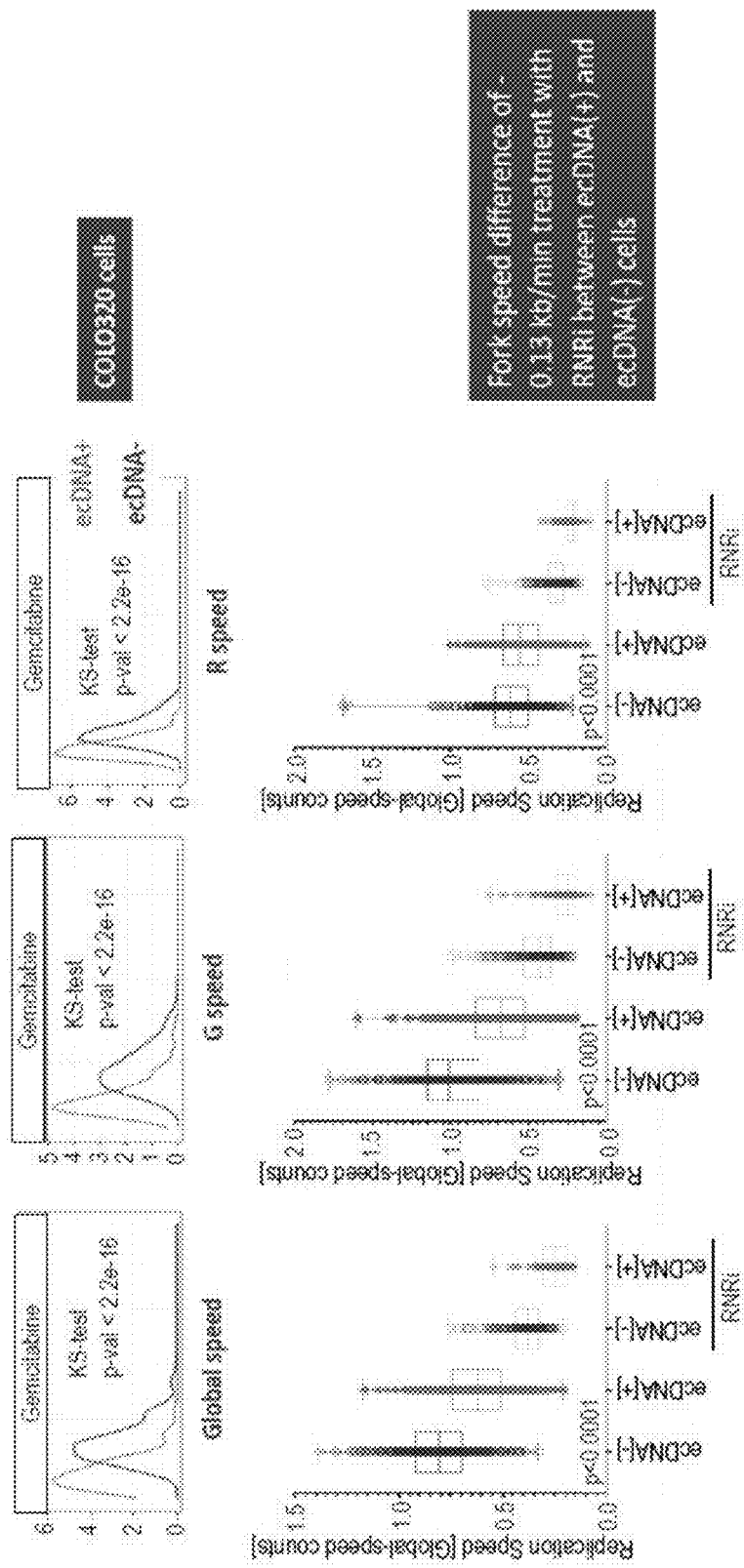

FIGS. 42A-42B show intrinsic replication fork dysfunction in ecDNA(+) cancer cells is further compromised by RNR inhibition relative to ecDNA(−) cells. To allow analysis of replication tracts upon inhibition of RNR pathway, including measurements of fork speed, DNA fiber analysis was conducted in ecDNA+ (Colo320 DM) and ecDNA− (Colo320 HSR) cell line models treated with RNRi gemcitabine for 16 hr. The two cell models were then pulse-labeled with the thymidine analogues chlorodeoxyuridine (CldU) and iododeoxyuridine (IdU) for 30 min each (FIG. 42A). Cells were lysed, DNA fibers spread out and immunostained using specific antibodies against CldU and IdU. As shown in FIG. 42B, the intrinsic replication fork dysfunction in ecDNA+ cancer cells is further compromised upon RNR inhibition relative to ecDNA− cells, although a decrease in replication fork speed was also observed in Colo320 HSR ecDNA− cells upon treatment with RNRi. A difference of −0.13 kb/min in replication fork speed between ecDNA+ and ecDNA− cells treated with RNRi was observed. Statistical significance was calculated using nonparametric Kolmogorov-Smirnov test.

Figures 43A, 43B:
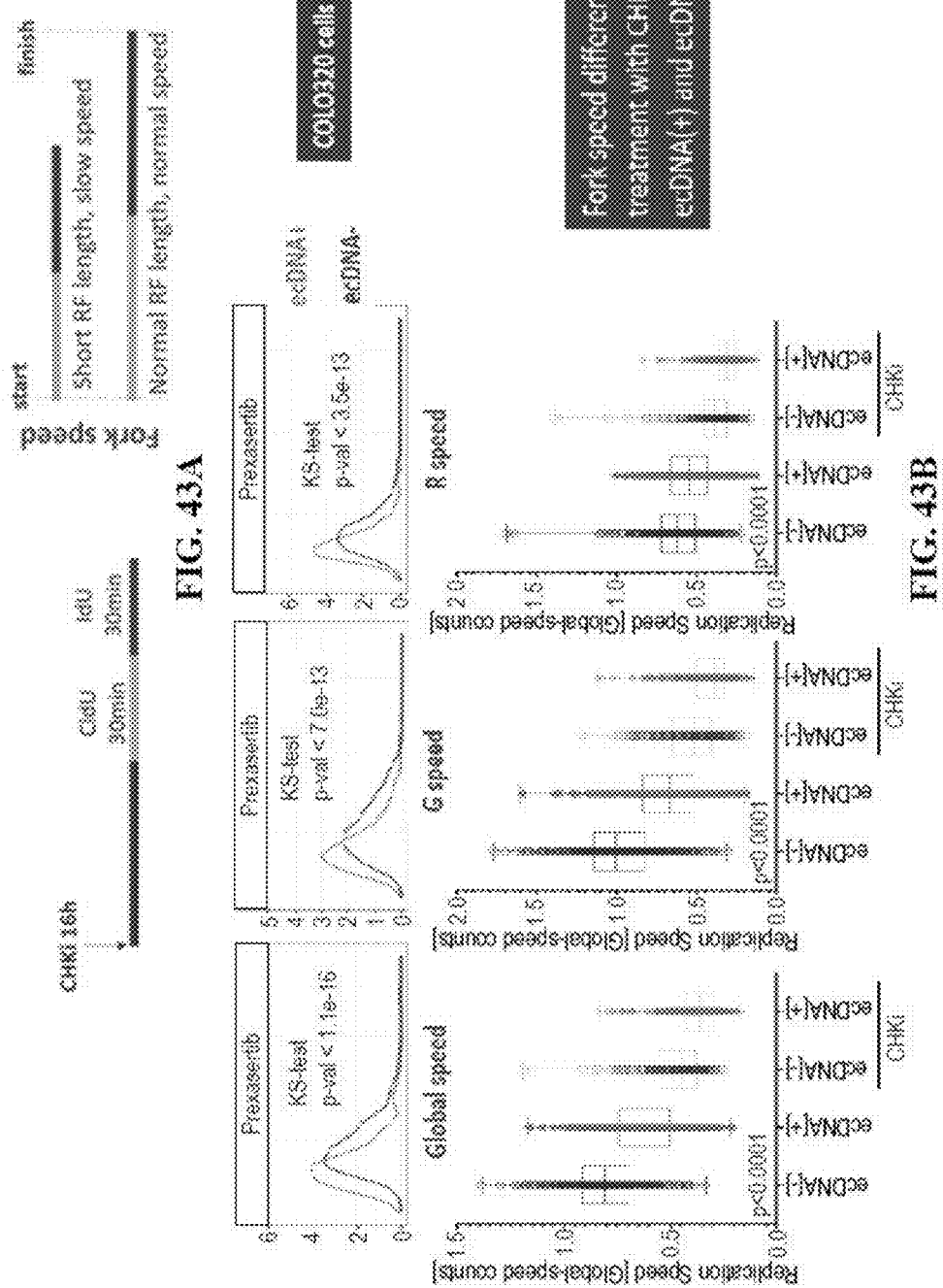
FIG. 43A-43B shows increased replication fork dysfunction in ecDNA+ cells compared with ecDNA− cells with CHK1 inhibition.

FIGS. 43A-43B show intrinsic replication fork dysfunction in ecDNA+ cancer cells is further compromised by CHK1 inhibition relative to ecDNA− cells. To allow analysis of replication tracts upon inhibition of CHK1 pathway including measurements of fork speed, DNA fiber analysis was conducted in ecDNA+ (Colo320 DM) and ecDNA− (Colo320 HSR) cell line models treated with CHK1i Prexasertib for 16 hr. The two cell models were then pulse-labeled with the thymidine analogues chlorodeoxyuridine (CldU) and iododeoxyuridine (IdU) for 30 min each (FIG. 43A). Cells were lysed, DNA fibers spread out and immunostained using specific antibodies against CldU and IdU. As shown in FIG. 43B, the intrinsic replication fork dysfunction in ecDNA(+) cancer cells is further compromised upon CHK1 inhibition relative to ecDNA(−) cells, although a decrease in replication fork speed was also observed in Colo320 HSR ecDNA− cells upon treatment with CHK1i. A difference of −0.1 kb/min in replication fork speed between ecDNA+ and ecDNA− cells treated with CHK1i was observed Statistical significance was calculated using nonparametric Kolmogorov-Smirnov test.

Figure 44:
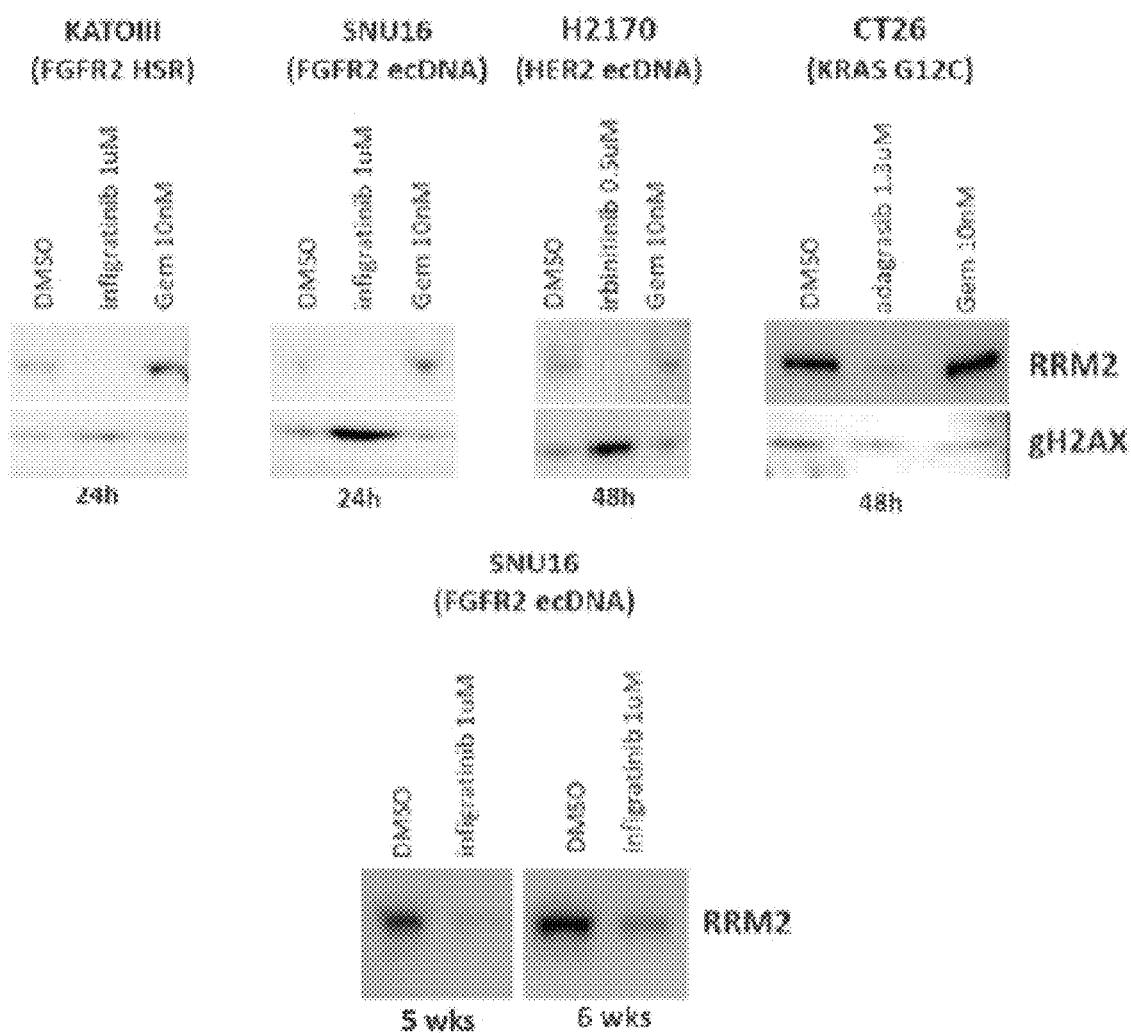
FIG. 44 shows reduced protein levels of RRM2 in cells treated with oncoprotein inhibitors.

FIG. 44 shows that targeted therapy using pharmacological inhibition of the primary oncogenic driver in cancer cells results in reduced protein levels of RRM2 subunit of RNR. Four cell lines shown that have previously been determined to harbor oncogenes amplified either on ecDNA or HSR, or to lack amplifications (CT26). Inhibition of the oncoprotein resulted in a rapid reduction of RRM2 protein levels within 24-48 h suggesting that these inhibitors may indirectly lead to a reduction of dNTPs levels and an induction of replication stress. Consistent with this hypothesis, inhibition of ecDNA-amplified HER2 and FGFR2 in H2170 and SNU16 cells, respectively, showed a concomitant increase in gH2AX, a known marker of collapsed replication forks and DNA damage. Interestingly, KATOIII cells that harbor FGFR2 amplification as HSR, and CT26 cells that do not harbor any oncogene amplification, did not show an increase in gH2AX despite reduced RRM2 levels, further supporting that ecDNA-bearing cells are particularly sensitive to a reduction of RRM2 levels and replication stress. In addition, this reduction of RRM2 levels in SNU16 cells was shown to be maintained for a prolonged period of 5-6 weeks suggesting a lack of compensatory mechanisms for maintaining RNR activity. These findings strongly reinforce the rationale for combination of targeted therapies with RS-inducing agents in ecDNA-bearing cancers.

Example 11: Resistance to Targeted Therapy in ecDNA+ vs. ecDNA− Cells

Table 2 (below) shows the timeline of resistance development in ecDNA+ vs. ecDNA− cells. To measure growth kinetics over time, each cell line was treated once or twice per week with targeted inhibitor against the amplified oncogene. In the case of SKBR3 and Calu-3, irbinitinib was increased over time, starting at 2× the relative EC50 and then increase to 4× the relative EC50 for a total duration of 6 weeks. In the case of H2170, irbinitinib was used at EC90 (500 nM) upfront and the cell growth was monitored for 3 weeks, at which point the cells were growing at a similar rate as DMSO control cells. In the case of SNU16 and KATOIII, infigratinib was added at EC90 (1 uM) and the cell growth was monitored for 6 and 11 weeks, respectively.

For these long-term growth curves, the EC50 of targeted therapy was first determined in short term 5 day viability assays. To determine the EC50 of irbinitinib, H2170 cells were plated at 3000 cell/well in a 96-well plate; SKBR3 and Calu-3 cells were plated at 3500 cells/well in a 96-well plate. All cells were dosed with irbinitinib continuously for 5 days (serial dilutions ranging from 12 nM to 1 uM) along with a DMSO control. EC50 curves were determined based on cell viability using CellTiter-Glo 2.0 reagent (Promega). To determine the EC50 of infigratinib, SNU16 and KATOIII cells were plated at 1000 cells/well in a 96-well plate and were treated with infigratinib continuously for 5 days (serial dilutions ranging from 4 nM to 1 uM) along with a DMSO control. EC50 curves were determined based on cell viability using CellTiter-Glo 2.0 reagent (Promega). Targeted therapy directed against driver oncogenes showed differential effects depending on the type of oncogene amplification. Cell lines, such as H2170 and SNU16, which harbor oncogene amplification on ecDNA exhibited a markedly better ability to gain resistance and continue to grow in the presence of targeted therapy than cell lines, such as SKBR3, Calu-3, and KATOIII, which harbor chromosomal oncogene amplification (Table 2).

TABLE 2

Targeted Therapy Effects

| Tumor Line | Amplification | Amplification type | Drug treatment | 3-5 day acute cytotoxicity EC50 (μM) | Long-term culture growth properties |
|---|---|---|---|---|---|
| H2170 | ERBB2 | ecDNA | irbinitinib | 0.110 | Increased proliferation <3 weeks |
| SKBP3 | ERBB2 | Chromosomal | irbinitinib | 0.043 | <1% viability >6 weeks |
| Calu3 | ERBB2 | Chromosomal | irbinitinib | 0.414 | Reduced proliferation (50%), >6 weeks |
| SNU16 | FGF2 | ecDNA | infigratinib | 0.014 | Near normal proliferation <5 weeks |
| KATOIII | FGF2 | Chromosomal | infigratinib | 0.013 | <1 viability >10 weeks |

While preferred embodiments of the present invention have been shown and described herein, it will be obvious to those skilled in the art that such embodiments are provided by way of example only. Numerous variations, changes, and substitutions will occur to those skilled in the art without departing from the invention. It should be understood that various alternatives to the embodiments described herein may be employed. It is intended that the following claims define the scope of embodiments and that methods and structures within the scope of these claims and their equivalents be covered thereby.

What is claimed is:

1. A method of treating an ecDNA-associated cancer in a subject comprising:
   administering to the subject a therapeutically effective amount of (i) a replication stress pathway agent (RSPA), wherein the RSPA is a WEE1 inhibitor, and (ii) a cancer-targeted therapeutic agent,
   wherein cells of the ecDNA-associated cancer have an ecDNA signature, wherein the cells of the ecDNA-associated cancer comprise an amplification of a first gene or portion thereof and the amplification is present on ecDNA, and
   wherein the cancer-targeted therapeutic agent is directed against a protein encoded by the first gene,
   thereby decreasing growth or number of the cells of the ecDNA-associated cancer in the subject.

2. The method of claim 1, wherein the first gene comprises an oncogene, a drug-resistance gene, a therapeutic target gene, or a checkpoint inhibitor gene.

3. The method of claim 1, wherein the subject has not been previously treated with the cancer-targeted therapeutic agent.

4. The method of claim 1, wherein the cells of the ecDNA-associated cancer are resistant or non-responsive to a previous therapeutic agent.

5. The method of claim 1, wherein the method prevents an increase of ecDNA in the cells of the ecDNA-associated cancer.

6. The method of claim 1, wherein a level of oncogene amplification and/or a level of copy number variation (CNV) in circulating cells of the ecDNA-associated cancer is reduced after treatment as compared to the level of oncogene amplification and/or CNV in the circulating cells of the ecDNA-associated cancer prior to treatment.

7. The method of claim 1, wherein the ecDNA signature is selected from the group consisting of a gene amplification; a p53 loss of function mutation; absence of microsatellite instability (MSI-H); a low level of PD-L1 expression; a low level of tumor inflammation signature (TIS); a low level of tumor mutational burden (TMB); an increased frequency of allele substitutions, insertions, or deletions (indels); and any combination thereof.

* * * * *